United States Patent [19]
Atassi

[11] Patent Number: 5,861,477
[45] Date of Patent: *Jan. 19, 1999

[54] CYCLIC PEPTIDE CATALYSTS MODELED ON ENZYME ACTIVE SITES

[76] Inventor: M. Zouhair Atassi, 11743 Cawdor Way, Houston, Tex. 77024

[ * ] Notice: The term of this patent shall not extend beyond the expiration date of Pat. No. 5,759,834.

[21] Appl. No.: 535,298

[22] PCT Filed: May 18, 1994

[86] PCT No.: PCT/US94/05569

§ 371 Date: Jun. 19, 1996

§ 102(e) Date: Jun. 19, 1996

[87] PCT Pub. No.: WO94/28018

PCT Pub. Date: Dec. 8, 1994

Related U.S. Application Data

[63] Continuation-in-part of Ser. No. 63,640, May 18, 1993, abandoned, and a continuation-in-part of Ser. No. 461,597, Jun. 5, 1995, Pat. No. 5,759,834.

[51] Int. Cl.$^6$ .............................. C07K 7/52; C07K 7/50; C12N 9/22; C12N 9/36; C12N 9/46; C12N 9/48
[52] U.S. Cl. .......................... 530/317; 530/324; 530/334; 435/199; 435/206; 435/213; 435/212
[58] Field of Search ................................ 435/183, 188.5, 435/195, 199, 206, 213, 91.31; 536/23.2; 530/317, 324, 334

[56] References Cited

U.S. PATENT DOCUMENTS 4,751,180  6/1988  Cousens et al. ........................ 435/69.7

OTHER PUBLICATIONS

Buono et al. (1996) J. Comp.–Aided Mol. Des., 10(3), "Synthesis and Conformationa Analaysis by $^1$H–NMR and Restrained Molecular Dynamics Simulations of the Cyclic Decapeptide [Ser–Tyr–Ser–Met–Glu–His–Phe–Arg–Trp–Gly]", pp. 213–232.

Cunningham et al. (1997) Curr. Opin. Struct. Biol., 7(4), "Minimized Proteins", pp. 457–462.

Walse et al. (1996) J. Comp.–Aided Mol. Des., 10(1), "Structure of a Cyclic Peptide with a Catalytic Triad, Determined by Computer Simulation and NMR Spectroscopy", pp. 11–22.

Gutte et al. (1979) Nature, "Design, Synthesis and Characterization of a 34–Residue Polypeptide That Interacts with Nucleic Acids", pp. 650–655.

Atassi et al. (1993) Proc. Nat. Acad. Sci., USA, 90, "Design of Peptide Enzymes (Pepzymes): Surface–Simulation Synthetic Peptides That Mimic the Chymotrypsin and Trypsin Active Sites Exhibit the Activity and Specificity of the Respective Enzyme", pp. 8282–8286.

Atassi (1985) Biochem. J., 226, "Surface–Simulation Synthesis of the Substrate–Binding Site of an Enzyme", pp. 477–485.

Matthews et al. (1994) Proc. Bat. Acad. Sci., USA, 91, "Can Small Cyclic Peptides Have the Activity and Specificity of Proteolytic Enzymes?", pp. 4103–4105.

(List continued on next page.)

Primary Examiner—Jon P. Weber
Attorney, Agent, or Firm—Conley, Rose & Tayon, P.C.

[57] ABSTRACT

PEPZYMES™, chemically synthesized cyclic peptides, modeled on the active sites of naturally-occurring enzymes represented by chymotrypsin, trypsin, lysozyme, ribonuclease, urokinase, tissue plasminogen activator and their analogs are disclosed. The conformational constraints imposed on the peptide residues cause the amino acids of the peptide to assume a three-dimensional spatial relationship relative to the substrate that is essentially equivalent to that of the corresponding active site amino acids of the natural enzyme in its catalytically active state. The new cyclic peptides catalyze the same reaction as the native enzyme being modeled, but have amino acid sequences that are substantially shorter than the naturally-occurring enzymes, and do not occur in the same linear relationship in the naturally-occurring enzymes. Methods of producing PEPZYMES™ are described.

12 Claims, 40 Drawing Sheets

OTHER PUBLICATIONS

Corey et al. (1994) *Proc. Nat. Acad. Sci. USA,* 91, "Cyclic Peptides as Proteases: A Revaluation", pp. 4106–4109.

Wells et al. (1994) *Proc. Nat. Acad. Sci., USA, 91,* "A Reinvestigation of a Synthetic Peptide (TrPepz) Designed to Mimic Trypsin", pp. 4110–4114.

Rizo et al. (1992) Constrained Peptides: Models of Bioacvtive Peptides and protein Substructures, pp. 387–418.

Stryer (1975) "Biochemistry (2nd Ed.)", Freeman and Company, San Francisco, pp. I–xxi.

Sakar (1981) "Cyclopeptide Macrocycles", pp. 251–313, in Progress in Macrocyclic Chemistry, Ed. Izatt et al., John Wiley & Sons, New York.

Leatherbarrow et al. (1991) *Biochemistry,* 30, "Design of a Small Peptide–Based Proteinase Inhibitor by Modeling the Active–Site Region of Barley Chymotrysin Inhibitor 2", pp. 10717–10721.

Marrone et al. (1994) J. Am. Chem. Soc., 116(15), "Pepzyme Dynamics and Conformation: A Molecular Dynamics Study in Water", pp. 6987–6988.

Kirby (1996) Angew. Chem. Int. Engl., 35(7), "Enzyme Mechanisms, Models, and Mimics", pp. 707–724.

Corey et al. (1996) Proc. Natl. Acad. Sci. USA, 93(21), "On the Failure of De Novo–Designed Peptides as Biocatalysts", pp. 11428–11434.

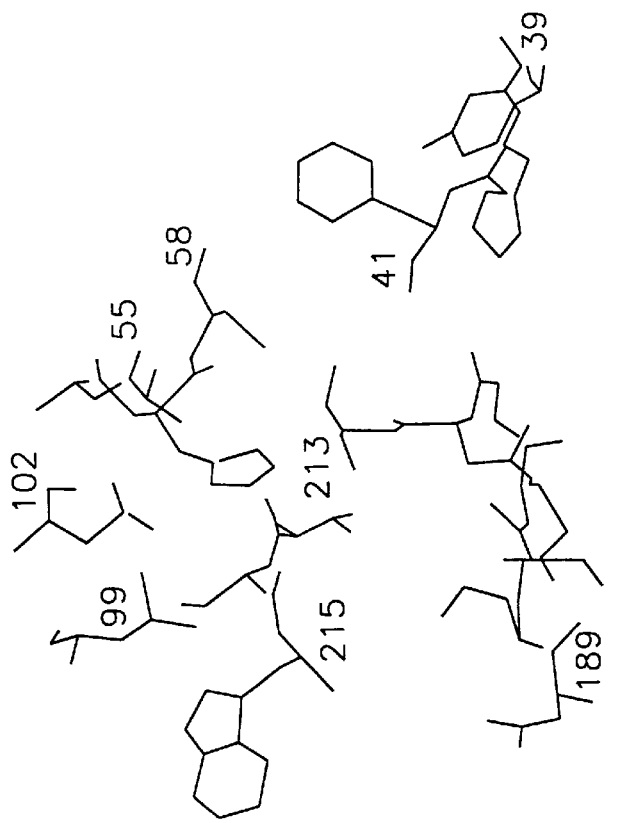
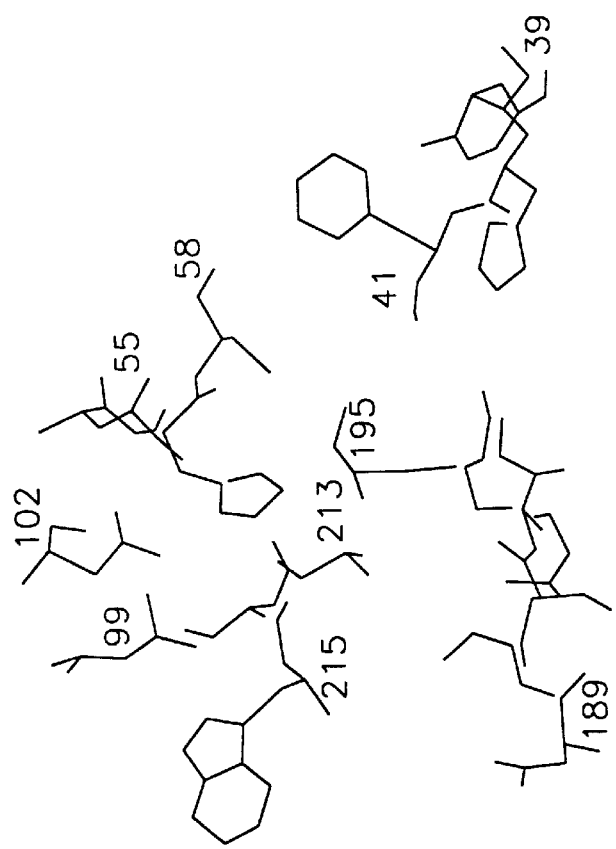
FIG. 6B

QUERY SEQUENCE - CHYMOTRYPSIN (EC 3.4.21.1) B PRECURSOR - BOVINE
PEPTIDE SEQUENCE ACTIVE SITE RESIDUES/SUBSTITUTIONS

| # | F 39 | H 40 | F 41 | A 55 | A 56 | H 57 | C 58 | I 99 | D 102 | S 189 | S 190 | G' 191 | M 192 | G 193 | D 194 | S 195 | V 213 | S 214 | W 215 |
|---|---|---|---|---|---|---|---|---|---|---|---|---|---|---|---|---|---|---|---|
| 1 | | | | | | | | V | | | | | | | | | | | |
| 2 | | | | | | | | V | | | | | | | | | | | |
| 3 | | | | | | | | V | | | | | | | | | | | |
| 4 | | | | | | | | V | | | | | | | | | | | |
| 5 | | | | | | | | V | | | | | | | | | | | |
| 6 | | | | | | | | V | | | | | | | | | | | |
| 7 | | | | | | | | | | | | | | | | | | | |
| 8 | | | | | | | | | | | | | | | | | | | |
| 9 | | | | | | | | | | | | | | | | | | | |
| 10 | | | | | | | | | | | | | | | | | | | |
| 11 | R | | | | | | | S | | D | | | Q | | | | T | | |
| 12 | R | | | | | | | S | | D | | | Q | | | | T | | |
| 13 | K | | | | | C | | | | D | R | | Q | | | | T | | |
| 14 | M | | | | | | | T | | D | | | Q | | | | T | | |
| 18 | E | | | | | | | S | | D | | | Q | | | N | T | | |
| 19 | G | | | | K | | | S | | D | | | Q | | | | | | |
| 22 | M | | | | | | | A | | D | | | Q | | | | | | |
| 24 | K | | | | C | | | | | | R | | Q | | | | | | |
| 27 | Y | | | | | | | L | | D | | | | | | | T | | |

| # | F 39 | H 40 | F 41 | A 55 | A 56 | H 57 | C 58 | I 99 | D 102 | S 189 | S 190 | G' 191 | M 192 | G 193 | D 194 | S 195 | V 213 | S 214 | W 215 |
|---|---|---|---|---|---|---|---|---|---|---|---|---|---|---|---|---|---|---|---|
| 28 | R |   |   |   |   |   |   | S |   | D |   |   | Q |   |   |   | T |   |   |
| 29 | Q |   | N |   |   |   |   | N |   | D |   |   | Q |   |   |   | T |   |   |
| 30 | R |   |   |   |   |   |   |   |   | Q | G |   | K | D | A |   |   |   |   |
| 31 | Y |   |   |   |   |   |   | L |   | D |   |   | Q |   |   |   |   |   |   |
| 32 | R |   | N |   |   |   |   | S |   | D |   |   | Q |   |   |   | T |   |   |
| 33 | Q |   | N |   |   |   |   | N |   | D |   |   | Q |   |   |   | T |   |   |
| 34 | R |   |   |   |   |   |   |   |   | Q | G |   | K | D | A | C |   |   |   |
| 35 | R |   |   |   |   |   |   |   |   | Q | G |   | K | D | A | C |   |   |   |
| 36 | R |   | R |   |   |   |   |   |   | A | G |   | K | D | S | C |   |   |   |
| 38 | Y |   |   |   | R |   |   | Y | Q | D |   |   | Q | D | A | Y | I | I | P |
| 40 | Q |   | I |   |   | Q |   | L |   | G | A |   | E |   |   | C |   |   |   |
| 41 | R |   |   |   | R | Q |   | F |   | Q | G |   | K |   |   |   |   |   |   |
| 42 | Y |   |   |   | R | Q |   | L | Q | Q |   |   | Q | D | A |   |   |   |   |
| 43 | Y |   |   |   |   |   |   | S | Q | D |   |   | Q |   |   |   | I | I | P |
| 44 | Q |   |   |   |   |   |   | S |   | D | A |   | E |   |   | Y | I | I | P |
| 45 | Q |   | R |   |   |   |   |   |   | G | A |   | E |   |   | Y |   |   |   |
| 46 | S |   |   |   |   |   |   |   |   | G | A |   | Q |   |   |   |   |   |   |
| 47 | Y |   |   |   |   |   |   |   |   | D |   |   | Q |   |   |   |   |   |   |
| 48 | Y |   |   |   |   |   |   |   |   | D |   |   | Q |   |   |   |   |   |   |
| 49 | Q |   |   |   | R | Q |   | A | Q | G | A |   | E |   |   | Y | I | I | P |

FIG. 16A3

| # | F 39 | H 40 | F 41 | A 55 | A 56 | H 57 | C 58 | I 99 | D 102 | S 189 | S 190 | G' 191 | M 192 | G 193 | D 194 | S 195 | V 213 | S 214 | W 215 |
|---|---|---|---|---|---|---|---|---|---|---|---|---|---|---|---|---|---|---|---|
| 50 | Y | | | | | | | | | | | | | | | | | | |
| 51 | Y | | | | | | | | | | | | | | | | | | |
| 52 | S | | S | | | | | L | | D | | | Q | | | | | | |
| 53 | S | | | | G | | | L | | D | G | | Q | | | | | | |
| 54 | S | | S | | | | | M | | D | A | | Q | | | | | | |
| 55 | A | | S | | | | | T | | E | G | | K | | | | | | |
| 56 | S | | | | G | | | M | | D | G | | Q | | | | | | |
| 57 | R | | L | | | | | M | | E | A | | K | | | | | | |
| 58 | S | | R | | | | | T | | E | G | | K | D | | | | | |
| 59 | R | | L | | | | | S | | D | R | | K | D | | | | | |
| 60 | N | | M | | | | | S | | D | A | | K | D | A | C | | | |
| 61 | R | | L | | | | | G | | D | A | | K | D | | | | | |
| 62 | T | | L | | | | | G | | D | A | | K | D | | C | T | | |
| 63 | E | G | | | | | | G | | D | A | | Q | | | | T | | |
| 64 | Y | | | | | | | Y | | D | T | | N | | | | T | | |
| 65 | T | | L | | | | | L | | D | A | | K | | | | T | | |
| 67 | Y | | | | | | | G | | D | T | A | N | | | | T | V | R |
| 69 | T | | Q | | | | | L | | D | D | | K | D | | | T | | |
| 71 | Y | | L | | | | | L | | D | D | | K | D | | | | | |
| 72 | S | | R | | | | | G | | D | A | A | Q | K | | | T | | F |

| # | F 39 | H 40 | F 41 | A 55 | A 56 | H 57 | C 58 | I 99 | D 102 | S 189 | S 190 | G' 191 | M 192 | G 193 | D 194 | S 195 | V 213 | S 214 | W 215 |
|---|---|---|---|---|---|---|---|---|---|---|---|---|---|---|---|---|---|---|---|
| 75 |  |  | R |  |  |  |  |  |  |  |  |  |  |  |  |  |  |  |  |
| 77 | R |  | S |  |  |  |  | M |  | D | A |  | Q |  |  |  |  |  |  |
| 78 | K | K | Y |  |  |  |  | G |  | D |  | Y | Q |  |  |  |  |  | Y |
| 79 | K |  | H |  |  |  |  | N |  | A | P |  | E | N | E |  |  |  |  |
| 80 | K | K | Y |  |  |  |  | G |  | G | T | Y | R |  |  |  | G | T | Y |
| 81 | Y/M |  |  |  |  |  |  | T |  | A | P |  | E | R | E |  |  |  |  |
| 82 | S |  |  |  | G |  |  | L |  | M | L |  | A |  | N |  |  |  |  |
| 83 | Y |  |  |  |  |  |  | L |  | D |  |  | Q | R |  |  | G |  |  |
| 84 | Y |  |  |  |  |  |  | L |  | D |  |  | Q |  |  |  |  |  |  |
| 85 | S |  |  |  |  |  |  | L |  | D |  |  | Q |  |  |  |  |  |  |
| 86 | Y |  |  |  |  |  |  | T |  | D |  |  | Q | R |  |  |  |  |  |
| 88 | Y |  |  |  |  |  |  | T |  | D |  |  | K |  |  |  | G | T |  |
| 89 | Y |  |  |  |  |  |  | L |  | D |  |  | K | R |  |  |  |  |  |
| 90 | Y |  |  |  |  |  |  |  |  | D | T |  | Q |  |  |  |  |  |  |
| 93 | S |  |  |  | G |  |  | L |  | D |  |  | Q | R |  |  |  |  |  |
| 96 | Y |  | T |  |  |  |  | G/E |  | D |  |  | Q |  |  |  | T |  |  |
| 97 | Y | T | I |  |  |  |  | L |  | D |  |  | Q |  |  |  |  |  | F |
| 98 | K |  |  |  |  |  |  | R |  | D |  |  | N |  |  |  | T |  |  |
| 99 | S |  |  |  |  |  |  | L |  | D |  |  | Q |  |  |  |  |  |  |
| 100 |  |  |  |  |  |  |  |  |  |  |  |  |  |  |  |  |  |  |  |

FIG. 16A4

FIG. 16B1
IDENTIFICATION OF SEQUENCES COMPARED TO CHPEPZ

1. CHYMOTRYPSINOGEN B (EC 3.4.21.1)
2. CHYMOTRYPSINOGEN (EC 3.4.21.1) B PRECURSOR-BOVINE
3. CHYMOTRYPSINOGEN B PRECURSOR (EC 3.4.21.1)
4. CHYMOTRYPSINOGEN B PRECURSOR (EC 3.4.21.1)
5. CHYMOTRYPSINOGEN (EC 3.4.21.1) B PRECURSOR-HUMAN
6. CHYMOTRYPSINOGEN (EC 3.4.21.1) B PRECURSOR-RAT
7. CHYMOTRYPSINOGEN A (EC 3.4.21.1)
8. CHYMOTRYPSINOGEN (EC 3.4.21.1) A PRECURSOR-BOVINE
9. CHYMOTRYPSINOGEN 2 PRECURSOR (EC 3.4.21.1)
10. CHYMOTRYPSINOGEN (EC 3.4.21.1) 2 PRECURSOR-DOG
11. PLASMIN (EC 3.4.21.7) -PIG
12. PLASMINOGEN (EC 3.4.21.7) (FRAGMENT)
13. PLASMINOGEN (EC 3.4.21.7) (FRAGMENT)
14. PLASMIN (EC 3.4.21.7) PRECURSOR-HUMAN
15. PLASMINOGEN PRECURSOR (EC 3.4.21.7)
16. PLASMIN (EC 3.4.21.7) PRECURSOR-HUMAN
17. PLASMIN (EC 3.4.21.7) PRECURSOR-HUMAN
18. PLASMIN (EC 3.4.21.7) -SHEEP
19. PLASMINOGEN (EC 3.4.21.7)
20. PLASMIN (EC 3.4.21.7) -PIG (FRAGMENT)
21. PLASMINOGEN PRECURSOR (EC 3.4.21.7)
22. PLASMIN (EC 3.4.21.7) -RHESUS MACAQUE
23. PLASMIN (EC 3.4.21.7) PRECURSOR-RHESUS MACAQUE
24. APOLIPOPROTEIN (a) -RHESUS MACAQUE (FRAGMENT)
25. APOLIPOPROTEIN (a) -RHESUS MACAQUE (FRAGMENT)
26. APOLIPOPROTEIN (a) -(EC 3.4.21.-) (APO(A)) (LP(A))
27. TRYPSINOGEN II, ANIONIC PRECURSOR (EC 3.4.21.4)
28. PLASMINOGEN (EC 3.4.21.7)
29. PLASMINOGEN PRECURSOR-MOUSE
30. TRYPSIN-RELATED PROTEIN - AFRICAN MALARIA MOSQUITO
31. TRYPSIN (EC 3.4.21.4) II PRECURSOR-RAT
32. PLASMIN (EC 3.4.21.7) -BOVINE
33. PLASMINOGEN PRECURSOR (EC 3.4.21.7)
34. TRYPSIN (EC 3.4.21.7) PRECURSOR - AFRICAN MALARIA
35. TRYPSIN 1 PRECURSOR (EC 3.4.21.4)
36. TRYPSIN 3A1 PRECURSOR (EC 3.4.21.4)
37. TRYPSIN-LIKE PROTEINASE (EC 3.4.21.-) 3A1 PRECURSOR
38. TRYPSIN (EC 3.4.21.4) PRECURSOR-MOUSE
39. TRYPSINOGEN PRECURSOR (EC 3.4.21.4)
40. HEPATOCYTE GROWTH FACTOR HOMOLOG PRECURSOR-MOUSE
41. TRYPSIN 4 PRECURSOR (EC 3.4.21.4)
42. TRYPSIN (EC 3.4.21.4) PRECURSOR, CATIONIC-RAT
43. TRYPSINOGEN, ANIONIC PRECURSOR (EC 3.4.21.4)
44. HEPATOCYTE GROWTH FACTOR-LIKE PROTEIN PRECURSOR
45. HEPATOCYTE GROWTH FACTOR HOMOLOG PRECURSOR-HUMAN
46. TRYPSIN 7 PRECURSOR (EC 3.4.21.4)
47. TRYPSIN PRECURSOR (EC 3.4.21.4)
48. TRYPSINOGEN III, CATIONIC PRECURSOR (EC 3.4.21.4)
49. HEPATOCYTE GROWTH FACTOR-LIKE PROTEIN PRECURSOR
50. TRYPSIN (EC 3.4.21.4) PRECURSOR, ANIONIC-DOG

FIG. 16B2

51. TRYPSIN (EC 3.4.21.4) PRECURSOR, PANCREATIC
52. TRYPSIN-LIKE PROTEINASE (EC 3.4.21.-) PRECURSOR
53. TRYPSIN-LIKE PROTEINASE (EC 3.4.21.-) 5GI PRECURSOR
54. TRYPSIN  ALPHA PRECURSOR (EC 3.4.21.4)
55. PROTEINASE - SILKWORM
56. TRYPSIN 5G1 PRECURSOR (EC 3.4.21.4) (FRAGMENT)
57. COAGULATION FACTOR XIa (EC 3.4.21.27) PRECURSOR
58. TRYPSIN 3 PRECURSOR (EC 3.4.21.4)
59. COAGULATION FACTOR XI PRECURSOR (EC 3.4.21.27)
60. PLASMA KALLIKREIN PRECURSOR (EC 3.4.21.34)
61. PLASMA KALLIKREIN PRECURSOR (EC 3.4.21.34)
62. PLASMA KALLIKREIN (EC 3.4.21.34) PRECURSOR- MOUSE
63. COAGULATION FACTOR Xa (EC 3.4.21.6) PRECURSOR - HUMAN
64. CHYMOTRYPSIN 1 - PENAEID SHRIMP (PENAEUS VANAMEII)
65. PLASMA KALLIKREIN PRECURSOR (EC 3.4.21.34)
66. CHYMOTRYPSIN 1 PRECURSOR - PENAEID SHRIMP
67. CHYMOTRYPSIN 1 PRECURSOR (EC 3.4.21.1)
68. PLASMA KALLIKREIN  (EC 3.4.21.34) PRECURSOR - RAT
69. TRYPSINOGEN IV PRECURSOR (EC 3.4.21.4) (PRETRYPSIN)
70. TRYPSIN (EC 3.4.21.4) IV PRECURSOR - RAT
71. PLASMA KALLIKREIN (EC 3.4.21.34) PRECURSOR - HUMAN
72. TRYPSIN (EC 3.4.21.4) PRECURSOR - AFRICAN MALARIA
73. EBNA-1 NUCLEAR PROTEIN
74. TRYPSIN-RELATED PROTEIN - AFRICAN MALARIA MOSQUITO
75. TRYPSIN 2 PRECURSOR (EC 3.4.21.4)
76. PROBABLE NUCLEAR ANTIGEN - HUMAN HERPESVIRUS 4
77. TRYPSIN BETA PRECURSOR (EC 3.4.21.4)
78. GRANZYME G PRECURSOR (EC 3.4.21.-)
79. TRYPSIN 6 PRECURSOR (EC 3.4.21.4)
80. CYTOTOXIC T-LYMPHOCYTE PROTEINASE (EC 3.4.21.-)
81. ALPHA-TRYPTASE PRECURSOR (EC 3.4.21.59)
82. TRYPSINOGEN IVA PRECURSOR (EC 3.4.21.4)
83. TRYPSINOGEN I PRECURSOR (EC 3.4.21.4)
84. TRYPSIN (EC 3.4.21.4) I PRECURSOR - RAT
85. TRYPSIN (EC 3.4.21.4) TRYPSINOGEN IV a-FORM-HUMAN
86. TRYPTASE (EC 3.4.21.4 ) PRECURSOR - HUMAN
87. TRYPSIN PRECURSOR (EC 3.4.21.4)
88. TRYPTASE (EC 3.4.21.4) ALPHA PRECURSOR - HUMAN
89. TRYPSINOGEN I, ANIONIC PRECURSOR (EC 3.4.21.4)
90. TRYPSIN (EC 3.4.21.4) PRECURSOR, CATIONIC - DOG
91. MUCIN, SUBMAXILLARY - PIG (FRAGMENT)
92. GRANZYME A PRECURSOR (EC 3.4.21.-)
93. TRYPSINOGEN, CATIONIC PRECURSOR (EC 3.4.21.4)
94. PERIOD CLOCK PROTEIN - MOUSE (FRAGMENT)
95. PERIOD CLOCK PROTEIN (FRAGMENT)
96. TRYPSIN (EC 3.4.21.4) IV.b PRECURSOR - HUMAN
97. ACROSIN (EC 3.4.21.10), SPERM - PIG
98. TRYPSINOGEN II PRECURSOR (EC 3.4.21.4)
99. TRYPSIN-LIKE SERINE PROTEINASE (EC 3.4.21.4)
100. TRYPSIN (EC 3.4.21.4) PRECURSOR - PIG

QUERY SEQUENCE — LYSOZYME (EC 3.2.1.17) C2 — BOVINE
PEPTIDE SEQUENCE ACTIVE SEQUENCE ACTIVE SITE RESIDUES/SUBSTITUTIONS

| # | F 34 | E 35 | S 36 | N 37 | T 43 | N 44 | R 45 | N 46 | D 52 | L 56 | Q 57 | I 58 | N 59 | W 62 | W 63 | I 98 | D 101 | G 102 | D 103 | A 107 | W 108 | V 109 | A 110 | R 114 |
|---|---|---|---|---|---|---|---|---|---|---|---|---|---|---|---|---|---|---|---|---|---|---|---|---|
| 1 | W |  |  | S |  |  | Y |  |  | F |  |  |  |  |  |  | S | E | Q |  |  |  |  | H |
| 2 | W |  |  | S |  |  | Y |  |  | F |  |  |  |  |  |  | S | E | Q |  |  |  |  | H |
| 3 | W |  |  | S |  |  | Y |  |  | F |  |  |  |  |  |  | S | E | Q |  |  |  |  | H |
| 4 | W |  |  | S |  |  | Y |  |  | F |  |  |  |  |  |  | S | E | Q |  |  |  |  | H |
| 5 | W |  |  | S |  |  | Y |  |  | F |  |  |  |  |  |  | S | E | Q |  |  |  |  | H |
| 6 | W |  |  | S |  |  | Y |  |  | F |  |  |  |  |  |  | S | E | Q |  |  |  |  | H |
| 7 | W |  |  | G |  |  | Y |  |  | F |  |  |  |  |  |  | P | E | Q |  |  |  |  | H |
| 8 | W |  |  | S |  |  | Y |  |  | F |  |  |  |  |  |  | S | E | Q |  |  |  |  | H |
| 9 | W |  |  | S |  |  | Y |  |  | F |  |  |  |  |  |  | S | E | Q |  |  |  |  | H |
| 10 | W |  |  | S |  |  | Y |  |  | F |  |  |  |  |  |  | S | E | Q |  |  |  |  | H |
| 11 | W |  |  | S |  |  | Y |  |  | F |  |  |  |  |  |  | S | E | Q |  |  |  |  | H |
| 12 | W |  |  | S |  |  | Y |  |  | F |  |  |  |  |  |  | S | E | Q |  |  |  |  | H |
| 13 | W |  |  | S |  |  | Y |  |  | F |  |  |  |  |  |  | S | E | Q |  |  |  |  | H |
| 14 | W |  |  | G |  |  | Y |  |  | F |  |  |  |  |  |  | S | E | Q |  |  |  |  | H |
| 15 | W |  |  | S |  |  | Y |  |  | F |  |  |  |  |  |  | S | E | Q |  |  |  |  | H |
| 16 | W |  |  | S |  |  | Y |  |  | F |  |  |  | Y |  | V | R | E | Q |  |  |  |  | H |
| 17 | W |  |  | S |  |  | Y |  |  | F |  |  |  | Y |  | V | R | P | Q |  |  |  |  | H |
| 18 | W |  |  | S |  |  | Y |  |  | F |  |  |  | Y |  | V | R | P | Q |  |  |  |  | H |
| 19 | W |  |  | S |  |  | Y |  |  | F |  |  |  | Y |  | V |  | P | Q |  |  |  |  | H |

FIG. 17A1

| # | F 34 | E 35 | S 36 | N 37 | T 43 | N 44 | R 45 | N 46 | D 52 | L 56 | Q 57 | I 58 | N 59 | W 62 | W 63 | I 98 | D 101 | D G 102 | D 103 | A 107 | W 108 | V 109 | A 110 | A R 114 |
|---|---|---|---|---|---|---|---|---|---|---|---|---|---|---|---|---|---|---|---|---|---|---|---|---|
| 20 | W |  |  | D |  |  | Y |  |  | F |  |  |  |  |  |  |  |  | Q |  |  |  |  | H |
| 21 | W |  |  | S |  |  | Y |  |  | F |  |  |  |  | Y |  | V |  | P | Q |  |  |  |  | H |
| 22 | W |  |  |  |  |  | Y |  |  | F |  |  |  |  |  |  |  |  | P | Q |  |  |  |  | H |
| 23 | W |  |  | S |  |  | Y |  |  | F |  |  |  |  |  |  | V |  | P |  |  |  |  |  | H |
| 24 | W |  |  |  |  |  | Y |  |  | F |  |  |  |  | Y |  | V |  |  |  |  |  |  |  | H |
| 25 | W |  |  | D |  |  | Y |  |  |  |  |  |  |  |  |  |  |  |  |  |  |  |  |  | H |
| 26 | W |  |  |  |  |  | Y |  |  | F |  |  |  |  | Y |  |  |  | P | Q |  |  |  |  | H |
| 27 | W |  |  | G |  |  | Y |  |  | F |  |  |  |  | Y |  | V |  | P | Q |  |  |  |  | H |
| 28 | W |  |  | G |  |  | Y |  |  | F |  |  |  |  | Y |  | V |  | P | Q |  |  |  |  | R |
| 29 | W |  |  | G |  |  | Y |  |  | F |  |  |  |  | Y |  | V |  | P | Q |  |  |  |  | R |
| 30 | W |  |  | G |  |  | Y |  |  | F |  |  |  |  | Y |  | V |  | P | Q |  |  |  |  | R |
| 31 | W |  |  | G |  |  | Y |  |  | F |  |  |  |  | Y |  | V |  | P | Q |  |  |  |  | R |
| 32 | W |  |  |  |  |  | Y |  |  | F |  |  |  |  | Y |  | V |  | P | Q |  |  |  |  | H |
| 33 | W |  |  |  |  |  | Y |  |  | F |  |  |  |  | Y |  | V |  | P | Q |  |  |  |  | H |
| 34 | W |  |  | G |  |  | Y |  |  | F |  |  |  |  | Y |  | V |  | P | Q |  |  |  |  | R |
| 35 | W |  |  | G |  |  | Y |  |  | F |  |  |  |  | Y |  | V |  | P | Q |  |  |  |  | R |
| 36 | H |  |  |  |  |  | Y |  |  | F |  |  |  |  | Y |  | V |  | P | Q |  |  |  |  | Q |
| 37 | H |  |  |  |  |  | Y |  |  | F |  |  |  |  | Y |  | V |  | P | Q |  |  |  |  | H |
| 38 | H |  |  |  |  |  | Y |  |  | F |  |  |  |  | Y |  | V |  | P | Q |  |  |  |  | H |

| # | F 34 | E 35 | S 36 | N 37 | T 43 | N 44 | R 45 | N 46 | D 52 | L 56 | Q 57 | I 58 | N 59 | W 62 | W 63 | I 98 | D 101 | G 102 | D 103 | A 107 | W 108 | V 109 | A 110 | R 114 |
|---|---|---|---|---|---|---|---|---|---|---|---|---|---|---|---|---|---|---|---|---|---|---|---|---|
| 39 | H | | | | | | | | | | | | | | | | | | Q | | | | | Q |
| 40 | W | | | D | I | | Y | | | F | | | | Y | | V | | P | Q | | | | | H |
| 41 | H | | | | | | | | | F | | | | Y | | V | | P | Q | | | | | H |
| 42 | W | | | D | I | | Y | D | | F | | | | Y | | V | | P | Q | | | | | H |
| 43 | W | | | D | I | | H | | | F | | | | Y | | V | | P | Q | | | | | H |
| 44 | H | | | | | | Y | D | | F | | | | Y | | V | | P | L | | | | | H |
| 45 | W | | | S | | | | | | F | | | | Y | | V | | P | Q | | | | | H |
| 46 | | | | | | | | | | | | | | | | | | P | N | | | | | |
| 47 | | | | | | | | | | | | | | | | | | | B | | | | | |
| 48 | | | | | | | | | | | | | | | | | | | N | | | | | H |
| 49 | | | | | | | | | | | | | | | | | | R | N | | | | | |
| 50 | Y | | | | | | | | | | | E | | | | | | R | | | | | | |
| 51 | Y | | | | | | | | | | | | | | | | | | N | | | | | |
| 52 | Y | | | S | | | | | | | | E | | | | | | | | | | | | |
| 53 | | | | S | | | | | | | | | | | | | | | N | | | | | |
| 54 | Y | | | | | | | | | | | | | | | | | | | | | | | |
| 55 | Y | | | | | | | | | | | | | | | | | R | N | | | | | |
| 56 | | | | | | | | | | | | | | | | | | | N | | | | | |
| 57 | | | | | | | | | | | | | | | | | | | N | | | | | |

FIG. 17A4

| # | F 34 | E 35 | S 36 | N 37 | T 43 | N 44 | R 45 | N 46 | D 52 | L 56 | Q 57 | I 58 | N 59 | W 62 | W 63 | I 98 | D 101 | G 102 | D 103 | A 107 | W 108 | V 109 | A 110 | R 114 |
|---|---|---|---|---|---|---|---|---|---|---|---|---|---|---|---|---|---|---|---|---|---|---|---|---|
| 58 | | | | | | | | | | | | | | | | | | | B | | | | | |
| 59 | | | | | | | | | | | | | | | | | | R | N | | | | | |
| 60 | Y | | | | | | | | | | | | | | | | | | | | | | | H |
| 61 | | | | | | | | | | | | | | | | | | | | | | | | H |
| 62 | | | | | | | | | | | | | | | | | G | G | N | | | | | |
| 63 | | | | | | | | | | | | | | | | | | | | | | | | H |
| 64 | | | | | | | | | | | | | | | | | | | | | | | | H |
| 65 | Y | | | G | | | | | | | | | | | | | | | | | | | | |
| 66 | Y | | | G | | | | | | | | | | | | | | | | | | | | |
| 67 | | | | | | | | | | | | | | | | | | | N | | | | | |
| 68 | | | | | | | | | | | | | | | | | | | N | | | | | |
| 69 | | | | | | | | | | | | | | | | | | | N | | | | | |
| 70 | | | | | | | | | | | | | | | | | | | N | | | | | |
| 71 | | | | | | | | | | | | | | | | | | | N | | | | | |
| 72 | | | | | | | | | | | | | | | | | | V | H | | | | | |
| 73 | | | | | | | | | | | | | | | | | | | | | | | | |
| 74 | | | | | | | | | | | | | | | | | | | N | | | | | H |
| 75 | | | | | | | | | | | | | | | | V | | | B | | | | | H |
| 76 | Y | | | | F | | G | K | | F | | L | | | | | | P | K | | | K | | H |

FIG. 17A5

| # | F 34 | E 35 | S 36 | N 37 | T 43 | N 44 | R 45 | N 46 | D 52 | L 56 | Q 57 | I 58 | N 59 | W 62 | W 63 | I 98 | D 101 | G 102 | D 103 | A 107 | W 108 | V 109 | A 110 | R 114 |
|---|---|---|---|---|---|---|---|---|---|---|---|---|---|---|---|---|---|---|---|---|---|---|---|---|
| 77 | Y |  |  |  | F |  | G | K |  | F |  | L |  |  |  | V |  | P | K |  |  | K |  | H |
| 78 | Y |  |  |  | F |  | G | K |  | F |  | L |  |  |  | V |  | P | K |  |  | K |  | H |
| 79 | Y |  |  |  | F |  | G | K |  | F |  | L |  |  |  | V |  | P | K |  |  | K |  | H |
| 80 | H |  |  | G | F |  | N |  |  | F |  |  |  | Y |  |  | E | A | R |  |  |  |  | Y |
| 81 | H |  |  | G | F |  | N |  |  | F |  |  |  | Y |  |  | E | A | R | P |  |  |  | Y |
| 82 | W |  |  | S |  |  | Y |  |  | F |  |  |  |  |  |  | E | Q | G | P |  |  |  | H |
| 83 | H |  |  | S |  |  | H |  |  |  |  |  |  | Y |  |  | E | A | K |  |  |  |  | K |
| 90 | H |  |  | G | L |  | Y | Y | - | F |  |  |  | Y |  |  | E | P | K | P |  | E |  | F |
| 91 | H |  |  | G | L |  | Y | Y | - | F |  |  |  | Y |  |  | E | P | K |  |  | E |  | F |
| 97 | H |  |  | S | A |  | S |  |  | F |  |  |  | Y |  |  | Q | Q | G |  |  | S | T | C |
| 98 | H |  |  | S | V | G | P | A |  | F |  |  |  | Y |  |  | Q | Q | G |  |  | S | T | C |

FIG. 17B1

IDENTIFICATION OF SEQUENCES COMPARED TO LYPEPZ

1. LYSOZYME (EC 3.2.1.17) c2-BOVINE
2. LYSOZYME (EC 3.2.1.17) 2b PRECURSOR-BOVINE
3. LYSOZYME (EC 3.2.1.17) 1 PRECURSOR-BOVINE
4. LYSOZYME (EC 3.2.1.17) 2a PRECURSOR-BOVINE
5. LYSOZYME (EC 3.2.1.17) 2c PRECURSOR-BOVINE
6. LYSOZYME C 1a TO 4b (EC 3.2.1.17)
7. LYSOZYME (EC 3.2.1.17) 2 - CHITAL
8. LYSOZYME (EC 3.2.1.17) 3 - SHEEP
9. LYSOZYME (EC 3.2.1.17) 2 - SHEEP
10. LYSOZYME (EC 3.2.1.17) 1 - SHEEP
11. LYSOZYME C PRECURSOR (EC 3.2.1.17)
12. LYSOZYME (EC 3.2.1.17) - 3 PRECURSOR - BOVINE
13. LYSOZYME C 1 AND 2 (EC 3.2.1.17)
14. LYSOZYME (EC 3.2.1.17) - RED DEER
15. LYSOZYME (EC 3.2.1.17) - CHITAL
16. LYSOZYME (EC 3.2.1.17) - HANUMAN LANGUR
17. LYSOZYME c PRECURSOR (EC 3.2.1.17)
18. LYSOZYME c (EC 3.2.1.17)
19. LYSOZYME (EC 3.2.1.17) - RABBIT
20. LYSOZYME c (EC 3.2.1.17)
21. LYSOZYME c, KIDNEY (EC 3.2.1.17)
22. LYSOZYME c, KIDNEY (EC 3.2.1.17)
23. LYSOZYME (EC 3.2.1.17) - SHEEP
24. LYSOZYME (EC 3.2.1.17) - BOVINE
25. LYSOZYME (EC 3.2.1.17) - BABOON
26. LYSOZYME c PRECURSOR (EC 3.2.1.17)
27. LYSOZYME c PRECURSOR (EC 3.2.1.17)
28. LYSOZYME (EC 3.2.1.17) PRECURSOR - HUMAN
29. LYSOZYME (EC 3.2.1.17) - HUMAN
30. LYSOZYME c PRECURSOR (EC 3.2.1.17)
31. LYSOZYME (EC 3.2.1.17) - HUMAN
32. LYSOZYME C-3 (EC 3.2.1.17)
33. LYSOZYME (EC 3.2.1.17) - RED DEER
34. LYSOZYME (EC 3.2.1.17) PRECURSOR - HUMAN
35. LYSOZYME (EC 3.2.1.17) PRECURSOR - HUMAN
36. LYSOZYME C, TYPE P PRECURSOR (EC 3.2.1.17)
37. LYSOZYME C, TYPE M PRECURSOR (EC 3.2.1.17)
38. LYSOZYME (EC 3.2.1.17) M PRECURSOR - MOUSE
39. LYSOZYME (EC 3.2.1.17) P PRECURSOR - MOUSE
40. LYSOZYME C-1 (EC 3.2.1.17)
41. LYSOZYME (EC 3.2.1.17) - RAT
42. LYSOZYME (EC 3.2.1.17) - RED DEER
43. LYSOZYME C-2 (EC 3.2.1.17)
44. LYSOZYME C (EC 3.2.1.17)
45. LYSOZYME C II PRECURSOR (EC 3.2.1.17)
46. LYSOZYME (EC 3.2.1.17) c - COMMON BOBWHITE
47. LYSOZYME (EC 3.2.1.17) - LADY AMHERST'S PHEASANT
48. LYSOZYME C (EC 3.2.1.17)
49. LYSOZYME C (EC 3.2.1.17)
50. LYSOZYME C (EC 3.2.1.17)

FIG. 17B2

51. LYSOZYME C (EC 3.2.1.17)
52. LYSOZYME (EC 3.2.1.17) c III - DUCK
53. LYSOZYME C (EC 3.2.1.17)
54. LYSOZYME C-3 (EC 3.2.1.17)
55. LYSOZYME (EC 3.2.1.17) c - KALIJ PHEASANT
56. LYSOZYME (EC 3.2.1.17) - REEVE'S PHEASANT
57. LYSOZYME (EC 3.2.1.17) - GOLDEN PHEASANT
58. LYSOZYME (EC 3.2.1.17)
59. LYSOZYME (EC 3.2.1.17) c - INDIAN PEAFOWL
60. LYSOZYME (EC 3.2.1.17) c - PLAIN CHACHALACA
61. LYSOZYME (EC 3.2.1.17) c PRECURSOR
62. LYSOZYME C PRECURSOR (EC 3.2.1.17)
63. LYSOZYME (EC 3.2.1.17) - GREEN PHEASANT
64. LYSOZYME C PRECURSOR (EC 3.2.1.17)
65. LYSOZYME C-1 PRECURSOR (EC 3.2.1.17)
66. LYSOZYME (EC 3.2.1.17) c - PRECURSOR - DUCK
67. LYSOZYME C PRECURSOR (EC 3.2.1.17)
68. LYSOZYME (EC 3.2.1.17) PRECURSOR - CHICKEN
69. LYSOZYME C (EC 3.2.1.17)
70. LYSOZYME (EC 3.2.1.17) c - CALIFORNIA QUAIL
71. LYSOZYME (EC 3.2.1.17) c PRECURSOR - CHICKEN
72. LYSOZYME (EC 3.2.1.17) c PRECURSOR - JAPANESE QUAIL
73. LYSOZYME C (EC 3.2.1.17) - CHICKEN
74. LYSOZYME C (EC 3.2.1.17)
75. LYSOZYME (EC 3.2.1.17) c - HELMETED GUINEAFOWL
76. LYSOZYME C (EC 3.2.1.17)
77. LYSOZYME (EC 3.2.1.17) c - DONKEY
78. LYSOZYME (EC 3.2.1.17) - HORSE
79. LYSOZYME C (EC 3.2.1.17)
80. LYSOZYME C (EC 3.2.1.17)
81. LYSOZYME (EC 3.2.1.17) c - PIGEON
82. LYSOAYME (EC 3.2.1.17) 2d PRECURSOR - BOVINE
83. LYSOZYME (EC 3.2.1.17) I - AUSTRALIAN ECHIDNA
84. LYSOZYME (EC 3.2.1.17) c PRECURSOR - JAPANESE QUAIL
85. LYSOZYME (EC 3.2.1.17) c PRECURSOR - TURKEY
86. LYSOZYME (EC 3.2.1.17)
87. ALPHA-LACTALBUMIN PRECURSOR - GOAT
88. ALPHA-LACTALBUMIN PRECURSOR
89. ALPHA-LACTALBUMIN PRECURSOR - SHEEP
90. ALPHA-LACTALBUMIN (LACTOSE SYNTHASE B PROTEIN)
91. ALPHA-LACTALBUMIN - DUCKBILL PLATYPUS
92. ALPHA-LACTALBUMIN PRECURSOR - GOAT
93. ALPHA-LACTALBUMIN PRECURSOR - GUINEA PIG
94. ALPHA-LACTALBUMIN PRECURSOR - (LACTOSE SYNTHASE B)
95. ALPHA-LACTALBUMIN PRECURSOR - GUINEA PIG
96. ALPHA-LACTALBUMIN PRECURSOR
97. LYSOZYME (EC 3.2.1.17) P PRECURSOR - FRUIT FLY
98. LYSOZYME P PRECURSOR (EC 3.2.1.17)
99. ALPHA-LACTALBUMIN PRECURSOR (VERSION 1) - RAT
100. ALPHA-LACTALBUMIN PRECURSOR

FIG. 18A1

QUERY SEQUENCE – RIBONUCLEASE A – BOVINE
PEPTIDE SEQUENCE ACTIVE SITE RESIDUES/SUBSTITUTIONS

| DATABASE NAME/CITE | K 7 | F 8 | Q 11 | H 12 | K 41 | P 42 | V 43 | N 44 | T 45 | E 111 | V 118 | H 119 | F 120 | D 121 | A 122 | S 123 |
|---|---|---|---|---|---|---|---|---|---|---|---|---|---|---|---|---|
| 3 | | | | | | | | | | | | | | | G | A |
| 4 | | | | | | | | | | | | | | | | |
| 5 | | | | | | | | | | G | | | | | | |
| 6 | | | | | | | | | | G | | | | | | |
| 7 | | | | | | | | | | D | | | | | | |
| 8 | | | | | | | | | | D | | | | | | T |
| 9 | | | | | | | | | | | | | | | | T |
| 10 | | | | | | | | | | | | | | | | T |
| 24 | | | | | | | | | | | | | Y | | | |
| 25 | | | | | | | | | | | | | Y | | | |
| 26 | | | | | | | | | | | | | Y | | | |
| 27 | | | | | | | | | | | | | Y | | | |
| 28 | | | | | | | | | | | | | Y | | | |
| 29 | | | | | | | | | | | | | | | | T |
| 30 | | | | | | | | | | | | | | | | |
| 31 | | | | | | | | | | | | | | | | |
| 32 | | | | X | | | | | | | | | | | | T |
| 33 | | | | | | | | | | | | | | | | |

| DATABASE NAME/CITE | K 7 | F 8 | Q 11 | H 12 | K 41 | P 42 | V 43 | N 44 | T 45 | E 111 | V 118 | H 119 | F 120 | D 121 | A 122 | S 123 |
|---|---|---|---|---|---|---|---|---|---|---|---|---|---|---|---|---|
| 34 | | | X | | | | | | | | | | | | | |
| 39 | | | Z | | | | | | | | | | | | | |
| 43 | | | | | | | | | | | | | | | | |
| 44 | | | | | | | | | | | | | | | N | |
| 45 | | | | | | | | | | G | | | | | N | |
| 46 | | | | | | | | | | | | | | | N | |
| 47 | | | | | | | | | | | | | | | N | |
| 48 | | | | | | | | | | | | | Y | | | |
| 49 | | | | | | | | | | | | | Y | | | |
| 50 | | | | | | | | | | | | | | | G | A |
| 81 | | | | | | S | | | | | | | | | | T |
| 83 | | | | | | S | | | | | | | | | | T |
| 87 | | | | | | | | | | | | | | D | | |
| 88 | | | | | | | | | | | | | | D | | |
| 91 | | | | | | | | | | | | | Y | | | |
| 92 | | | | | | | | | | | | | Y | | | |
| 99 | | | | | | | L | | | | | | | | | Y |
| 100 | | | | | | | | | | | | | | | | Y |

IDENTIFICATION OF SEQUENCES COMPARED TO RNPEPZ

1. RIBONUCLEASE PANCREATIC PRECURSOR
2. PANCREATIC RIBONUCLEASE
3. RIBONUCLEASE, BRAIN – BOVINE
4. RIBONUCLEASE, SEMINAL PRECURSOR (EC 3.1.27. 5)
5. SEMINAL RIBONUCLEASE (EC 3.1.27.5) PRECURSOR – BOVINE
6. PANCREATIC RIBONUCLEASE (EC 3.1.27.5) PRECURSOR
7. RIBONUCLEASE PANCREATIC PRECURSOR (EC 3.1.27.5)
8. PANCREATIC RIBONUCLEASE (EC 3.1.27.5) – MOUSE
9. PANCREATIC RIBONUCLEASE (EC 3.1.27.5) PRECURSOR
10. RIBONUCLEASE PANCREATIC PRECURSOR (EC 3.1.27.5)
11. PANCREATIC RIBONUCLEASE (EC 3.1.27.5) – BOVINE
12. PANCREATIC RIBONUCLEASE (EC 3.1.27.5) – BOVINE
13. PANCREATIC RIBONUCLEASE (EC 3.1.27.5)
14. PANCREATIC RIBONUCLEASE (EC 3.1.27.5) A – BOVINE
15. PANCREATIC RIBONUCLEASE (EC 3.1.27.5) – IMPALA
16. PANCREATIC RIBONUCLEASE (EC 3.1.27.5) – SHEEP
17. PANCREATIC RIBONUCLEAS (EC 3.1.27.5)
18. RIBONUCLEASE PANCREATIC (EC 3.1.27.5) (RNase 1)
19. RIBONUCLEASE – DOMESTIC WATER BUFFALO
20. RIBONUCLEASE PANCREATIC (EC 3.1.27.5) (RNase 1)
21. RIBONUCLEASE PANCREATIC (EC 3.1.27.5) (RNase 1)
22. PANCREATIC RIBONUCLEASE (EC 3.1.27.5) – GIRAFFE
23. PANCREATIC RIBONUCLEASE (EC 3.1.27.5)
24. RIBONUCLEASE PANCREATIC (EC 3.1.27.5) (RNase 1)
25. RIBONUCLEASE PANCREATIC (EC 3.1.27.5) (RNase 1)
26. RIBONUCLEASE PANCREATIC (EC 3.1.27.5) (RNase 1)
27. RIBONUCLEASE – DOMESTIC WATER BUFFALO
28. PANCREATIC RIBONUCLEASE (EC 3.1.27.5) – PRONGHORN
29. RIBONUCLEASE PANCREATIC PRECURSOR (EC 3.1.27.5)
30. PANCREATIC RIBONUCLEASE (EC 3.1.27.5) – REINDEER
31. RIBONUCLEASE PANCREATIC PRECURSOR (EC 3.1.27.5)
32. RIBONUCLEASE PANCREATIC (EC 3.1.27.5)
33. RIBONUCLEASE PANCREATIC (EC 3.1.27.5) (RNase 1)
34. RIBONUCLEASE – THOMSON'S GAZELLE
35. PANCREATIC RIBONUCLEASE (EC 3.1.27.5)
36. RIBONUCLEASE PANCREATIC (EC 3.1.27.5) (RNase 1)
37. PANCREATIC RIBONUCLEASE (EC 3.1.27.5) – FALLOW DEER
38. RIBONUCLEASE PANCREATIC (EC 3.1.27.5) (RNase 1)
39. RIBONUCLEASE PANCREATIC (EC 3.1.27.5) (RNase 1)
40. RIBONUCLEASE PANCREATIC (EC 3.1.27.5) (RNase 1)
41. RIBONUCLEASE PANCREATIC (EC 3.1.27.5) (RNase 1)
42. PANCREATIC RIBONUCLEASE (EC 3.1.27.5) – ROE DEER
43. SEMINAL RIBONUCLEASE (EC 3.1.27.5) – SYNTHETIC
44. PANCREATIC RIBONUCLEASE (EC 3.1.27.5) A – GUINEA PIG
45. RIBONUCLEASE PANCREATIC A (EC 3.1.27.5) (RNase 1A)
46. RIBONUCLEASE PANCREATIC (EC 3.1.27.5) (RNasse 1)
47. PANCREATIC RIBONUCLEASE (EC 3.1.27.5) – MINKE WHALE
48. PANCREATIC RIBONUCLEASE (EC 3.1.27.5) – HIPPOPOTAMUS
49. RIBONUCLEASE PANCREATIC (EC 3.1.27.5) (RNase 1)
50. PANCREATIC-TYPE RIBONUCLEASE (EC 3.1.27.5) BRb, br

FIG. 18B2

51. PANCREATIC RIBONUCLEASE (EC 3.1.27.5) PRECURSOR
52. RIBONUCLEASE PANCREATIC (EC 3.1.27.5) (RNase 1)
53. PANCREATIC RIBONUCLEASE PRECURSOR (EC 3.1.27.5)
54. PANCREATIC RIBONUCLEASE (EC 3.1.27.5)
55. RIBONUCLEASE PANCREATIC (EC 3.1.27.5) (RNase 1)
56. PANCREATIC RIBONUCLEASE (EC 3.1.27.5) − GOLDEN HAMSTER
57. PANCREATIC RIBONUCLEASE (EC 3.1.27.5), MINOR FORM
58. PANCREATIC RIBONUCLEASE (EC 3.1.27.5)
59. PANCREATIC RIBONUCLEASE (EC 3.1.27.5) − RED DEER
60. RIBONUCLEASE PANCREATIC (EC 3.1.27.5) (RNase 1)
61. PANCREATIC RIBONUCLEASE (EC 3.1.27.5) − HUMAN
62. RIBONUCLEASE PANCREATIC (EC 3.1.27.5) (RNase 1)
63. RIBONUCLEASE PANCREATIC (EC 3.1.27.5) (RNase 1)
64. RIBONUCLEASE PANCREATIC (EC 3.1.27.5) (RNase 1)
65. PANCREATIC RIBONUCLEASE (EC 3.1.27.5) − HUMAN
66. PANCREATIC RIBONUCLEASE (EC 3.1.27.5) − CAPYBARA
67. PANCREATIC RIBONUCLEASE (EC 3.1.27.5)
68. PANCREATIC RIBONUCLEASE (EC 3.1.27.5) − CASIRAGUA
69. PANCREATIC RIBONUCLEASE (EC 3.1.27.5) − HORSE
70. RIBONUCLEASE PANCREATIC (EC 3.1.27.5) (RNase 1)
71. PANCREATIC RIBONUCLEASE (EC 3.1.27.5) − PIG
72. RIBONUCLEASE PANCREATIC B (EC 3.1.27.5) (RNase IB)
73. PANCREATIC RIBONUCLEASE (EC 3.1.27.5) B − GUINEA PIG
74. PANCREATIC RIBONUCLEASE (EC 3.1.27.5) − NUTRIA
75. RIBONUCLEASE PANCREATIC (EC 3.1.27.5) (RNase 1)
76. RIBONUCLEASE PANCREATIC (EC 3.1.27.5) (RNase 1)
77. PANCREATIC RIBONUCLEASE (EC 3.1.27.5) − CHINCHILLA
78. RIBONUCLEASE PANCREATIC (EC 3.1.27.5) (RNase 1)
79. PANCREATIC RIBONUCLEASE (EC 3.1.27.5) − MUSKRAT
80. PANCREATIC RIBONUCLEASE (EC 3.1.27.5) − MOUSE
81. RIBONUCLEASE PANCREATIC (EC 3.1.27.5) (RNase 1)
82. RIBONUCLEASE PANCREATIC (EC 3.1.27.5) (RNase 1)
83. PANCREATIC RIBONUCLEASE (EC 3.1.27.5) − CUIS
84. PANCREATIC RIBONUCLEASE (EC 3.1.27.5) − GOAT
85. RIBONUCLEASE PANCREATIC (EC 3.1.27.5) (RNase 1)
86. PANCREATIC RIBONUCLEASE (EC 3.1.27.5)
87. RIBONUCLEASE PANCREATIC (EC 3.1.27.5) (RNase 1)
88. PANCREATIC RIBONUCLEASE (EC 3.1.27.5) − HANUMAN LANGUR
89. SUBTILISIN (EC 3.4.21.62) BPN' PRECURSOR
90. SUBTILISIN BPN' PRECURSOR (EC 3.4.21.62)
91. RIBONUCLEASE PANCREATIC (EC 3.1.27.5) (RNase 1)
92. PANCREATIC RIBONUCLEASE (EC 3.1.27.5)
93. SPORE COAT PROTEIN SP96 PRECURSOR − SLIME MOLD
94. SPORE COAT PROTEIN SP96
95. HYPOTHETICAL PROTEIN 4 (phaC2 3' REGION)
96. TRANSCRIPTIONAL REGULATORY PROTEIN ALGP
97. REGULATORY PROTEIN AlgR3 − PSEUDOMONAS AERUGINOSA
98. HYPOTHETICAL 34.4K PROTEIN − PSEUDOMONAS AERUGINOS
99. RIBONUCLEASE PANCREATIC (EC 3.1.27.5) (RNase 1)
100. PANCREATIC RIBONUCLEASE (EC 3.1.27.5) − RED KANGAR QUERY SEQUENCE - UROKINASE TYPE PLASMINOGEN ACTIVATOR - HUMAN
PEPTIDE SEQUENCE ACTIVE SITE RESIDUES/SUBSTITUTIONS

| # | T 28 | Y 29 | V 30 | A 44 | T 45 | H 46 | C 47 | L 92 | D 97 | D 192 | S 193 | C 194 | Q 195 | G 196 | D 197 | S 198 | V 216 | S 217 | W 218 |
|---|------|------|------|------|------|------|------|------|------|-------|-------|-------|-------|-------|-------|-------|-------|-------|-------|
| 1 | | | | | | | | | | | | | | | | | | | |
| 2 | | | | | | | | | | | | | | | | | | | |
| 3 | | | | | | | | | | | | | | | | | | | |
| 4 | | | | | | | | | | | | | | | | | | | |
| 5 | | | L | | | | | | | | | | | | | | | | |
| 6 | | | L | | | | | | | | | | | | | | | | |
| 7 | | | | | | | | | | | | | | | | | | | |
| 8 | S | F | K | | | | | | | | | | | | | | | | |
| 9 | S | F | K | | | | | | | | | | | | | | | | |
| 10 | S | F | K | | A | | | | | | | | | | | | | | |
| 11 | S | F | K | | A | | | | | | | | K | | | | | | |
| 12 | S | F | K | | A | | | | | | A | | K | | | | | | |
| 13 | S | F | K | | | | | | | | A | | K | | | | | | |
| 14 | | | | | | | | | | | | | | | | | | | |
| 15 | | | | | | | | G | | | | | | | | | | | |
| 16 | Q | F | L | | A | | | G | | | A | | K | | | | | | |
| 17 | Q | F | L | | A | | | G | | | A | | K | | | | | | |
| 18 | D | S | F | | A | | | N | | | A | | | | | | I | | |

| # | T 28 | Y 29 | V 30 | A 44 | T 45 | H 46 | C 47 | L 92 | D 97 | D 192 | S 193 | C 194 | Q 195 | G 196 | D 197 | S 198 | V 216 | S 217 | W 218 |
|---|---|---|---|---|---|---|---|---|---|---|---|---|---|---|---|---|---|---|---|
| 19 | H | S | F |  | A |  |  | V |  |  | A |  |  |  |  |  | I |  |  |
| 20 | H | S | F |  | A |  |  | V |  |  | A |  |  |  |  |  | I |  |  |
| 21 | S | N | F |  | A |  |  | S |  |  | A |  |  |  |  |  |  |  |  |
| 26 | K | L | A |  | A |  |  | S |  |  | A |  |  |  |  |  |  |  |  |
| 27 | K | L | A |  | A |  |  | S |  |  | A |  |  |  |  |  |  |  |  |
| 28 | K | L | A |  | A |  |  | S |  |  | A |  | E |  |  |  |  |  |  |
| 35 | K | H | F | T | A | A |  |  |  |  | A |  | E |  |  |  | T |  |  |
| 36 | A | Q | L |  | A |  |  | G |  |  | R |  | E |  |  |  |  |  |  |
| 37 | K | L | A |  | A |  |  | S |  |  | A |  | K |  |  | N |  |  |  |
| 38 | A | Q | L |  | A |  |  | G |  |  |  |  | E |  |  |  |  |  |  |
| 39 | K | H | F | T | A | A |  |  |  |  | R |  | K |  |  |  | T |  |  |
| 44 | K | L | A |  | A |  |  | S |  |  | A |  | D |  |  |  |  |  |  |
| 45 | K | L | A |  | A |  |  | S |  |  | A |  | D |  |  |  |  |  |  |
| 48 | K | L | A |  | A |  |  | S |  |  | A |  | D |  |  |  |  |  |  |
| 50 | K | L | A |  | A |  |  | S |  |  | A |  | D |  |  |  |  |  |  |
| 51 | K | L | A |  | A |  |  | S |  |  | A |  | D |  |  | N |  |  |  |
| 53 | R | H | L |  | A |  |  | S |  |  | A |  | K |  |  |  | T |  |  |
| 54 | R | H | L |  | A |  |  | S |  |  | A |  | K |  |  |  | T |  |  |

FIG. 19A3

| # | T 28 | Y 29 | V 30 | A 44 | T 45 | H 46 | C 47 | L 92 | D 97 | D 192 | S 193 | C 194 | Q 195 | G 196 | D 197 | S 198 | V 216 | S 217 | W 218 |
|---|---|---|---|---|---|---|---|---|---|---|---|---|---|---|---|---|---|---|---|
| 55 |   | H | L |   | A |   |   | S |   |   | A |   | K |   |   |   | T |   |   |
| 57 |   | H | L |   | A |   |   | S |   |   | A |   | K |   |   |   | T |   |   |
| 61 | N | H | M |   | A |   |   |   |   |   | A |   | K |   |   |   | T |   |   |
| 62 | Q | H | F |   | A |   |   |   |   |   |   |   |   |   |   |   | T |   |   |
| 63 | Q | H | F |   | A |   |   | S |   |   | A |   |   |   |   |   | T |   |   |
| 66 | N | H | M |   | A |   |   | S |   |   | A |   | K |   |   |   | T |   |   |
| 69 | A | H | L |   | A |   |   | I |   |   | A |   |   |   |   |   |   |   |   |
| 70 |   | H | L |   | A |   |   | I |   |   | A |   |   |   |   |   |   |   |   |
| 71 |   | H | L |   | A |   |   | I |   |   | A |   |   |   |   |   |   |   |   |
| 72 |   | H | L |   | A |   |   | S |   |   |   |   |   |   |   |   |   |   |   |
| 73 |   | H | F |   | A |   |   | S |   |   |   |   |   |   |   |   |   |   |   |
| 74 | G | H | F |   | K |   |   | A |   |   | A |   | K |   |   |   | T |   |   |
| 82 | M | H | F |   | A |   |   | A |   |   |   |   |   |   |   |   | T |   |   |
| 83 | M | H | F |   | A |   |   | A/S |   |   | A |   |   |   |   |   | T |   |   |
| 84 | R | H | L |   | A |   |   | A |   |   |   |   | K |   |   |   | T |   |   |
| 86 | M | H | F |   | A |   |   | A/S |   |   | A |   |   |   |   |   | T |   |   |
| 87 | R | H | L |   | A |   |   | A/S |   |   | A |   |   |   |   |   |   |   |   |
| 91 | E | G | F |   | A |   |   | Y |   |   |   |   |   |   |   |   |   |   |   |

FIG. 19A4

| # | T 28 | Y 29 | V 30 | A 44 | T 45 | H 46 | C 47 | L 92 | D 97 | D 192 | S 193 | C 194 | Q 195 | G 196 | D 197 | S 198 | V 216 | S 217 | W 218 |
|---|---|---|---|---|---|---|---|---|---|---|---|---|---|---|---|---|---|---|---|
| 92 | M | H | F |  | A |  |  | T |  |  |  |  |  |  |  |  | T |  |  |
| 93 | E | G | F |  | A |  |  | Y |  |  | A |  |  |  |  |  |  |  |  |
| 94 | M | H | F |  | A |  |  | T |  |  |  |  |  |  |  |  | T |  |  |
| 95 | M | H | F |  | A |  |  | T |  |  |  |  |  |  |  |  | T |  |  |
| 96 | M | H | F |  | A |  |  | S |  |  |  |  |  |  |  |  | T |  |  |
| 97 | M | H | F |  | A |  |  | T |  |  |  |  |  |  |  |  | T |  |  |
| 100 | R | H | F |  | A |  |  | S |  |  |  |  |  |  |  |  |  |  |  |
| TPA | R | F | L |  | A |  | Y |  |  | A |  |  |  |  |  |  | I |  |  |

FIG. 19B1

IDENTIFICATION OF SEQUENCES COMPARED TO UKPEPZ

1. UROKINASE-TYPE PLASMINOGEN ACTIVATOR
2. U-PLASMINOGEN ACTIVATOR (EC 3.4.21.73) PRECURSOR
3. U-PLASMINOGEN ACTIVATOR (EC 3.4.21.73) PRECURSOR
4. UROKINASE-TYPE PLASMINOGEN ACTIVATOR PRECURSOR
5. U-PLASMINOGEN ACTIVATOR (EC 3.4.21.73) PRECURSOR
6. U-PLASMINOGEN ACTIVATOR (EC 3.4.21.73) PRECURSOR
7. UROKINASE-TYPE PLASMINOGEN ACTIVATOR PRECURSOR
8. UROKINASE-TYPE PLASMINOGEN ACTIVATOR PRECURSOR
9. U-PLASMINOGEN ACTIVATOR (EC 3.4.21.73) – RAT
10. U-PLASMINOGEN ACTIVATOR (EC 3.4.21.73) – RAT
11. UROKINASE-TYPE PLASMINOGEN ACTIVATOR PRECURSOR
12. U-PLASMINOGEN ACTIVATOR (EC 3.4.21.73) PRECURSOR
13. U-PLASMINOGEN ACTIVATOR (EC 3.4.21.73) PRECURSOR
14. U-PLASMINOGEN ACTIVATOR (EC 3.4.21.73) PRECURSOR
15. UROKINASE-TYPE PLASMINOGEN ACTIVATOR PRECURSOR
16. UROKINASE-TYPE PLASMINOGEN ACTIVATOR PRECURSOR
17. U-PLASMINOGEN ACTIVATOR (EC 3.4.21.73) PRECURSOR
18. HEPATOCYTE GROWTH FACTOR ACTIVATOR – HGF ACTIVATOR
19. COAGULATION FACTOR XII PRECURSOR (EC 3.4.21.38)
20. COAGULATION FACTOR XIIa (EC 3.4.21.38) PRECURSOR
21. COAGULATION FACTOR XIIa (EC 3.4.21.38) – GUINEA PIG
22. TISSUE PLASMINOGEN ACTIVATOR PRECURSOR
23. T-PLASMINOGEN ACTIVATOR (EC 3.4.21.68) PRECURSOR
24. T-PLASMINOGEN ACTIVATOR (EC 3.4.21.68) PRECURSOR
25. PERIOD CLOCK PROTEIN – MOUSE (FRAGMENT)
26. PROTEIN C (ACTIVATED) (EC 3.4.21.69) PRECURSOR
27. PROTEIN C (ACTIVATED) (EC 3.4.21.69) PRECURSOR
28. PREOTEIN C PRECURSOR (EC 3.4.21.69) (AUTOPROTHROMBIN)
29. PERIOD CLOCK PROTEIN (FRAGMENT)
30. T-PLASMINOGEN ACTIVATOR (EC 3.4.21.68) PRECURSOR
31. T-PLASMINOGEN ACTIVATOR (EC 3.4.21.68) – RAT
32. TISSUE PLASMINOGEN ACTIVATOR PRECURSOR
33. T-PLASMINOGEN ACTIVATOR (EC 3.4.21.68) PRECURSOR
34. TISSUE PLASMINOGEN ACTIVATOR PRECURSOR
35. APOLIPROPROTEIN(a) – RHESUS MACAQUE (FRAGMENT)
36. COAGULATION FACTOR VII PRECURSOR – HUMAN
37. PROTEIN C – HUMAN
38. COAGULATION FACTOR VII PRECURSOR (EC 3.4.21.21)
39. APOLIPOPROTEIN (A) (EC 3.4.21.-) (APO(A)) (LP(A))
40. ELASTIN – CHICKEN (FRAGMENT)
41. ELASTIN PRECURSOR – CHICKEN (FRAGMENT)
42. ELASTIN PRECURSOR (FRAGMENT)
43. PARACRYSTALLINE SURFACE LAYER PROTEIN, RsaA
44. PROTEIN C PRECURSOR (EC 3.4.21.69) (AUTOPROTHROMBIN)
45. PROTEIN C (ACTIVATED) (EC 3.4.21.69) PRECURSOR
46. PROCOLLAGEN ALPHA 2(1) CHAIN PRECURSOR
47. PRO ALPHA 2(I) COLLAGEN – MOUSE
48. PROTEIN C PRECURSOR (EC 3.4.21.69) (AUTOPROTHROMBIN)
49. SPIDROIN 2, DRAGLINE SILK FIBROIN – ORB SPIDER
50. PROTEIN C (ACTIVATED) (EC 3.4.21.69) PRECURSOR

FIG. 19B2

51. PROTEIN C (EC 3.4.21.-) PRECURSOR - RAT
52. SILK FIBROIN, DRAGLINE - ORB SPIDER
53. PLASMA KALLIKREIN (EC 3.4.21.34) PRECURSOR - HUMAN
54. PLASMA KALLIKREIN PRECURSOR (EC 3.4.21.34)
55. PLASMA KALLIKREIN PRECURSOR (EC 3.4.21.34)
56. FILAMENTOUS HEMAGGLUTININ - BORDETELLA PERTUSSIS
57. PLASMA KALLIKREIN (EC 3.4.21.34) PRECURSOR - MOUSE
58. T-PLASMINOGEN ACTIVATOR (EC 3.4.21.68) alpha 2 PRECURSOR
59. MSB2 PROTEIN
60. MSB2 PROTEIN - YEAST (SACCHAROMYCES CEREVISIAE)
61. PLASMA KALLIKREIN PRECURSOR (EC 3.4.21.34)
62. PLASMINOGEN PRECURSOR (EC 3.4.21.7)
63. PLASMINOGEN PRECURSOR - MOUSE
64. T-PLASMINOGEN ACTIVATOR (EC 3.4.21.68)
65. SALIVARY PLASMINOGEN ACTIVATOR PRECURSOR
66. PLASMA KALLIKREIN (EC 3.4.21.34) PRECURSOR - RAT
67. T-PLASMINOGEN ACTIVATOR (EC 3.4.21.68) beta PRECURSOR
68. HMW1=HIGH MOLECULAR-WEIGHT SURFACE-EXPOSED PROTEIN
69. SERINE PROTEASE HEPSIN (EC 3.4.21.-)
70. SERINE PROTEASE HEPSIN (EC 3.4.21.-)
71. HEPSIN - RAT
72. HEPSIN - RAT
73. HEPSIN (EC 3.4.21.-) - HUMAN
74. PLASMINOGEN (EC 3.4.21.7)
75. T-PLASMINOGEN ACTIVATOR (EC 3.4.21.68) alpha-1 PRECURSOR
76. NAD(P)+ TRANSHYDROGENASE (B-SPECIFIC) (EC 1.6.1.1)
77. COLLAGEN ALPHA 2(V) CHAIN - HUMAN (FRAGMENT)
78. NAD(P) TRANSHYDROGENASE, MITOCHONDRIAL PRECURSOR
79. RNA1 POLYPROTEIN (253 KD PROTEIN)
80. GENOME POLYPROTEIN - GRAPEVINE FANLEAF VIRUS
81. PROTEIN-TYROSINE KINASE (EC 2.7.1.112)p150-HUMAN
82. PLASMIN (EC 3.4.21.7) PRECURSOR - RHESUS MACAQUE
83. PLASMIN (EC 3.4.21.7) PRECURSOR - RHESUS MACAQUE
84. COAGULATION FACTOR XIa (EC 3.4.21.27) PRECURSOR
85. PROCOLLAGEN alpha 2(IV) CHAIN PRECURSOR
86. PLASMINOGEN PRECURSOR (EC 3.4.21.7)
87. COAGULATION FACTOR XI PRECURSOR (EC 3.4.21.27)
88. COLLAGEN alpha 2(IV) CHAIN PRECURSOR - MOUSE
89. MAJOR AMPULLATE FIBROIN PROTEIN - ORB SPIDER
90. SILK FIBROIN (FRAGMENT)
91. COAGULATION FACTOR X PRECURSOR (EC 3.4.21.6)
92. PLASMIN (EC 3.4.21.7) PRECURSOR - HUMAN
93. COAGULATION FACTOR Xa PRECURSOR (EC 3.4.21.6) PRECURSOR
94. PLASMIN (EC 3.4.21.7) PRECURSOR - HUMAN
95. PLASMINOGEN PRECURSOR (EC 3.4.21.7)
96. PLASMINOGEN (EC 3.4.21.7)
97. PLASMIN (EC 3.4.21.7) PRECURSOR - HUMAN
98. HCF, C1, VCAF, CFF=VP16 ACCESSORY PROTEIN HOST CELL
99. PROTEOGLYCAN CORE PROTEIN PRECURSOR, CARTILAGE
100. PLASMIN (EC 3.4.21.7) - BOVINE

CYCLIC PEPTIDE CATALYSTS MODELED
ON ENZYME ACTIVE SITES

CROSS-REFERENCE TO RELATED APPLICATIONS

This is the U.S. National Phase of PCT/US94/05569 filed May 18, 1994, which is a continuation-in-part of Ser. No. 08/063,640 filed May 18, 1993 (abandoned). This application is also a continuation-in-part of Ser. No. 08/461,597 filed Jun. 5, 1995 now U.S. Pat. No. 5,759,834.

BACKGROUND OF THE INVENTION

A. Field of the Invention

The present invention relates to chemically synthesized catalysts which are capable of catalyzing chemical reactions heretofore only efficiently catalyzed using naturally-occurring molecules. In particular, the invention pertains to catalytic compositions of matter and to catalyst chemical structures, to methods of producing the kinds of catalysts described, and to chemical reactions in which the catalytic compositions can be applied.

B. Description of the Related Art

For almost a century, catalytic macromolecules have occupied center-stage in life sciences and medicine because they catalyze many of the important chemical processes carried out in living organisms. In fact, one of the principal achievements of the modern pharmaceutical industry is the production of large quantities of such molecules for use in health care. More recently, the application of these catalysts in non-biological chemical processes has received the increasing interest of industrial chemists.

Entire enzyme molecules have been synthesized as a result of major advances in the knowledge of protein structure and solid-phase peptide chemistry. Some of these whole molecules retained the catalytic nature of the naturally-occurring enzyme. However, the molecules upon which the synthetic molecules were modeled were relatively small and the yields of the correct structures were extremely low due to the inherent limitations of solid-phase peptide synthesis. These failures made it evident that synthesizing whole enzymes merely to achieve the catalytic capability of the naturally occurring molecule was not a viable approach for the construction of commercial quantities of catalysts. Neither is this approach at all useful for larger enzymes which may comprise several hundreds of amino acid residues in their chains. Clearly, it would be highly desirable if it were possible to obtain the desired chemical activity without synthesizing the entire enzyme structure.

A short peptide was previously designed by the Applicant using surface-simulation synthesis to mimic the substrate-binding site of trypsin. This peptide was shown to possess the expected binding activities of the native enzyme with substrates and inhibitors (Atassi, M. Z., "Surface-Simulation Synthesis of the Substrate-Binding Site of an Enzyme," Biochem. J. Vol. 226, pp. 477–485 [1985]). However, although the synthetically produced peptide had the ability to bind to substrates and competitive inhibitors, it exhibited no significant catalytic activity.

Artificial linear peptide was synthesized consisting of 34 residues the selection of which was based upon secondary structure prediction rules. A dimer of this peptide showed limited nuclease activity (Gutte, B., et al., Nature 281: 650–655 (1979). More recently and representative of this type of approach to synthetic catalyst design, an attempt was made to synthesize a portion of an enzyme molecule which would have a desired chemical activity. K. W. Hahn et al., "Design and Synthesis of a Peptide Having Chymotrypsin-Like Esterase Activity," Science, Vol. 248, pp. 1544–1547 (1990), describe the construction of a catalytic molecule in which four helical peptides were assembled in a bundle which contained at its amino ends, serine, histidine and aspartic acid in a spatial arrangement similar to that present in chymotrypsin ($\alpha$CT). This assembled-helical design molecule contained 73 residues representing a major portion of and derived from the whole enzyme and was capable of binding to ester substrates of $\alpha$CT. The assembled-helical design molecule was limited to hydrolyzing an acetyltyrosine ethyl ester for about 100 turnovers and was limited to a rate of catalysis which was only about 0.02% that of the native $\alpha$CT. Importantly, the sequences in the marginally catalytic synthetic structure derived from the whole enzyme were substantially the same as the equivalent sequences found in the native enzyme.

Quite different approaches to attaining the chemical advantages of enzymes without having to rely on the native molecule have involved a unique use of immunological molecules. Monoclonal antibodies with catalytic activity have been prepared by using transition-state intermediates of the substrate as the immunizing antigen. Again, these molecules demonstrate binding of substrate but possesses only marginal activity.

However, no synthetic catalytic structure representing significantly less than, but designed to structurally imitate, an enzyme has functioned like a true enzyme. Specifically, no chemically synthesized, low molecular weight catalyst comprising a peptide has been produced which is capable of converting a substrate to a product in a specific manner at pre-selected bonds, at a useful rate of catalysis and for a useful period of time.

SUMMARY OF THE INVENTION

In accordance with the present invention, Applicant has constructed relatively low molecular weight, synthetic catalysts having the functional characteristics of naturally occurring enzymes. The synthetic catalysts of the invention represent molecules which are significantly smaller than, but designed to structurally imitate, an enzyme to the degree that they function like the native enzyme. These catalysts are capable of converting a substrate to a product as does the native enzyme upon which they are modeled in a highly specific manner, at pre-selected chemical bonds, at commercially useful rates of catalysis and for commercially useful periods of time. In some instances, the synthetic catalysts actually improve upon the characteristics of the native molecule when comparisons of specificity, turnover rates, temperature sensitivity and the like are carried out.

The synthetic catalysts of the invention generally comprise a sterically-constrained peptide comprising amino acids. Herein, the term amino acid refers generally to L-amino and imino acids routinely encountered in native enzymes as well as to analogs of these naturally occurring compounds including D-amino acids and the like.

Further, the sterically-constrained catalyst comprises, in part, those amino acids which are in the active site of the naturally occurring enzyme. For the purposes of this invention, an active site amino acid is one which interacts with a substrate, substrate analog, transition-state substrate/product or competitive inhibitor of the native enzyme. The interaction may be one which achieves the goal of binding the substrate to the catalytic surface of the enzyme. The interaction may also be one which actually causes the conversion of the substrate to product, such as by temporary donation of electrons to cause the cleavage of a bond in the substrate. Not uncommonly, the nature of the interaction may be a hybrid interaction where both binding and conversion of substrate to product occurs.

This interaction may comprise a very tight interaction such as through one or more covalent bonds shared, however briefly, between the substrate and the active site amino acid. The interaction between the substrate and the active site amino acid may be of a weaker nature such as through hydrogen bonding, hydrophobic bonding or other weak inter-molecular interactions. Regardless of the actual interaction, be it mere binding, conversion or a combination of the two, or be it of a strong or weak character, for the purposes of the invention, such interactions with the substrate cause an amino acid residue to fall within the definition of an active site amino acid.

Identification of active site amino acids is routinely carried out on enzymes for which 3-dimensional structural information is known. In certain cases, substrate analogs or transition-state substrate analogs/product are utilized which allow the protein chemist to determine which of the amino acids exposed to the catalytic surface (active site) of the enzyme interact with the substrate. Typically these interactions are detected using analytical techniques such as X-ray crystallography, mass spectroscopy, nuclear magnetic resonance and the like.

In certain instances, having applied one or more of these techniques, it will be known precisely which one of the amino acid residues exposed to the catalytic surface actually cause the substrate to be bound to or otherwise interact with the catalytic surface of the enzyme. Similarly, it may be known precisely which one of the amino acid residues exposed to the catalytic surface actually cause the substrate to be converted to product. More typically, however, the actual site of interaction of the substrate with the catalytic surface residues will be narrowed down to a defined region comprising sequences and/or amino acid residues that are in close proximity to one another in 3-dimensional structure but distant in primary structure among which are the actually interacting residues. For the purposes of the invention, each of the sequences and amino acid residues in such a region among which are the actually interacting residues are considered to be active site amino acid residues. This is particularly the case since it is not unlikely that each residue in such a region may coordinately participate in the binding or conversion of the substrate, leaving no one residue among them to be singled out as the actually interacting residue.

Additionally, it will be understood by those of skill in the art that certain enzymatic reactions are catalyzed indirectly by ligands bound to the enzyme active site, which ligands themselves are bound by interactions with the amino acid residues in the enzyme chain. In such instances, the amino acids which bind the ligand which in turn interacts with the substrate are expressly included within the definition of the active site amino acids of the invention.

Selection of the active site amino acids to be included in the synthetic catalysts of the invention may actually involve the isolation, purification and 3-dimensional analysis to a sufficiently detailed degree of resolution of a protein for which the substrate interactions with the catalytic surface are unknown. The techniques for doing so are known well by those of skill in the art. Even so, the obtaining of such data routinely involves substantial investments of research time and effort. Fortunately, however, the structural information of the degree of resolution necessary to allow selection of the active site amino acids is known for a large number of enzymes. As more enzymes are subjected to 3-dimensional analysis and included in the relevant databases, synthetic catalysts modeled after such enzymes may be constructed in a straightforward manner using the methods of the invention.

A number of sources are available for both the 3-dimensional structural information as well as the amino acid sequence information which may be used in designing the catalysts of the invention. In the United States, a useful source is the Protein Data Bank, Chemistry Department, Building 555, Brookhaven National Laboratory, Upton, N.Y. 11973. Protein Data Bank Service Association member centers are located worldwide and include Canadian Scientific Numeric Data Base Service, Dutch National Facility for Computer Assisted Chemistry, NE Italy Interuniversity Computing Center, European Molecular Biology Laboratory, Japan Association for International Chemical Information, National Center for Supercomputing Applications, Osaka University, Pittsburgh Supercomputing Center, Prophet, San Diego Supercomputing Center, and SEQNET. Addresses, phone numbers, and access to magnetic media at the parent facility as well as the member centers may be obtained through the Protein Data Bank. Commercial search firms also have access to protein sequence databases such as Intelligenetics of Mountain View, Calif.

Moreover, in many cases, enzymes fall into classes which allow certain structural generalizations to be made in the selection of the active site amino acids. Thus, enzymes may be classified into classes according to the substrates they convert—proteases digest proteins, lipases attack lipids, and so on. Subclasses of proteins also exist—serine proteases possess a serine in their active sites useful in the cleaving of peptide bonds in proteins. Even more useful is the fact that many proteins, especially those falling into the same classes and subclasses, exhibit a great deal of amino acid sequence homology. Thus, trypsin and chymotrypsin, both of which are serine proteases, share many of the same or chemically similar amino acid residues at or near the same positions in each enzyme chain. Chemically similar substrates (for example, protein substrates of proteases) impose very similar structural requirements on the catalytic surfaces in the active sites of the enzymes which convert the substrates to products (i.e., serine proteases cleaving peptide bonds of protein substrates, albeit at different positions).

Therefore, the catalyst designer having designed a synthetic catalyst based on the known 3-dimensional structure of one enzyme in a given class, can justifiably rely on such homology in selecting the active site amino acids of another enzyme of the same class for which there is substantial homology. This approach has been successfully utilized by the Applicant to design a synthetic trypsin-like catalyst based upon the homology of trypsin with chymotrypsin. Thus, active site amino acids may also be defined by their homology with the same or similar residues in an enzyme for which the 3-dimensional structure is known. If an active site residue has been defined in the enzyme for which the 3-dimensional structure is known, and an homologous region of a related, closely homologous enzyme with undetermined 3-dimensional structure is known, then by analogy those residues falling within the homologous region may be justifiably considered to be active site residues. Such residues are, therefore, included within the definition of active site amino acid for purposes of the invention.

By design methods as detailed herein, after the identification of the active site amino acids, these residues are arranged to have a 3-dimensional spacial relationship which is essentially equivalent to that of the naturally occurring enzyme. Chiefly, this entails measurements of the distances between the active site residues from α-carbon to α-carbon in the peptide bond. Thus, if the α-carbon of active site residue A is spatially separated from the α-carbon of active site residue B by 10 Å, it will be understood that the resulting design must provide a similar distance to be achieved in the synthetic catalyst. Surprisingly, the Applicant has found that at least some flexibility in design is allowable indicating that less exacting distances between α-carbons may be tolerated. For instance, in the chymotrypsin and trypsin designs which follow, the α-carbon of invariant residue aspartic acid −102 is actually separated by 10.25 Å from the α-carbon of alanine-55 and from the α-carbon of isoleucine/leucine-99 (chymotrypsin/trypsin) by 5.18 Å. By simple error, in constructing certain versions of the synthetic catalysts, the α-carbon of aspartic acid-102 was positioned 10.25 Å from the α-carbon of isoleucine/leucine-99 and 5.18 Å from the α-carbon of alanine-55. Even so, the Applicant obtained activities similar to those reported below. This would indicate that even lower levels of resolution in the 3-dimensional structure of an enzyme may be useful in creating the synthetic catalysts of the invention.

In the first instance, the 3-dimensional relationship may be promoted using spacers such as catalytically inactive amino acids between the active site amino acids. The bond lengths of representative spacers are detailed in the Examples to follow. By way of continuing example, however, if active site residues A and B above were to be linked by spacers, the linear distance of 10 Å would determine the number and the nature of the spacers to be used. As used herein, a catalytically inactive amino acid is any amino acid which does not fall within the definition of an active site amino acid as defined supra. Other spacers which would not fall within the definition of amino acids as used herein but which would function structurally and chemically in a similar fashion will find usefulness, as well.

Steric constraint of the catalyst may take several forms. Certainly, the Applicant has found that cyclization of the catalyst achieves the goal of steric constraint admirably. However, the goal of steric constraint may be achieved by other means as well. Thus, co-terminal attachment of the N- and C-termini of the linear peptide to a surface in close proximity to one another is such a means of sterically constraining the catalyst. For the purposes of the present invention, any means which sterically, torsionally or conformationally constrains the catalyst in a manner which allows the requisite flexibility of the chain to conform to the substrate yet which eliminates a large portion of the non-productive (non-catalytic) conformations which would result from a strictly linear, freely mobile chain in solution are expressly included in this definition.

The means for steric constraint must meet at least two criteria. First, the means for sterically constraining the catalyst must maintain the interchain distances necessary for attaining the proper orientation of active site residues around the substrate in a fashion similar to that occurring in the native enzyme. Second, the means for constraining the catalyst must be at least stable enough under the conditions of the reaction with the substrate to maintain the sterically constrained, functional nature of the catalyst. Certainly, the Applicant has found that a simple yet effective means for constraining the catalyst is to include at its N- and C-termini a cysteine residue in order to allow the formation of a disulfide bond between the terminal residues thereby closing the linear catalyst into a cyclic structure. In certain instances, incorporation of a cysteine residue in the synthetic catalyst may mimic a similar residue in the naturally-occurring enzyme. In others, the added cysteine will be without homology to the naturally-occurring enzyme. If a cysteine residue is necessarily included as a residue in an active site region, and the inclusion cannot be made in such a way as to make the cysteine residue an N- or C-terminus, it will be advisable to convert it to a non-disulfide linkage-forming residue where cyclization is to be achieved by terminal cysteines. Where a cysteine residue is required for activity (e.g. cysteine proteases), steric constraint must be achieved by means other than a disulfide bond. Such a constraint should be to stable to reduction. The pepzyme could then be made with the required cysteine residue in the design and, even though such a pepzyme could then dimerize, its activity would be re-established in the presence of a reducing agent. Other intramolecular disulfide linkages work as well. Alternatively and preferably where a bond such as the disulfide linkage may be susceptible to being reduced, intramolecular cyclization may be achieved via peptide bonding between any two terminal amino acids so long as the proper interchain distances are maintained. Other interchain and intrachain bonding, including bonding or crosslinking to and between non-amino acid substituents of the catalyst may be used to sterically constrain the catalyst so long as the means achieve the two criteria detailed supra.

Thus, the catalysts of the invention may achieve steric constraint by constructing a cyclized catalyst containing an end-to-end joint between N- and C-termini of the catalyst. In certain embodiments, the end-to-end joint further comprises a disulfide bond, a peptide bond or a linking molecule which is not an amino acid (e.g., sugars, lipids, carbon-carbon bonds, and the like).

Since there is no a priori reason for closing the synthetic peptide catalyst chain at a particular site along its linear structure, it is possible to construct the linear catalyst using standard peptide synthesis chemistry or through recombinant DNA techniques as any of a number of possible linear configurations. Some of these linear configurations may be preferable to others for purposes of synthesis, especially where it is desired to use disulfide linkages to cyclize the catalyst and the interchain distances limit the placement of the disulfide linkage to one or only a few potential sites within the linear catalyst. Where cyclization is affected by means other than disulfide linkages, the order of synthesis is more flexible.

Thus, claimed herein are synthetic catalysts capable of catalyzing reactions of substrates in a manner similar to that of naturally-occurring enzymes. The catalysts generally comprise sterically-constrained peptides, which peptides are themselves made up of, at least in part, amino acids. The amino acids which are used to synthesize the peptide further comprise at least some of the active site amino acids known to exist in the naturally-occurring enzyme upon which the catalyst is modeled. The catalyst is also made up of one or more spacers variously interspersed during synthesis of the linear peptide between the active site amino acids.

The active site amino acids are arranged during the synthesis of the linear peptide to achieve a linear relationship along the length of the catalyst such that, when contorted properly in 3-dimensional space, the catalyst is capable of assuming a 3-dimensional spacial relationship amongst these active site amino acids. The 3-dimensional spacial relationship is essentially equivalent to that present in the naturally-occurring enzyme in its catalytically active state. Unlike this essential equivalency of 3-dimensional spatial intermolecular distances, the linear relationship between the active site amino acids along the length of the synthetic catalyst is substantially different from that of the naturally-occurring enzyme. In many cases, the linear relationships established in the synthetic catalysts of the invention will be substantially altered and even reversed from that observed in the native molecule. Since the synthetic catalyst incorporates in the design only the essential residues of the active site which are linked with proper spacing and directionality, large amounts of the linear sequence found in the naturally-occurring enzyme interspersed between the active site regions/residues will be missing from the synthetic catalyst. Thus, the catalysts have molecular weights substantially less than that of the naturally-occurring enzyme upon which they are modeled.

The catalysts of the invention display reaction kinetics that are enzyme-like for substrates, substrate analogs and competitive inhibitors of the correlate enzymes. The substrates are converted in an essentially equivalent manner (i.e., chemically equivalent) to that of the correlate enzyme. Herein, substrates of a synthetic catalyst are understood to include at least the substrates of the correlate enzyme. While certain synthetic catalysts may have unique substrates not shared with the correlate enzyme, those substrates will typically be determined empirically based on similarity to the correlate enzyme substrates. Herein, binding specificity is meant to refer to substrate preference. As seen herein, a mere four alterations in the active site residues of the chymotrypsin-like synthetic catalyst causes the resulting trypsin-like catalyst to no longer bind to or cleave proteins at chymotrypsin cleavage sites, rather it then only binds and cleaves proteins at trypsin cleavage sites. Binding constant is meant to refer to the values used in determining the proportional Michaelis-Menten constant ($K_m$). In certain embodiments, the catalysts of the invention have binding constants for their respective substrates which are approximately of the same order of magnitude or at most 100 times that of or better than that of the naturally-occurring enzyme. As evidenced in the examples to follow, it is known that naturally occurring homologs of a given enzyme display different affinities for the same substrate and convert that substrate at different rates. In preferred embodiments, the binding constant of the synthetic catalyst will be essentially equivalent to that of the native molecule. Similarly, the preferred catalysts have rates of catalysis ($k_{cat}$) which are approximately 1% of or better than that of the naturally-occurring enzyme. In preferred embodiments, the rate of catalysis of the synthetic catalyst will be essentially equivalent to that of the native molecule. In highly preferred embodiments, the rates of catalysis of the synthetic catalysts will be superior to that of the native molecule, especially where the catalysis takes place in a reaction environment unfavorable for the native enzyme such as with elevated and depressed temperatures or other situations where the native structure is susceptible to denaturing. In certain instances, as shown in the examples to follow, the turnover number (the cycles of catalysis in a given amount of time) of the synthetic catalysts of the invention exceed that of the native enzyme to such a degree that it remains undetermined how many turnovers are theoretically possible with the synthetic molecules. Due to their size and lack of steric constraints, the synthetic catalysts of the invention may be capable of approaching rates close to that controlled only by diffusion.

The catalysts of the invention, as noted previously, have molecular weights substantially less than that of the native enzymes. This is a function of the need to incorporate and link together only the active site residues of the enzyme into the constructed design. The size of the catalysts is therefore dictated to a large degree by the size of the active site of the modeled enzyme. In any case, the numbers of amino acid residues of certain preferred synthetic catalysts will rarely exceed approximately 30% of that of the naturally-occurring enzyme.

Of course, the skilled artisan will recognize that there may be additions to the minimal synthetic catalyst made for other reasons which would add to the mass of the molecule. Thus, for instance, it may be possible to add allosteric regions to the basic catalytic molecule in order to regulate the catalysis. Additionally, it is likely that multimers of the synthetic peptide catalysts may exhibit preferred characteristics and would thereby add additional mass to such catalysts. For instance, it is readily apparent that mixed function synthetic catalysts may be constructed using the methods and compositions of the present invention. A trypsin-like synthetic catalyst may be coupled to a chymotrypsin-like catalyst to achieve a combined catalyst which will act on either protein substrate by covalently bonding two distinct synthetic catalyst molecules via, for instance, the side chains present in either molecule's amino acid residues. In certain instances, it may be desirable to increase the solubility or serum life of a catalyst of the invention by attaching it to a solubilizing agent or stabilizing agent, such as lysozyme, polyethylene glycol, polyvinyl alcohol or the like, adding mass to the catalyst in the process. Also, where a ligand is bound and is involved in catalysis, mass increases are possible. Thus, while it is anticipated that the basic synthetic peptide catalyst will be substantially reduced in molecular weight compared to the native enzyme, synthetic constructions which add mass to this basic configuration are expressly anticipated.

The spacers which may further comprise catalytically inactive amino acids will be recognized by one of skill in the art to meet certain criteria. Chiefly, such amino acid spacers will be amino acids which have a minimal steric hindrance capacity as it relates to movement of the peptide in all dimensions. Additionally, the spacer amino acids will typically lack such side groups as might interfere in catalysis such as reactive, hydrophilic, hydrophobic groups or other such moieties. Typically, such amino acid spacers will be glycyl, seryl or alanyl residues. However, in certain instances, it may be desirable to use one or more spacers selectively introduced into the catalyst design to impart a desired conformational constraint on the design, such as by using proline residues to introduce a kink. Such chain kinks may help to further sterically constrain the synthetic catalyst to additionally limit the non-catalytic conformations which the cyclic molecule takes in solution.

In certain preferred embodiments of the invention, the catalysts of the invention were modeled upon naturally-occurring enzymes selected from the group of enzymes consisting of chymotrypsin, trypsin, lysozyme and ribonuclease. These were the enzymes which the Applicant chose to be representative of the wide utility of the present invention in constructing synthetic catalysts. This selection was made in order to demonstrate in the one instance that while a 3dimensional structure is advantageous and ultimately necessary to construct the synthetic catalysts of the present invention, where amino acid sequences exist which are highly homologous to a known 3-dimensional structure, substitution of the relevant catalytic residues was carried out to alter the catalytic specificity of the resulting catalyst. Thus, trypsin residues were shown in the examples to follow to be replaced for chymotrypsin residues in a 3-dimensional catalyst based only upon the chymotrypsin X-ray coordinates. In the second instance, these exemplary enzymes were diversely selected to demonstrate that the compositions of matter and methods of the invention were not limited to enzymes catalyzing only certain classes of substrate. While both chymotrypsin and trypsin are proteolytic enzymes, lysozyme is a polysaccharide digesting enzyme and ribonuclease hydrolyzes the bonds of RNA. These selections were only exemplary. The approaches and designs detailed herein allow any one of skill in the art with the requisite 3-dimensional data necessary (or homologous to) to design a peptide capable of assuming that 3-dimensional structure. Molecular modeling computer programs known to those of skill in the art may also provide useful information when comparing substrate induced-fit of the synthetic catalysts of the invention.

More specifically, representative catalysts are disclosed which indicate the utility and scope of the present invention across a wide range of natural enzyme models. One preferred catalyst is modeled on chymotrypsin and consists essentially of the cyclic amino acid catalyst:

cyclo(-S-cystinyl-glycyl-phenylalanyl-histidyl-phenylalanyl-glycyl-glycyl-seryl-aspartyl-glycyl-methionyl-glycyl-seryl-seryl-glycyl-glycyl-valyl-seryl-tryptophanyl-glycyl-isoleucyl-glycyl-glycyl-aspartyl-glycyl-alanyl-alanyl-histidyl-cystinyl-S) (SEQ ID NO:1); wherein "cyclo" refers to the cyclic nature of the peptide and the residues "-S-cystinyl" and "-cystinyl-S" indicate that the peptide was cyclized through the use of a disulfide bond between the two cysteine residues. Another preferred catalyst is modeled on trypsin and consists essentially of the cyclic amino acid catalyst:

cyclo(-S-cystinyl-glycyl-tyrosyl-histidyl-phenylalanyl-glycyl-glycyl-seryl-aspartyl-glycyl-glutamyl-glycyl-seryl-aspartyl-glycyl-glycyl-valyl-seryl-tryptophanyl-glycyl-leucyl-glycyl-glycyl-aspartyl-glycyl-alanyl-alanyl-histidyl-cystinyl-S) (SEQ ID NO:2).

Another preferred catalyst is modeled on lysozyme and consists essentially of:

cyclo(-S-cystinyl-threonyl-asparagyl-arginyl-asparagyl-glycyl-glycyl-aspartyl-glycyl-glycyl-leucyl-glutamyl-isoleucyl-asparagyl-glycyl-tryptophanyl-tryptophanyl-glycyl-glycyl-isoleucyl-glycyl-aspartyl-glycyl-aspartyl-glycyl-alanyl-tryptophanyl-valyl-alanyl-glycyl-arginyl-glycyl-phenylalanyl-glutamyl-seryl-asparagyl-cystinyl-S) (SEQ ID NO:3).

Another preferred catalyst is modeled on ribonuclease and consists essentially of:

cyclo(-S-cystinyl-glutamyl-glycyl-valyl-histidyl-phenylalanyl-aspartyl-alanyl-seryl-glycyl-glycyl-threonyl-asparagyl-valyl-prolyl-lysyl-glycyl-glycyl-glutamyl-histidyl-glycyl-phenylalanyl-lysyl-cystinyl-S) (SEQ ID NO:4).

Another preferred catalyst is modeled on urokinase and consists essentially of:

cyclo(-S-cystinyl-glycyl-threonyl-tyrosyl-valyl-glycyl-glycyl-seryl-aspartyl-glycyl-glutaminyl-glycyl-seryl-aspartyl-glycyl-glycyl-valyl-seryl-tryptophanyl-glycyl-leucyl-glycyl-glycyl-aspartyl-glycyl-alanyl-threonyl-histidyl-cystinyl-S) (SEQ ID NO:5).

Another preferred catalyst is modeled on tissue plasminogen activator and consists essentially of:

cyclo(-S-cystinyl-glutamyl-arginyl-phenylalanyl-leucyl-glycyl-glycyl-seryl-aspartyl-glycyl-glutaminyl-glycyl-alanyl-aspartyl-glycyl-glycyl-isoleucyl-seryl-tryptophanyl-glycyl-tyrosyl-glycyl-glycyl-aspartyl-glycyl-alanyl-alanyl-histidyl-cystinyl-S) (SEQ ID NO:6).

It will be recognized, however, by those of skill in the art that the catalysts described above and those claimed in general may contain functionally equivalent amino acid substitutions. The importance of the hydropathic index of amino acids in conferring biological function on a peptide is generally known by those of skill in the art. It has been found by many researchers that certain amino acids may be substituted for other amino acids having a similar hydropathic index or score and still retain similar if not identical biological activity. As displayed below, amino acids are assigned a hydropathic index on the basis of their hydrophobicity and charge characteristics. It is believed that the relative hydropathic character of the amino acid determines the secondary structure of the resultant peptide, which in turn defines the interaction of the peptide with the substrate molecule. It is proposed that biological functional equivalence may typically be maintained where amino acids are exchanged having no more than a ±1 to 2 difference in the index value, and more preferably within a ±1 difference.

| AMINO ACID | HYDROPATHIC INDEX |
| --- | --- |
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and might still obtain a peptide having similar biological activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

| ORIGINAL RESIDUE | EXEMPLARY SUBSTITUTIONS |
| --- | --- |
| alanine | glycine; serine |
| arginine | lysine |
| asparagine | glutamine; histidine |
| aspartic acid | glutamic acid |
| cysteine | serine |
| glutamine | asparagine |
| glycine | alanine |
| histidine | asparagine; glutamine |
| isoleucine | leucine; valine |
| leucine | isoleucine; valine |
| lysine | arginine; glutamine; glutamic acid |
| methionine | leucine; tyrosine |

-continued

| ORIGINAL RESIDUE | EXEMPLARY SUBSTITUTIONS |
|---|---|
| serine | threonine |
| threonine | serine |
| tryptophan | tyrosine |
| tyrosine | tryptophan; phenylalanine |
| valine | isoleucine; leucine |

The invention also relates to methods of synthesizing a catalyst capable of catalyzing a reaction of a substrate in a manner similar to that of a naturally-occurring enzyme. These methods generally comprise first selecting certain amino acids to be included in the catalyst from at least some of the active site amino acids in the naturally-occurring enzyme. As noted above, the Protein Data Bank readily provides an excellent source of such information in the form of both 3-dimensional structure, probable active site residues, sequences and sequence homologies between related enzymes. Where the designer chooses to base the design of the catalyst on a known 3-dimensional structure of an enzyme, reference is first made to such a source for the distances separating and the identity of the active site residues on the catalytic surface of the enzyme. If the design is to be based upon the sequence homology of an enzyme for which the 3-dimensional structure is unknown but which unknown enzyme is related to an enzyme of known 3-dimensional structure, then a first step includes design of a first catalyst modeled after the known 3-dimensional structure enzyme. This step is followed by substitutions of active site amino acids where the unknown 3-dimensional structure enzyme differs with that of the known enzyme as determined by sequence homologies.

The elements of the design first require the identification of the active site residues and the α-carbon to α-carbon distances separating them. This is based on the structural homology with the known reference enzyme. Next, a selection is made of one or more spacers to be variously interspersed between the active site amino acids selected in the first step. The distances determined in the first step between the active site residues guide the selection of a proper atomic bridging structure in the form of a spacer to be used. Reference should be made to the detailed examples herein for representative spacers and their atomic dimensions. Of course, the spacers used herein are but exemplary and may be readily substituted by any spacer of suitable dimensions and chemical compatibility.

Having selected the substituents of the synthetic catalyst, a next step will typically include synthesizing a linear peptide by stepwise addition of either the active site amino acids or the spacers to the growing peptide to achieve the proper linear arrangement and distances. While the Applicant has demonstrated the utility and ease by which this may be accomplished using synthetic peptide chemistry, it is certainly possible and, in some cases, advisable to achieve the synthesis of the peptide using recombinant DNA technology. Either approach is permissible. In either case, the preferred order of synthesis will typically be dictated by the position deemed best for cyclization. Thus, where a disulfide linkage is to be used to cyclize the catalyst, synthesis will typically begin with a cystinyl residue and end with a cystinyl residue. Alternatively, where a peptide bond is used to cyclize the peptide, less concern need be placed on the specific starting point synthesis.

Having so constructed the linear peptide, this establishes a linear relationship along the peptide such that the peptide is capable of assuming a 3-dimensional spacial relationship amongst the active site amino acids. The 3-dimensional spacial relationship is essentially equivalent to that present in the naturally-occurring enzyme in its catalytically active state. Conversely, the linear relationship is substantially different from that of the naturally-occurring enzyme. As a result of the unique linear bridging of active site residues, there is no need to include vast amounts of the amino acids typically found along the native polypeptide chain nor is there a need to maintain the order of sequence found along the native polypeptide chain. The result of this cutting out of most of the non-catalytic residues found in the native polypeptide is that the catalyst has a molecular weight substantially less than that of the naturally-occurring enzyme. As a final step, the linear peptide is sterically-constrained by one or another of the techniques discussed above.

A process using the synthetic catalysts of the invention to catalyze a reaction of a substrate in a manner similar to that of a naturally-occurring enzyme is also provided. Typically, the synthetic peptide catalysts of the invention are used in exactly the same manner and under identical conditions for which the native enzyme is known to function best. Thus, buffered solutions at given temperatures and given concentrations which conform to equivalent molar ratios of catalyst to substrate are preferred. However, since the catalysts of the invention may exhibit enhanced ability to function under conditions which would denature or otherwise reduce the catalytic ability of the native enzyme, in some instances the synthetic catalysts of the invention may be used under conditions different from those that are maximal for the native molecules. In any case, no special conditions over those routinely utilized by those of skill in the art of enzymology are necessary when using the catalysts of the invention. Products produced using the catalytic processes of the invention are also provided.

In addition to the terms and definitions discussed above, the following abbreviations are used herein: BTEE, N-benzoyl-L-tyrosine ethyl ester; BPTI, bovine pancreatic trypsin inhibitor; ChPepz, peptide designed by surface-stimulation synthesis to mimic the active site of α-chymotrypsin; DIFP, diisopropyl fluorophosphate; PMSF, phenylmethylsulfonyl; TAME, N-tosyl-L-arginine methyl ester; TPCK, L-1-p-tosylamino-2-phenylethyl chloromethyl ketone; and TrPepz, surface-stimulation synthetic peptide designed to mimic the active site of trypsin; DTT, dithiothreitol; LyPepz, peptide designed by surface-simulation synthesis to mimic the active site of hen egg lysozyme; LYZ, hen egg lysozyme; RNASE, bovine ribonuclease A; RnPepz, surface-simulation synthetic peptide designed to mimic the active site of bovine ribonuclease A.

BRIEF DESCRIPTION OF THE DRAWINGS

FIG. 16. A. Tabulated results of computer search of PIR and SWISS-PROT databases utilizing Chymotrypsin B precursor as the query sequence. Active site residues which were previously utilized to construct a synthetic catalytic chymotrypsin peptide are indicated across the top of the Figure along with the sequence number based upon the chymotrypsin linear sequence. To the left of the Figure, numbered references are indicated which refer to the sequences listed in B below. For each such sequence, divergences from the active site residue utilized to obtain chymotrypsin activity are shown. B. The first 100 sequences demonstrating varying degrees of sequence homology with the query sequence. Homology searching was accomplished using FastDB-Fast Pairwise Comparison of Sequences (Release 5.4) by Intelligenetics, Inc., 700 East El Camino Real, Mountain View, Calif. 94040.

FIG. 17. A. Tabulated results of computer search of PIR and SWISS-PROT databases utilizing Lysozyme C2 Bovine as the query sequence. Active site residues which were previously utilized to construct a synthetic catalytic lysozyme peptide are indicated across the top of the Figure along with the sequence number based upon the lysozyme linear sequence. To the left of the Figure numbered references are indicated which refer to the sequences listed in B below. For each such sequence, divergences from the active site residue utilized to obtain lysozyme activity are shown. B. The first 100 sequences demonstrating varying degrees of sequence homology with the query sequence. Homology searching was accomplished using FastDB-Fast Pairwise Comparison of Sequences (Release 5.4) by Intelligenetics, Inc., 700 East El Camino Real, Mountain View, Calif. 94040.

FIG. 18. A. Tabulated results of computer search of PIR and SWISS-PROT databases utilizing Ribonuclease A Bovine as the query sequence. Active site residues which were previously utilized to construct a synthetic catalytic ribonuclease peptide are indicated across the top of the Figure along with the sequence number based upon the ribonuclease linear sequence. To the left of the Figure numbered references are indicated which refer to the sequences listed in B below. For each such sequence, divergences from the active site residue utilized to obtain ribonuclease activity are shown. B. The first 100 sequences demonstrating varying degrees of sequence homology with the query sequence. Homology searching was accomplished using FastDB-Fast Pairwise Comparison of Sequences (Release 5.4) by Intelligenetics, Inc., 700 East El Camino Real, Mountain View, Calif. 94040.

FIG. 19. A. Tabulated results of computer search of PIR and SWISS-PROT databases utilizing Urokinase—Human as the query sequence. Active site residues which were previously utilized to construct a synthetic catalytic urokinase peptide are indicated across the top of the Figure along with the sequence number based upon the urokinase linear sequence. To the left of the Figure numbered references are indicated which refer to the sequences listed in B below. For each such sequence, divergences from the active site residue utilized to obtain urokinase activity are shown. B. The first 100 sequences demonstrating varying degrees of sequence homology with the query sequence. Homology searching was accomplished using FastDB-Fast Pairwise Comparison of Sequences (Release 5.4) by Intelligenetics, Inc., 700 East El Camino Real, Mountain View, Calif. 94040.

DESCRIPTION OF PREFERRED EMBODIMENTS

INTRODUCTION

Figure 1:
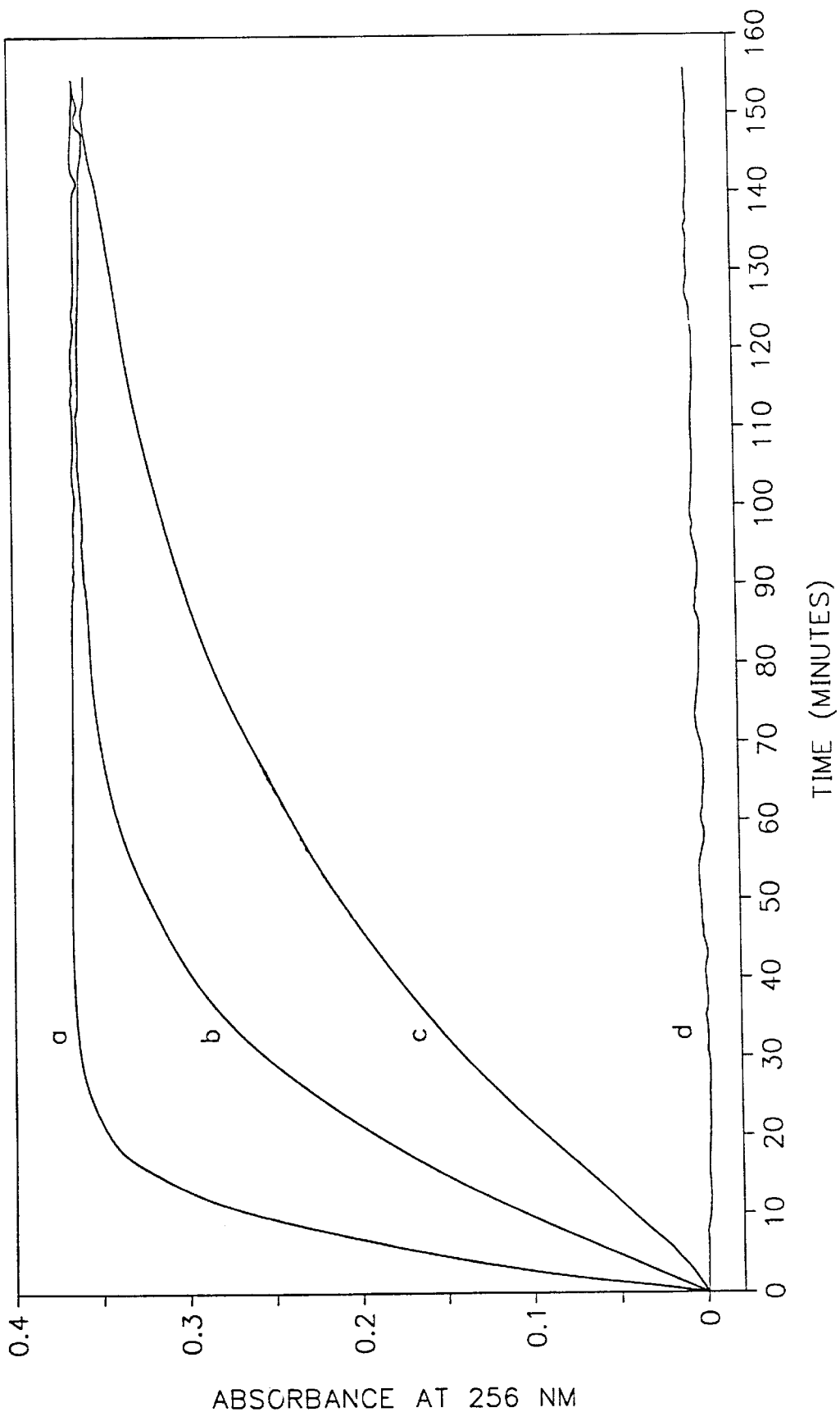
FIG. 1. Time-course hydrolysis of BTEE by αCT and ChPepz. Hydrolyses were carried out, as described in the test, on 200 μg (0.638 μmole) of BTEE, and monitored on a recording spectrophotometer by increase in absorbance at 256 nm, using (a) 1.5 μg ($6.05 \times 10^{-5}$ μmole) αCT; (b) 7.06 μg ($2.65 \times 10^{-3}$ μmole) ChPepz; and (c) 4.71 μg ($1.77 \times 10^{-3}$ μmole) ChPepz. Curve (d) represents the following reactions, all of which had zero activity and superimposed on the x axis: ChPepz (7.06 μg) inhibited with TPCK or with DIFP; ChPepz (7.06 μg) made acyclic by reduction of the disulfide bond; Trypsin or TrPepz action on BTEE; αCT or ChPepz action on TAME; and action of unrelated peptide controls on BTEE.

The Applicant has now constructed by way of example a number of catalytically active synthetic peptide catalysts that duplicate the catalytic activities and specificities of various enzymes. The ability to construct at will fully functional peptide catalysts having the activity and specificity chosen by the investigator should find vast applications.

The disclosure describes two catalyst designs that mimic the activities and specificities of $\alpha$CT and trypsin, both enzymes being proteases. Two 29-residue peptides were prepared, one of which (ChPepz) was designed by surface-simulation synthesis to mimic the active site of $\alpha$-chymotrypsin ($\alpha$-CT), while the other (TrPepz), which contained four substitutions relative to ChPepz, was fashioned after the active site of trypsin. The peptides were each cyclized by a disulfide bond. The ChPepz monomer effected hydrolysis of the ester group in N-benzoyl-L-tyrosine ethyl ester (BTEE), an $\alpha$CT substrate, with $K_m$ and $k_{cat}$ values that were comparable to those of $\alpha$CT. ChPepz was completely inactivated by diisopropyl fluorophosphate (DIFP), L-1-p-tosylamino-2-phenylethyl chloromethyl ketone (TPCK) or reduction of the disulfide bond. It had no catalytic activity on N-tosyl-L-arginine methyl ester (TAME), a trypsin substrate. On the other hand, TrPepz, which had no effect on BTEE, hydrolyzed TAME with a $K_m$ value that was essentially identical to that of trypsin, while its $k_{cat}$ value was almost half that of the enzyme. TrPepz was fully inactivated by reduction of the disulfide bond, by DIFP or by PMSF but not by TPCK. It was also completely inhibited by soybean trypsin inhibitor, bovine pancreatic trypsin inhibitor and human $\alpha_1$-antitrypsin. ChPepz and TrPepz hydrolyzed proteins (myoglobin and casein) to give panels of peptides that were similar to those of the same protein obtained with the respective enzyme. However, TrPepz was more efficient than trypsin at hydrolysing the C-bonds of two or more consecutive lysine and/or arginine residues. Finally, like the esteratic activity, the proteolytic activity of ChPepz was inhibited by DIFP or TPCK while that of TrPepz was inhibited by DIFP or PMSD but not by TPCK.

To ensure that the ability to construct peptide enzymes was not restricted to the two aforementioned proteolytic enzymes, Applicant synthesized two catalysts which were designed by surface-simulation to mimic the active sites of hen egg lysozyme (LYZ) and bovine ribonuclease A (RNase). The former (LyPepz), a 37-residue peptide cyclized by an intramolecular disulfide bond, exhibited the muramidase activity and specificity typical of LYZ. LyPepz was able to effect complete hydrolysis of the cell wall of *Micrococcus lysodeikticus* with a $K_m$ value that compared well with that of LYZ, while its $k_{cat}$ value was 6.7 times lower than that of the whole enzyme. Like LYZ, LyPepz was inhibited by imidazole, tryptamine and histamine. LyPepz became completely inactive when rendered acyclic by reduction of the disulfide bond. The 24-residue cyclic (by a disulfide bond) peptide, RnPepz, designed to mimic the active site of RNase was able to completely hydrolyze yeast RNA with a $K_m$ value that was essentially identical to that of RNase, while its $k_{cat}$ value was considerably lower than that of the enzyme. The cyclic structure of RnPepz was important for its activity because the latter was completely lost upon reduction of the disulfide bond. Like RNase, RnPepz was inhibited by heavy metals and by denatured DNA. Finally, LyPepz had no activity on RNA and conversely RnPepz had no muramidase activity.

CHYMOTRYPSIN AND TRYPSIN

General Materials and Methods

Materials. Myoglobin was the major chromatographic component (No. 10) isolated from crystallized sperm-whale myoglobin as described (Atassi, M. (1964) *Nature* (London) 202, 496–498; to the extent that such references provide disclosure which would enhance the ability of the skilled practitioner to practice the invention described herein, all references provided herein are specifically incorporated by reference). BTEE and TAME were obtained from Aldrich Chemical Company. αCT, TPCK-trypsin, BPTI and soybean trypsin inhibitor were from Worthington Biochemical Corporation. Bovine milk β-casein (which contained about 10% α-casein), DIFP, PMSF, and human α1-antitrypsin were from Sigma Chemical Co. Reagents for peptide synthesis and Nα-Fmoc amino acids were obtained from Vega Biotechnologies.

Peptide Synthesis and Cleavage. The rationale for the design of the peptides is given in the Examples. Certain versions of the peptides, ChPepz and TrPepz, were prepared by solid phase synthesis on a benzyloxybenzyl alcohol resin to which 9-fluorenylmethylcarbonyl (Fmoc)-S-tert-butylcysteine had been coupled. The side-chain protecting groups were: aspartic, β-tert-butyl ester; cysteine, S-tert-butyl; histidine, im-trityl; lysine, ε-tert-butoxycarbonyl; serine and tyrosine, O-tert-butyl. The peptides were synthesized and cleaved from the resin by the procedures described elsewhere in detail Atassi, M. Z., Manshouri, T. and Sakata, S. (1991) *Proc. Natl. Acad. Sci. USA* 88, 3613–3617. Synthesis on alkoxybenzyl alcohol resin (Wang resin) proceeds more smoothly (i.e. complete coupling of consecutive amino acids is achieved more rapidly) than on methoxyalkoxybenzyl alcohol resin.

Fully Automatic synthesis has routinely given Applicant inferior products, even with double-coupling of each residue. The product obtained by fully automatic synthesis is very heterogeneous with many components that have deletion and/or additions. Machine synthesis can yield better quality products if synthesis is checked for completeness after each coupling by the ninhydrin reaction on a few beads of the resin and recoupling done and repeated as necessary until the ninhydrin reaction becomes completely negative. Manual synthesis has proven to routinely give a better product in the Applicant's hands. In either case, completion of coupling of each residue was monitored by ninhydrin and recycled as needed until the ninhydrin reaction became negative (certain positions have required 3 or 4 coupling cycles using 3 molar excess of Fmoc-amino acid derivative at each cycle).

Specifically, for cleavage of peptides from the resins, 10 ml of DCM ($CH_2Cl_2$) was added to peptide-resin (1 g) in a sintered-disc reaction vessel. The resin was allowed to swell for about 1 hour. DCM was then removed by $N_2$ pressure and 10 ml of Reagent R (TFA-thioanisole-1,2-ethanedithiol-anisole,9: 5:3:2 vol/vol) was added. The resin was shaken slowly at room temperature for 3 hours after which it was filtered and rinsed twice (7 ml each) with Reagent R. The three filtrates were combined and rotary evaporated under vacuum down to 2–3 ml. The peptide solution thus concentrated was added dropwise to 30 ml cold (0° C.) ether upon which it precipitated. It was shaken gently after addition of 20 ml more of ether. The precipitate was washed with cold ether on the centrifuge five times (20 ml each time), dissolved (or suspended) in water or 25 mM $CH_3COOH$ and freeze-dried (yield of crude product approximately 0.52 g). Care was taken to ensure that tryptophan was not modified during cleavage because thioanisole can cause N-alkylation of tryptophan. Inadvertent alkylation of tryptophan was checked by amino acid analysis of p-toluenesulfonic acid hydrolysates (Liu, T. Y. and Chang, Y. H., *J. Biol. Chem.* 246: 2842 (1971).

To the cleavage product (0.2 g) was then added 2 ml of 25 mM acetic acid. At this concentration, the peptide is not completely soluble. Therefore, it was centrifuged (2500 rpm, 30 min; the residue is saved for another cyclization) and the supernatant was applied to a column (2.5×95 cm) of Sephadex G-15 which had been pre-equilibrated and eluted with 25 mM acetic acid. It is recommended that small molecular weight compounds be removed from the crude cleaved peptide prior to the cyclization step. The tubes containing the peptide were combined and freeze-dried.

Cyclization of the Peptide and Purification of the Monomer. Generally—A portion (50 mg) of the synthetic product was dissolved in 8.0M urea containing 2-mercaptoethanol, preadjusted to pH 8.5 with triethylamine. The solution was stirred gently on a magnetic stirrer for at least 3 hrs at room temperature, after which it was applied on a column of Sephadex G15, which was eluted with 0.025M acetic acid, to remove the urea and mercaptoethanol. The fractions containing the peptide were pooled and diluted with at least 3 liters of 0.025M acetic acid and the pH was adjusted to approximately 8.0 on the pH meter by the addition of triethylamine. The solution was stirred magnetically at room temperature for at least 4 days and then freeze-dried.

Specifically: ChPepz—ChPepz (35 mg) was dissolved in 0.5 ml of 8.0 m urea/10% 2-mercaptoethanol. The solution was allowed to stir at room temperature for 16 hours, after which it was desalted on a column (2.5×95 cm) of Sephadex G-15 which had been pre-equilibrated and then eluted with 0.025M $CH_3COOH$. Fractions containing the peptide were combined and then diluted up to 4 liters having a final acetic acid concentration of 2 mM. After cooling the solution down to 4° C., its pH was adjusted to 7.8–8.0 with triethylamine and allowed to stir for 9–10 days with full exposure to Air (covered with a Kimwipe™ which is secured around the neck of the flask with a rubber band). The pH was then adjusted down to 5.0 with acetic acid and the solution was either flash-evaporated under vacuum (but not allowed to warm up above 30° C.) or freeze-dried.

Reduction was done in 8.0 urea to ensure complete unfolding of polymeric species and thus make the disulfide bonds more accessible to reduction. Concentration of the 2-mercaptoethanol and the duration of the reduction were increased to ensure completeness of the latter.

Cyclization was done under very dilute conditions (6–8 $\mu$g/ml) to minimize inter-molecular disulfide bond formation. Cyclization was done at 2°–4° C. (in the cold room) because chymotryptic activity of ChPepz (and for that matter of chymotrypsin itself) is very negligible at 4° C. This technique avoided auto-hydrolysis of ChPepz. Cyclization was done at pH 7.8–8.0 and never allowed to exceed pH 8.5. Before concentrating the cyclized pepzyme, the pH was necessarily adjusted down to 5.0. This prevented the pepzyme from digesting itself when the solution is concentrated on the flash evaporator. Air oxidation was done slowly. Bubbled oxygen and vigorous agitation was avoided.

Specifically: TrPepz—Procedures were the same as described for ChPepz except that cyclization of TrPepz was done at room temperature. Additionally, at the completion of the cyclization reaction, the pH was adjusted down to 6.0 with acetic acid before the solution was concentrated or freeze-dried.

The dry peptide (approx. 30 mg) was dissolved in 1 ml of 0.25M acetic acid, centrifuged to remove insoluble material, and subjected to ascending chromatography on two columns (90×2.5 cm each) of G50-fine, connected in series and eluted with 0.25M acetic acid. The fractions (2–3 ml) were monitored by absorbance at 230 and 280 nm. The peak of the monomer, eluting at 750 ml, was well resolved from the oligomers which eluted earlier as a single peak. The oligomers were saved for reduction and re-cyclization to obtain more monomer. The tubes containing the monomeric species were pooled and freeze-dried (yields: ChPepz, 26.7%; TrPepz, 33.2%).

Alternatively, the cyclized product (4–5 mg) was fractionated by HPLC on a Phenomenex Polysep 2000 molecular sizing column (7.8×600 mm). The column was eluted at the rate of 0.5 ml/min (0.5 ml per fraction) with 5 mM acetic adjusted to pH 5.5 with triethylamine. The chromatographic operation was repeated about 12 times, with 4–5 mg being applied on the column each time and the effluent of each run was collected in the tubes of the respective elution time. The fractions belonging to each peak were combined, freeze-dried and tested for activity with BTEE. The fraction eluting at 50 minutes, which corresponds to the cyclic monomer, possessed some activity and was further purified by reverse phase HPLC. Yield of monomer using this method was approximately 18–33%.

Generally, the monomer was further purified by HPLC on a 5 $\mu$m $C_{18}$ column (10 mm ID×25 cm) using a gradient of 0.05% acetic acid-triethylamine pH 5.5, and acetonitrile in 0.05% acetic acid (9:1 vol/vol). The fractions were monitored by absorbance at 256 nm and by their hydrolytic activity toward BTEE (for ChPepz) or TAME (for TrPepz). The active fraction was freeze-dried and reapplied on the same column using a gradient of 0.1% acetic acid and acetonitrile in 0.1% acetic acid (9:1 vol/vol). The catalytically-active fractions (yields: ChPepz, 12.1%; TrPepz, 11.5%, of the monomer) were homogeneous by high voltage paper electrophoresis and by analytical HPLC and their amino acid compositions were in excellent agreement with those expected from their covalent structures.

Specifically, the further purification by reverse-phase HPLC of ChPepz monomer was accomplished as follows:

The monomeric fraction was further purified by reverse-phase HPLC as follows:

Column: C18, semi-preparative, 10 mm×25 mm (Rainin)
(1) Chromatography No.1: Monomer prepared above was further purified by reverse phase HLPC
  Solvent A: 0.05M acetic acid, adjusted to pH 5.5 with triethylamine.
  Solvent B: 90% acetonitrile+10% solvent A
  Gradient:
  0–15% B, 5 min
  15–35% B, 25 min
  35–60% B, 5 min
  60–80% B, 5 min
  Nine peaks were obtained, peak 9 exhibited hydrolytic activity on BTEE Peak 9 was reapplied on the same column.
(2) Chromatography No.2
  Solvents A and B, same as in chromatography no. 1
  0–35% B, 10 min
  35–60% B, 25 min.
  60% B, 5 min
  Peak 9 (from chromatography #1) was resolved into 11 peaks. Activity towards BTEE resided in peak 5.
  Peak 5 was reapplied on the same column (chromatography no. 3)
(3) Chromatography No. 3
  Solvents A and B, same as in chromatography no. 1
  100% A (0% B). 1 min
  0–15% B, 8 min
  15–27% B, 30 min
  27–30% B, 5 min
  Activity resided in peak 4
  Recovery peak 4—5.18%–12.06% of monomer, depending on the synthesis.

Specifically, the further purification by reverse-phase HPLC of TrPepz monomer was accomplished as follows:

The monomeric fraction was further purified by reverse-phase HPLC Column: C-18, semi-preparative 10 mm×25 mm (Rainin)

(1) Chromatography No. 1: Monomer prepared above was subjected to reverse-phase HPLC.
  Solvent A: 0.3% acetic acid in water, adjusted to pH 5.5 with TEA
  Solvent B: Acetonitrile—solvent A (9:1), vol/vol)
  Elution gradient:
  0–15% B, 5 min.
  15–35% B, 25 min.
  35–60% B, 5 min.
  60–80% B, 5 min.
  At least 19 peaks are obtained. Peak 18 possessed hydrolytic activity towards tosyl-L-arginine methyl ester (TAME)
  Peak 18 was reapplied on the same column
(2) Chromatography No. 2
  Solvent A: 0.1% acetic acid in water, adjusted to pH 5.5 with triethylamine
  Solvent B: Acetonitrile—Solvent A (9:1, vol/vol)
  Elution gradient:
  0–35% B, 10 min.
  35–60% B, 25 min.
  60% B, 5 min.
  Thirteen peaks were obtained (of which peaks 1, 5, 6 and 7 were major). Most of the activity towards TAME coincided with peak 7.
  Peak 7 was reapplied on the same column.
(3) Chromatography No. 3
  Solvent A: 0.1% acetic acid in water, adjusted to pH 5.5 with triethylamine
  Solvent B: Acetonitrile in solvent A (9:1, vol/vol)
  Elution gradient:
  0–15% B, 8 min.
  15–27% B, 30 min.
  27–30% B, 5 min.
  Peak 7 from chromatography no. 2 was found to be essentially pure giving four very minor peaks and one major peak (peak no. 5). Peak 5 accounted for 89.9% of the total. Further purification of peak 5 was unnecessary. Yield of peak 5 was between 5.4 to 12.0% of the monomer, depending on the synthesis. Molecular weight calculations and purity determinations may also be accomplished by electrospray and/fast atom bombardment mass spectroscopy.

Measurement of Catalytic Activity

Chymotryptic activity. The catalytic activity of $\alpha$CT and CHPepz was determined by hydrolysis of BTEE in 0.08M Tris buffer, pH 7.8 containing 0.01M $CaCl_2$ as described (Hummel, B. C. W. (1959) *Can. J. Biochem. Physiol.* 37, 1393–1399). Assays were done at 25° C. using $8.06 \times 10^{-4}$ $\mu$moles of $\alpha$CT or $7.49 \times 10^{-4}$ $\mu$moles of ChPepz and different substrate concentrations (from 3 to 6 mM) in a total reaction volume of 1.0 ml. The change of absorbance at 256 nm was monitored on a recording spectrophotometer against a reference cuvette containing 1 ml of the same concentration of BTEE, but without $\alpha$CT or ChPepz. Controls included trypsin, TrPepz (which are inactive against BTEE) and several linear and cyclic peptides from Applicant's peptide library although any such controls would work equally as well.

Specifically, reagents and procedures used to measure chymotryptic activity were as follows:

Reagents:
  a. 0.08M Tris-HCl, containing 0.01M $CaCl_2$, pH 7.8
  b. N-Benzoyl-L-tyrosine ethyl ester (BTEE) dissolved in 50% (w/w) Methanol (63 ml $CH_3OH$+50 ml water). Assay points in the range 90–180 $\mu$g per assay were used.
  c. ChPepz in 0.001N HCl. 1–10 $\mu$g was used.
  d. Negative controls: several peptides that are unrelated to ChPepz were used. Solutions of these control peptides were made in the same solvent ($10^{-3}$N HCl) and at the same concentrations as ChPepz and test samples.

e. α-chymotrypsin (αCT)(positive control). 1–5 μg was used. Importantly, it was critical to always dedicate a separate cuvette for this positive control to ensure no cross-contamination.

f. Total reaction volume 1.01 ml.

1.0 ml of substrate (BTEE) was mixed with solutions (10 μl aliquots) of ChPepz, or negative control peptides (containing 1–10 μg/10 μl) or αCT and activity was monitored by increase in absorbance at 256 nm at 37° C. (or at room temperature).

ChPepz solution was made in $10^{-3}$N HCl, since it will not digest itself in this solvent. Solutions of ChPepz were always made immediately before use. Activity was typically lost on storage in solution (completely lost in 2 days at 4° C.). Activity was typically lost by freezing and thawing (completely lost after 5 such cycles). ChPepz will not act on chromogenic substrates—it was inhibited by p-nitroaniline, analine and benzamidine (and is probably inhibited by other aromatic compounds). After mixing ChPepz with substrate (BTEE), there was typically a lag of 2–5 min (depending on pepzyme/substrate ratio) before any change in $A_{256}$ was observed. However, in the early stages of the purification, the activity needed to be monitored over a period of several hours. It was important to ensure that negative controls (containing unrelated peptides in amounts similar to those of ChPepz in the test samples) were also monitored at the same time because the background absorbance will increase and the test samples had to be corrected for this background. As the sample's purity improves, maximum $A_{256}$ was achieved more quickly. See, e.g., Atassi, M. Z. in *Immunochemistry of Proteins*, ed. M. Z. Atassi, Vol. 2, pp. 77–176, Plenum, New York, N.Y. (1977); King, D. S., et al. *Int. J. Pept. Prot. Res.* 36: 255–266 (1990).

Tryptic activity. Measurement of tryptic activity was done in 0.046M Tris-HCl buffer, pH 8.0, containing 0.0115M $CaCl_2$ as described (Hummel, B. C. W. (1959), id) using TAME as the substrate. For the assays, $8.4 \times 10^{-4}$ μmoles of αCT or 1.6 c $10^{-3}$ μmoles of TrPepz were allowed to hydrolyze different amounts of substrate at 25° C. in a total reaction volume of 1.0 ml. Hydrolysis was monitored on a recording spectrophotometer by change in absorbance at 247 nm against a reference cuvette containing the same concentration of TAME, but without trypsin or TrPepz. αCT, ChPepz (which do not hydrolyze TAME) and several linear and cyclic peptides from Applicants library were used as controls although others would work as well. Kinetic constants for hydrolysis of BTEE and TAME were determined from the linear plots of 1/initial velocity (Vi in μmoles/min) versus 1/substrate concentration as described (Lineweaver, H. and Burk, D. (1934) *J. Amer. Chem. Soc.* 56, 658).

Specifically, reagents and procedures used to measure tryptic activity were as follows:

Reagents:
a. 0.046M Tris-HCl, containing 0.0115M $CaCl_2$, pH 8.0.
b. Tosyl-L-arginine methyl ester (TAME)
c. Solutions of TAME were made in the Tris-HCl buffer noted in a. Assay points in the range 100–200 μg TAME/ml were used.
d. TrPepz in the Tris-HCl buffer noted in a. 1–10 μg was used in each assay.
e. Negative controls: several peptides unrelated to TrPepz. Solutions in the Tris-HCl buffer were made and at the same concentrations as the TrPepz test samples.
f. Trypsin-TPCK (positive control). 1–5 μg were used in each assay. Applicant always dedicated a separate cuvette for this.

g. Total reaction volume 1.01 ml.

To TAME solutions (1 ml containing different amounts of substrate), an aliquot (10 μl) of TrPepz, or negative control peptide solutions (containing 1–10 μg/10 μl) was added, mixed immediately and the increase of absorbance at 247 nm was measured at 37° C. (or at room temperature).

TrPepz solutions were always made immediately before use. Although TrPepz has no potential tryptic cleavage points, it lost activity on standing in solution at 4° C. (activity was completely lost in two days). Activity was lost by freezing and thawing (completely lost after 5 such cycles). TrPepz will not act on chromogenic substrates—it was inhibited by p-nitro analine (and probably is inhibited by other aromatic amines). After mixing TrPepz with substrate, there was a lag of 2–5 minutes (depending on pepzyme/substrate ratio) before any change in $A_{247}$ was observed. In the early stages of the purification, the activity was always monitored over a period of several hours. Negative controls (containing unrelated peptides in amounts similar to those of TrPepz in the test samples) were also monitored at the same time because the background absorbance will increase and the test samples had to be corrected for this background. As the sample's purity improved, maximum $A_{247}$ was achieved more quickly.

Inhibition of Enzymatic Activity. The effects of inhibitors or disulfide bond reduction on enzymatic activities were done as described above except that the enzymes were pre-mixed (3 hrs, 25° C.) with 10 molar excess of inhibitor (or DTT) prior to addition to the substrate (140–150 molar excess relative to the catalyst). Activities were monitored spectrophotometrically as above and were compared to uninhibited controls.

Hydrolysis of Proteins by Enzymes or Peptide Enzyme Catalysts. Hydrolyses were done at 37° C. on aliquots (200 μl) containing 1 mg of myoglobin ($5.6 \times 10^{-2}$ μmoles) or casein ($4.2 \times 10^{-2}$ μmoles) in 0.1M triethylamine-acetic acid buffer, pH 8.0 with 51 μg of αCT ($2.06 \times 10^{-3}$ μmoles) and 2.9 μg of ChPepz ($1.1 \times 10^{-3}$ μmoles) for 3½ hrs or with 49 μg trypsin ($2.06 \times 10^{-3}$ μmoles) and 5.0 μg TrPepz ($1.87 \times 10^{-3}$ μmoles) for 8 hrs. The samples were then acidified (to pH 3.0) with 0.1M HCl freeze-dried and redissolved in 100 μl of $H_2O$ at pH 3.0, and the entire sample was applied as a single spot to Whatman No. 3MM paper and subjected, in the first dimension, to ascending chromatography in n-butanol-acetic acid-water (4:1:5, vol/vol) followed by high voltage electrophoresis (3000 volts, 55 min), in the second dimension, in pyridine-acetic acid-water (1:10:289, vol/vol), pH 3.65, as described (Atassi, M. Z. and Saplin, B. J. (1968) *Biochemistry* 7, 688–698). The papers were then dried, steamed and stained with 0.2% ninhydrin in ethanol and the color was allowed to develop at room temperature. The papers were photographed 48 hrs after staining.

Chymotrypsin and Trypsin Examples

Example I: Hydrolysis of Ester Substrates by αCT and ChPepz

Figure 2:
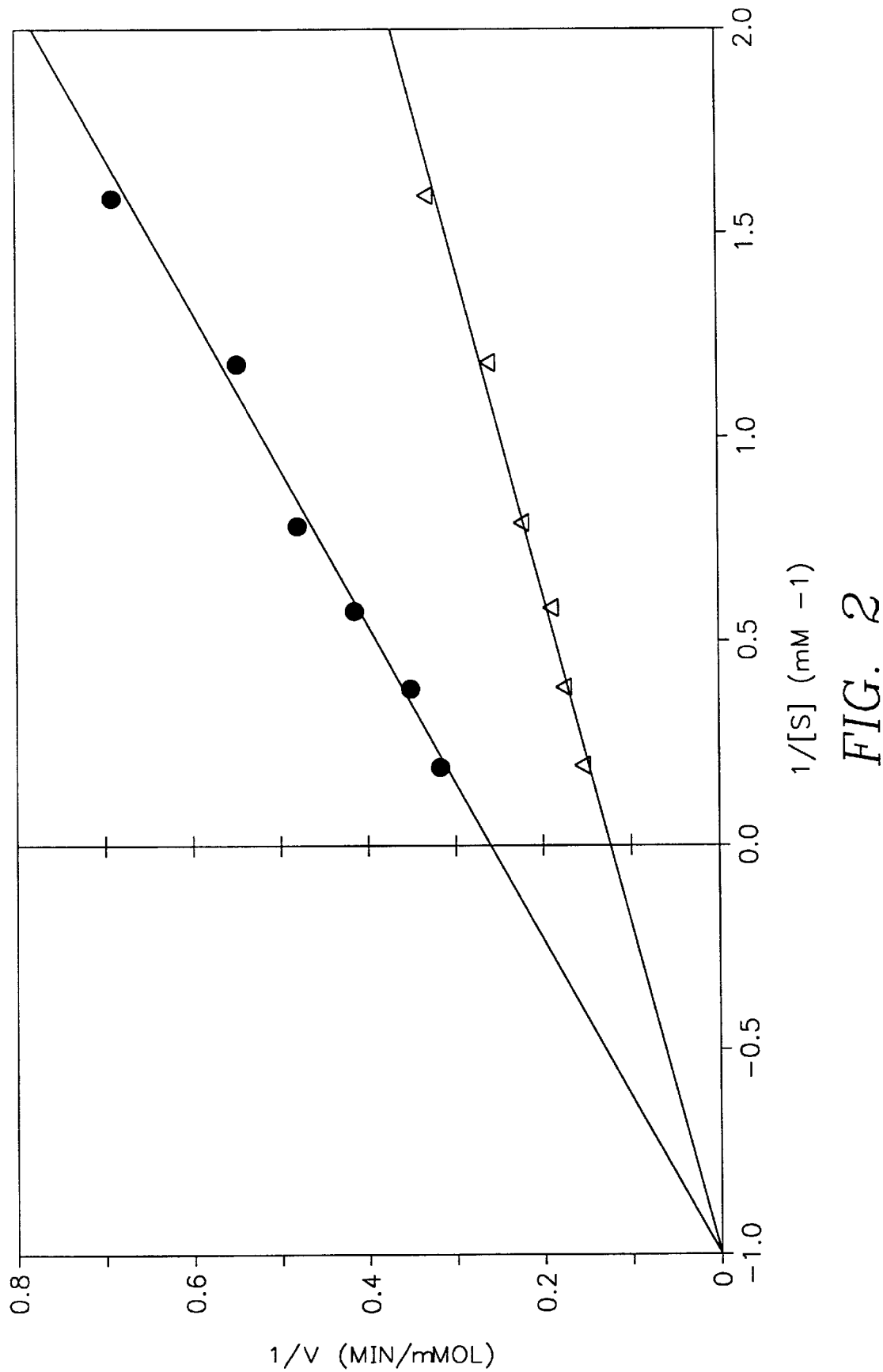
FIG. 2. Examples of Lineweaver-Burk plots for BTEE hydrolysis by ChPepz (●), and αCT (Δ). Assays were carried out at pH 7.8 and 25° C., in 306 replicates at six different substrate concentrations as described in the text. The $K_m$ and $k_{cat}$ values obtained from these plots are given in Table 1 together with the kinetic constants for the action of trypsin and TrPepz on TAME.

Like αCT, the action of ChPepz on BTEE caused hydrolysis of the ester bond (FIG. 1). Lineweaver-Burk plots (FIG. 2) of experiments at different substrate concentrations showed that the kinetic constants of the hydrolysis of BTEE by αCT and by ChPepz were comparable (Table 1). The values of $K_m$ (a measure of substrate affinity) for ChPepz and αCT were almost identical, while the $k_{cat}$ value for ChPepz was only slightly lower than that of αCT. The specificity constants $k_{cat}/K_m$) for BTEE with αCT and ChPepz were also quite comparable (Table 1). The activity of ChPepz was completely inhibited by the αCT inhibitors, TPCK and DIFP, and also completely lost when rendered acyclic by reduction of the disulfide bond. ChPepz had no hydrolytic activity on TAME (which is a trypsin substrate) and, as mentioned below, TEE was not hydrolyzed by TrPepz or by control cyclic and linear peptides that are not related to αCT.

TABLE 1

Kinetic constants for hydrolysis of BTEE by αCT and ChPepz and of TAME by trypsin and TrPepz[1,2]

|  | $K_m$ (M × 10$^{-3}$) | $k_{cat}$ (sec.$^{-1}$) | $k_{cat}/K_m$ (M$^{-1}$Sec$^{-1}$) |
|---|---|---|---|
| Hydrolysis of BTEE by: |  |  |  |
| ChPepz | 1.11 ± 0.15 | 147 ± 8.5 | 1.32 × 10$^5$ |
| αCT | 1.07 ± 0.16 | 185 ± 10.3 | 1.72 × 10$^5$ |
| Hydrolysis of TAME by: |  |  |  |
| TrPepz | 2.42 ± 0.09 | 85 ± 2.6 | 3.5 × 10$^4$ |
| Trypsin | 2.56 ± 0.16 | 221 ± 9.7 | 8.6 × 10$^4$ |

[1] Values of the constants for ChPepz and αCT were obtained at pH 7.8 and 25° C. while those for TrPepz and trypsin were derived from measurements at pH 8.0 and 25° C. For details, see the text. $k_m$ and $k_{cat}$ values for whole enzymes in general agreement with reported values. See, e.g., Martin, C. J., et al., J. Biol. Chem. 234: 1718–1725 (1959); Ronwin, E., Biochem. Biophys. Acta 33: 326–332 (1959); Hummel, B. C. W. Can. J. Biochem. Physiol. 37: 1393–1399 (1959); Hartley, B. S., in Structure and Activity of Enzymes, pp. 47–60, Academic Press, New York, NY (1964); Hahn, K. W. et al., Science 248: 1544–1547.
[2] Note that BTEE is not hydrolysed by trypsin or TrPepz and TAME is not hydrolysed by αCT or ChPepz.

Example II: Activity of TrPepz on Ester Substrates

Figure 3:
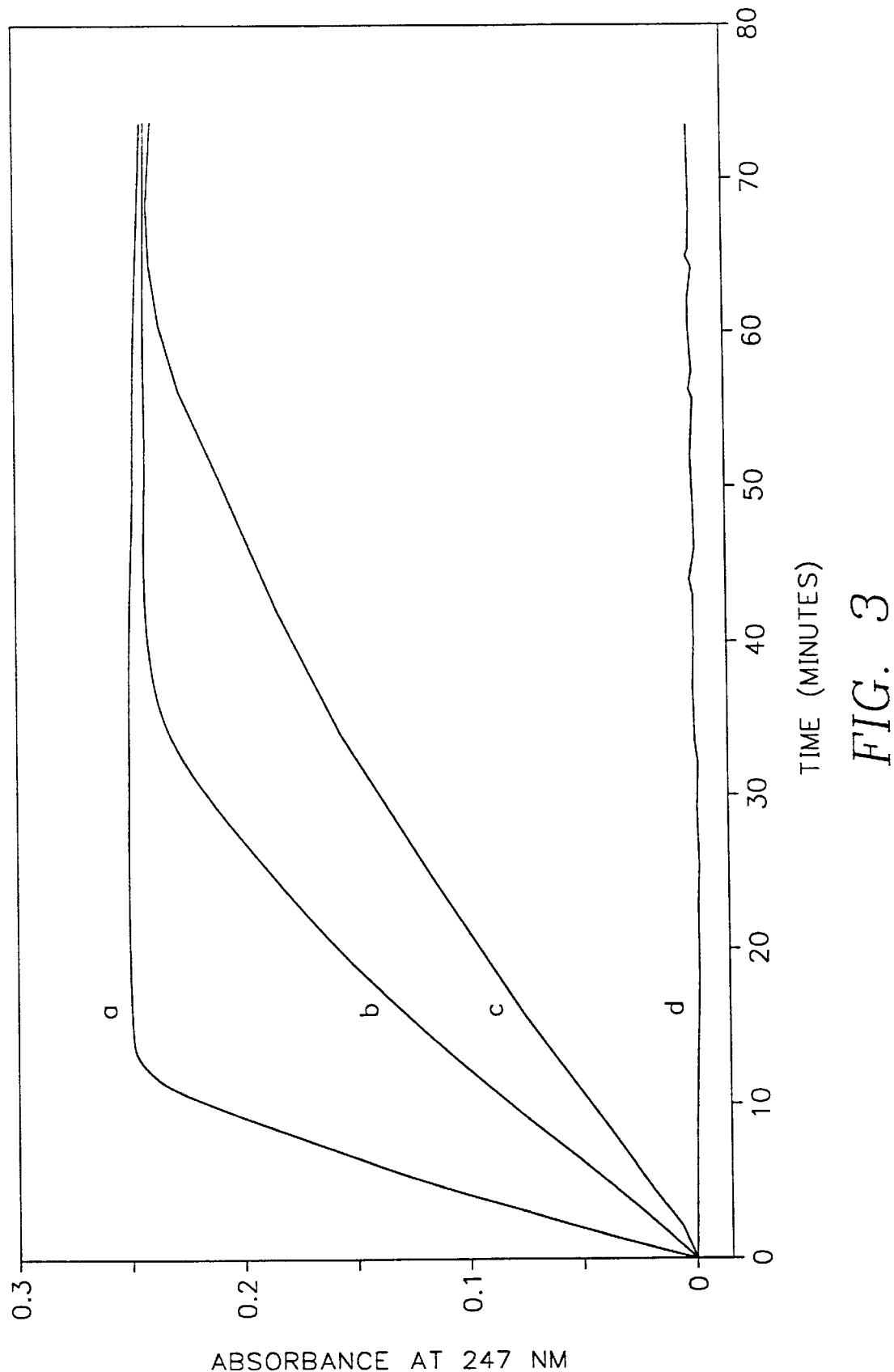
FIG. 3. Hydrolysis of TAME by trypsin and TrPepz. Reactions were done on 240 μg (0.634 μmole) of TAME at 25° C., pH 8.0, in a total reaction of 1 ml and monitored at 247 nm on a recording spectrophotometer, as described in the text. Hydrolyses were done with: (a) trypsin ($2.1 \times 10^{-5}$ μmoles); (b) 6.84 μg of TrPepz ($2.53 \times 10^{-3}$ μmoles), both in the presence and absence of 10 molar excess of TPCK (the two curves superimposed) (c) 4.55 μg of TrPepz ($1.69 \times 10^{-3}$ μmoles); (d) several reactions superimposed on this zero activity curve. These are: action of ChPepz (7.0 μg) on TAME, effect of control cyclic and linear peptides (unrelated to TrPepz or ChPepz) on TAME, TrPepz (6.84 μg) inactivated by reduction with DTT or inhibited by 10 molar excess of PMSF, DIFP, BPTI or human $\alpha_1$-antitrypsin.

In its action on TAME, TrPepz exhibited an activity which was very much like that of trypsin. Lineweaver-Burk plots of reactions at different substrate concentrations showed that TrPepz had an affinity for the substrate ($K_m$) which was similar to that of trypsin. It hydrolyzed TAME at a rate which was about 40% relative to the rate obtained with the enzyme itself (Table 1). The hydrolytic activity of TrPepz on TAME was completely lost by reduction of the disulfide bond. The activity of TrPepz on TAME was completely lost by reduction of the disulfide bond. The activity was also inhibited entirely by DIFP, PMSF, soybean trypsin inhibitor, BPTI and human α$_1$-antitrypsin (FIG. 3). On the other hand, the activity was not affected by TPCK. TrPepz had no effect on BTEE and, an mentioned above, TAME was not hydrolyzed by ChPepz or by control unrelated (to trypsin) cyclic or linear peptides. Thus, the replacement of residues converted the catalyst activity from chymotryptic to tryptic.

Example III: Proteolytic Activity of ChPepz

Figure 4:
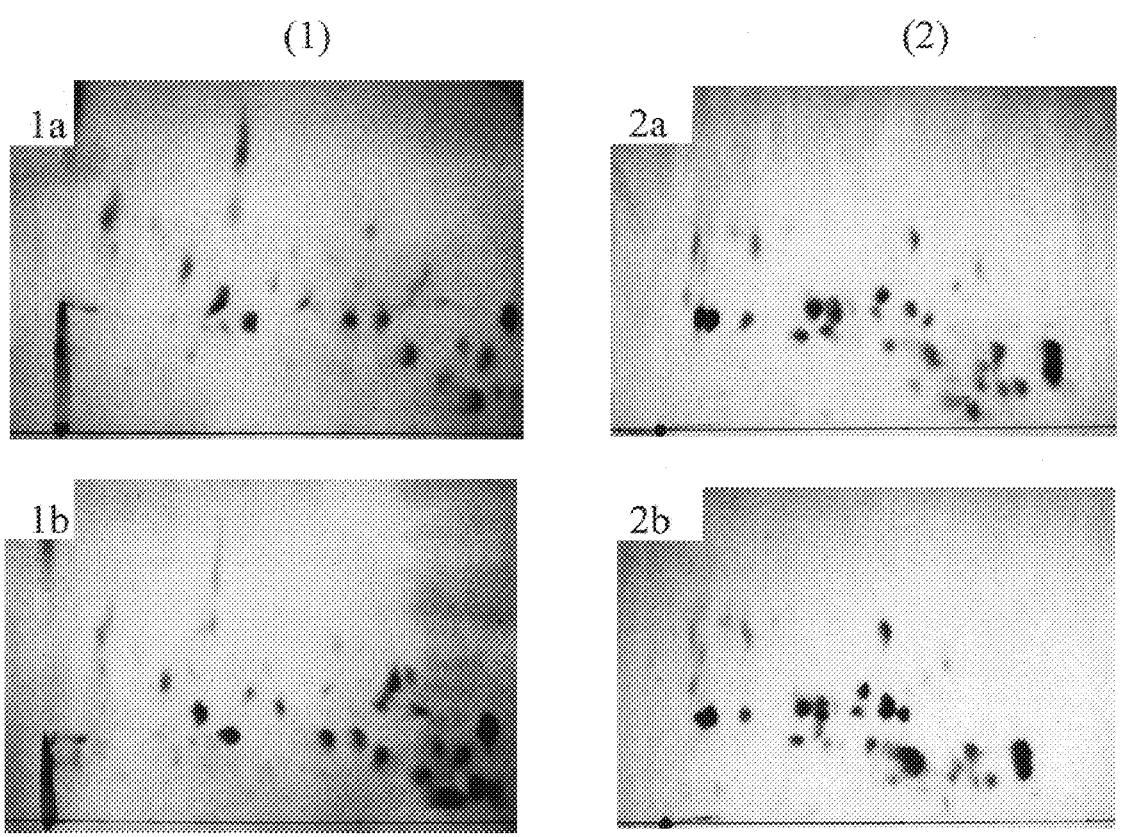
FIG. 4. Maps of the peptides obtained from (1) myoglobin and (2) casein by hydrolysis with αCT or ChPepz. (1a) myoglobin peptides obtained with αCT; (1b) myoglobin peptides obtained with ChPepz; (2a) Casein peptides obtained with αCT; (2b) casein peptides obtained with ChPepz. Peptide maps were done, as described in the text, by chromatography in the descending dimensions followed by high voltage paper electrophoresis (from left to right).

To confirm that the ability of the two synthetic catalysts to hydrolyze, in a specific manner, the correct amino acid ester substrate was a true proteolytic activity, it was necessary to examine their action on peptide and protein substrates. The action of ChPepz on Mb and casein resulted in the hydrolysis of the respective protein by αCT (FIG. 4). The hydrolysis of the proteins by ChPepz was quite efficient and was achieved in a time-frame that was enzyme-like. The activity of ChPepz on protein substrates was completely inhibited by TPCK.

Example IV: Proteolytic Activity of TrPepz

Figure 5:
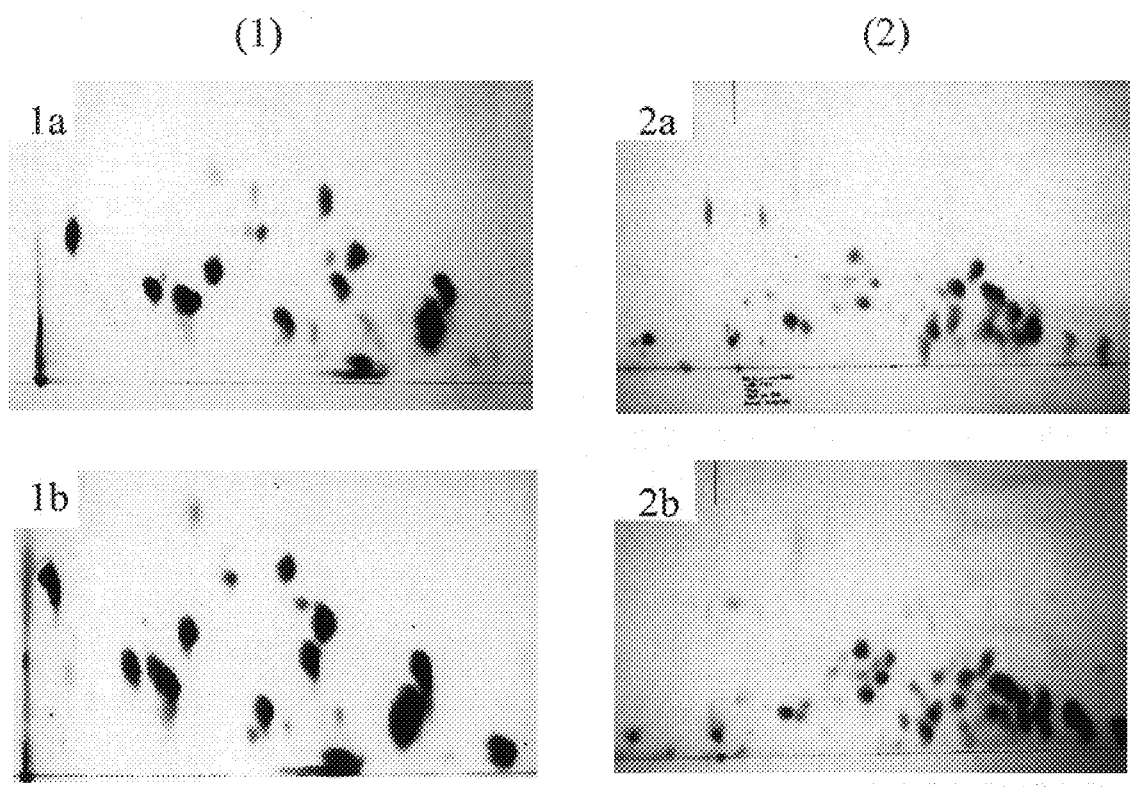
FIG. 5. Fingerprints of the myoglobin and casein peptides obtained by hydrolysis with trypsin or TrPepz. (1) myoglobin peptides obtained by hydrolysis with: (1a) trypsin, or (1b) TrPepz; (2) casein peptides obtained with (2a) trypsin, or (2b) TrPepz. Peptide maps were done by paper chromatography in the ascending dimension, followed by high voltage paper electrophoresis (from left to right). For details, see the text.

In order to further ascertain that TrPepz behaved like trypsin in activity and possessed its specificity, it was tested on model peptides and proteins. Its action (3 hrs; molar ratio of substrate/TrPepz, 1:60) on the peptide Gln-Leu-Glu-Pro-Ser-Thr-Ser-Ser-Ala-Val-Pro-Leu-Ile-Gly-Lys-Gly (SEQ ID NO:7) resulted in almost complete (over 95%) hydrolysis of the Lys-Gly bond. The lysozyme sequences: Ala-Ala-Met-Lys-Arg-His-Gly-Leu-Asp-Asn (SEQ ID NO:8), Asp-Asn-Tyr-Arg-Gly-Tyr-Ser-Leu-Gly (SEQ ID NO:9), Ala-Lys-Lys-Ile-Val-Ser-Asp-Gly (SEQ ID NO:10) were completely cleaved by TrPepz at the C-bond of the lysine and arginine residues indicated. No other products were obtained. The proteolytic activity of TrPepz was investigated on two proteins, myoglobin and casein. In each case, the peptide pattern of the TrPepz hydrolysate was essentially the same as the pattern of the respective protein obtained by tryptic hydrolysis (FIG. 5). However, TrPepz was in fact more efficient at hydrolyzing Lys-Lys, Lys-Lys-Lys, Arg-Lys and Lys-Arg bonds as evident from the higher yields of lysine and arginine in hydrolyses by Trpepz, as compared to those by trypsin. Finally, the proteolytic action of TrPepz, like that of trypsin, was completely inhibited by DIFP or PMSF while TPCK had no effect.

Design of the Synthetic Peptide Catalysts

As stated above, a surface-simulation synthetic peptide was constructed (Atassi, M. Z., Biochem. J. 226: 477–485 (1985)) that possessed the expected binding activities of trypsin with substrates and inhibitors but had no significant catalytic activity. Nevertheless, the ability to produce substrate binding encouraged Applicant to improve the designs to achieve an enzymically active peptide. Applicant made 10 design changes. The following cyclic peptide designs were active (shown here for the trypsin active site): design 1, Cys-Asp-Ser-Gly-Gly-Val-Ser-Trp Gly-Gly-Leu-Gly-Asp-Gly-Ala-Ala-His-Gly-Gly-Phe-His-Tyr-Cys (SEQ ID NO:11); design 2, Asp-Ser-Gly-Gln-Cys-Asp-Ser-Gly-Gly-Val-Ser-Trp-Gly-Gly-Leu-Gly-Asp-Gly-Ala-Ala-His-Gly-Gly-Phe-His-Tyr-Cys (SEQ ID NO:12); design 3, Cys-Phe-Gly-Gly-Ser-Asp-Gly-Gln-Gly-Ser-Asp-Gly-Gly-Val-Ser-Trp-Gly-Leu-Gly-Gly-Asp-Gly-Ala-Ala-His-Cys (SEQ ID NO:13) (active site residues are underlined; others are spacers). Under the conditions described above, the rate of hydrolysis of TAME by the final TrPepz design (FIG. 7) was better than designs 1–3 by 250, 123, and 72 times, respectively. The peptide maps of 144-hr Mb or casein hydrolysates by designs 2 and 3 compared well to the respective tryptic hydrolysates. The cyclic structures of designs 1–3 were essential for activity. Similar results were obtained with the corresponding analogs of the αCT active site.

Example V: Surface Simulation of Chymotrypsin Active Site

Figure 6A:
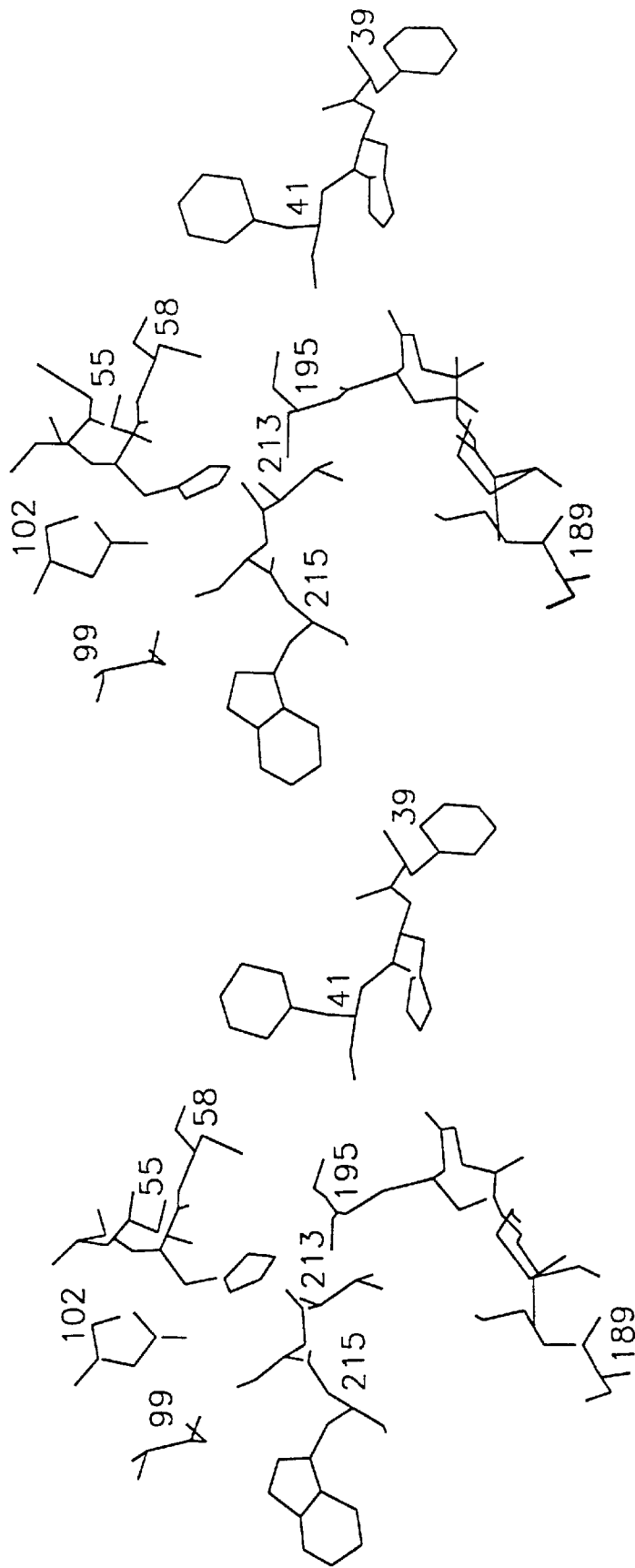
FIG. 6. Stereo-diagram showing the active site residues of (A) bovine αCT and (B) bovine trypsin. Four residues in the active site of αCT are substituted in trypsin (Phe-39 to Tyr, Ile-99 to Leu, Ser-189 to Asp, Met-192 to Gln) and shown in heavy lines in (B).
Figure 7A:
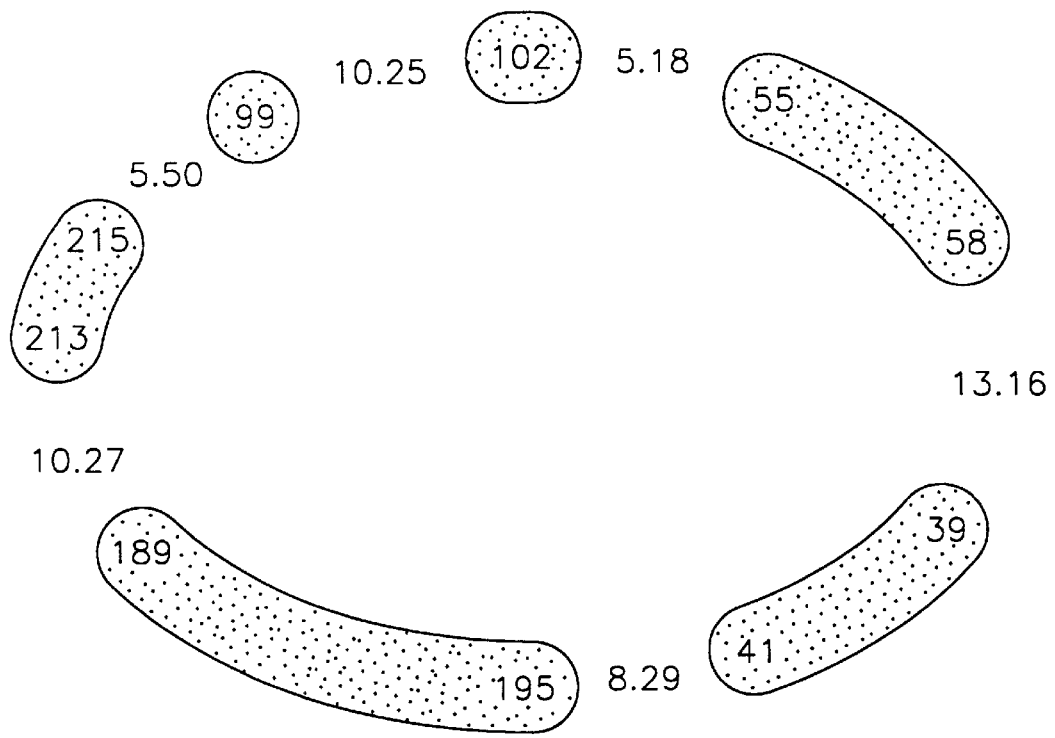
FIG. 7. Design of the surface-simulation synthetic peptides mimicking the active sites of α-chymotrypsin (ChPepz) and trypsin (TrPepz). (a) shown the contact residues of the active site in the shaded areas and the distances ($C^\alpha$-to-$C^\alpha$, in Å) separating the appropriate residues. Residue numbers are based on bovine chymotrypsinogen sequence. (b) indicates the surface-simulation synthetic peptides designed to mimic the active sites. The residues in the shaded areas are the actual active site residues of bovine αCT while those linking these shaded areas are glycine spacers introduced to achieve appropriate distances of separation between the respective residues and regions of the site. (Cter) is the C-terminal Cys and (Nter) denotes the N-terminal Cys of the peptides which are cyclized by the disulfide between the two Cys residues. The outer sequence differs from ChPepz in four positions only: Phe-39 to Tyr, Ile-99 to Leu, Ser-189 to Asp, Met-192 to Gln.
Figure 7B:
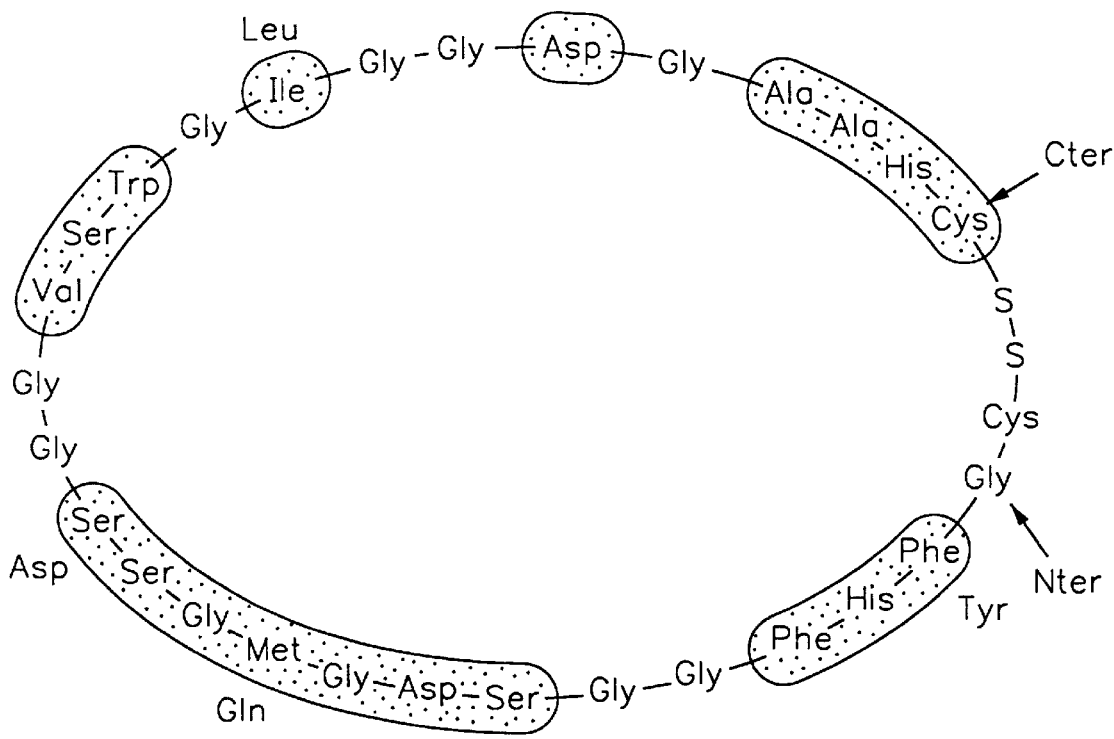

The essential residues of the active sites of αCT and trypsin are shown in FIG. 6. These residues have been implicated as essential parts of the active site by chemical and crystallographic evidence which has been reviewed (Atassi, M. Z. (1985) Biochem. J. 226, 477–485). FIG. 7 shows that position of the contact residues in the sequence (using bovine chymotrypsinogen sequence numbers) and the distances (in Å) separating them. The sequence was obtained from reference (Meloun, B., Kluh, I., Kosta, V., Moravek, L., Prusik, Z., Vanecek, J., Keil, B. and Sorm, F. (1966) Biochim. Biophys. Acta 130, 543–546) and the X-ray coordinates are known to 1.68 Å resolution (Tsukada, H. and Blow, D. M. (1985) J. Mol. Biol. 184 703 (Protein Data Bank) entry code 4CHA). In order to determine the appropriate length of spacers to be used for linking the active site residues, we calculated the average (of 15) Cα-to-C$^α$ distances in single peptide bonds and two and three consecutive peptides bonds. These were: one peptide bond (C$^α$-to-C$^α$), 3.80±0.20 Å; two peptide bonds (distance between the first and the third α carbons in C$^α$-C$^α$-C$^α$), 6.20±1.00 Å; three peptide bonds (distance between the first and the fourth α carbons in C$^α$-C$^α$-C$^α$-C$^α$), 7.94±2.07 Å. Therefore, the distances separating the contact residues (FIG. 7A) could be well accommodated by the glycine spacers shown in FIG. 7B. In surface-simulation synthesis, glycine residues have been found (Atassi, M. Z. (1986) in *Protein Engineering, Applications in Science, Medicine and Industry* (Inouye, M. and Sarma, R., Eds.) pp. 125–153, Academic Press, Orlando, Fla.) to be most suited for use as spacers, probably because of their flexibility and the fact that they provide no interfering side chains. The cyclic design, which is crucial for activity, requires closure. The Applicant measured several disulfide bonds in proteins and found that the $C^\alpha$-to-$C^\alpha$ distance in Cys-SS-Cys is 5.5±0.4 Å (range 5.11–5.93 Å). Closure of the peptide (to obtain a cyclic structure) could be achieved anywhere an appropriate space occurs in the structure provided the bond angles in the disulfide bridge do not interfere or induce undue distortion in the orientation of essential active site residues. The best design was that obtained by closure between Cys-58 and Phe-39 (or Tyr in TrPepz) which are separated by 13.16 Å ($C^\alpha$-to-$C^\alpha$). This is satisfied by a Gly-Cys spacer which, with the S—S bond, would give an effective separation of 11.7±1.4 Å. The inner sequence in FIG. 7b was designed to mimic the active site of αCT, while the outer sequence (which differs from the inner sequence by four residues: Phe-39→Tyr,Ile-99→Leu, Ser-189→Asp and Met-192→Gln) mimicked the active site of trypsin. The amino acid sequence of bovine trypsin and the X-ray coordinates for its active site were from references (Mikes, O., Holeysovsky, V., Tomasek, V. and Sorm, F. (1966) *Biochem. Biophys, Res. Commun.* 24, 346–352) and (Marquart, M., Walter, J., Deisenhofer, J., Bode, W. and Huber, R. (1983) *Acta Crystallogr.*, Section B 39, 480 (Protein Data Bank entry 2PTN)), respectively.

Example VI: Functional Behavior of the Synthetic Catalyst

The surface-simulation synthetic peptide, ChPepz, which was designed to mimic the active site of αCT behaved functionally very much like the enzyme itself. The kinetic constants for hydrolysis of BTEE by ChPepz and by αCT were comparable (Table 1). The affinity of ChPepz for the substrate, as evidenced from the $K_m$ value, was very similar to that of the whole enzyme. The $k_{cat}$ values indicated that ChPepz effected hydrolysis at a rate which was in the same order of magnitude as, and only slightly lower than, that of the whole enzyme. Our $k_{cat}$ value (185 sec$^{-1}$) for BTEE hydrolysis by αCT is similar to the value of 193 sec$^{-1}$ reported in the literature (Hartley, B. S., 1964) at pH 7.9 and 25° C. The values of the specificity constant ($k_{cat}/K_m$) of ChPepz and αCT were also comparable indicating that BTEE functioned equally well as a substrate for both ChPepz and αCT. The similarity of the kinetic constants of αCT and ChPepz, and the inhibition of the ChPepz catalytic activity by DIFP (a serine esterase inhibitor) and by TPCK (an αCT inhibitor) suggest that the catalytic process by ChPepz must employ the same mechanism as αCT. The decrease in the rate of catalysis of ChPepz is probably caused by the flexibility of the peptide as it searches, through an equilibrium of conformational states and induced fit, for a catalytically-productive conformation. The virtual loss of catalytic activity when the peptide is rendered acyclic (by reduction of the disulfide bond) is most probably due to the inability of the open-chain structure to achieve such a conformation. This would explain why the first generation of Applicant's synthetic active sites, which employed an open-chain design (Atassi, M. Z. (1985) *Biochem. J.* 226, 477–485) exhibited binding but did not possess measurable catalytic activity. The inability of ChPepz to hydrolyze TAME, which is a trypsin substrate, further confirmed that this peptide had an αCT-like specificity. But the most compelling performance of ChPepz was its ability to hydrolyze proteins producing, from a given protein, peptides that were essentially the same as those produced by αCT.

In addition, test were performed which compared the activity of the two proteases under differing temperature parameters. If temperatures were changed to a lower 10° C. or a higher 48° C., and all other parameters being equal, each of the two synthetic catalysts were compared to their enzyme parent molecule, an interesting pattern is demonstrated as shown below.

| Temp. | % Activity of Native Enzyme at 35° C. | | | |
|---|---|---|---|---|
|  | Chymotrypsin | ChPepz | Trypsin | TrPepz |
| 48 | 0 | 3.5 | 67 | approx. 50 |
| 35 | 100 | 100 | 100 | approx. 40 |
| 10 | 6.8 | 12.6 | 4.5 | 7.4 |

Thus, not only do the synthetic catalysts exhibit activity at temperatures at which the native enzyme fails to do so, but also the synthetic catalysts may actually exhibit improved activity over that seen for the synthetic catalyst at standard temperatures.

Example VII: Surface Simulation of Trypsin Active Site

To further confirm that an enzymically-active peptide design had been achieved, an analog was synthesized in which four residues were substituted to obtain a peptide (TrPepz) that would then mimic the active site of trypsin. Trypsin does not hydrolyze BTEE but hydrolyzes TAME. TrPepz behaved precisely like trypsin, exhibiting an almost identical substrate dissociation constant ($K_m$ and its $k_{cat}$ and $k_{cat}/K_m$ values were about half the corresponding values of the enzyme (Table 1). The values of trypsin $K_m$ (2.56×10$^{-3}$M) and $k_{cat}$ (221 sec$^{-1}$) found here were in agreement with the reported values of 2.76×10$^{-3}$M (Lorand, L. et al., 1961) and 187 sec$^{-1}$ (Martin, C. J., Golubow, J. and Axelrod, A. E. (1959) *J. Biol. Chem.* 234, 1718–1725), respectively, at pH 8.0 and 25° C. The activity of TrPepz was completely inhibited by DIFP, PMSF, soybean trypsin inhibitor and human α-$_1$-antitrypsin, all known to be inhibitors of trypsin. Like ChPepz, the cyclic structure of TrPepz was essential for activity. The most striking finding was the exquisite specificity of TrPepz for cleavage of the C-peptide bonds of arginine and lysine residues in peptides and proteins. Its action on myoglobin or casein resulted in hydrolysis of each protein into peptide fragments that were similar to those obtained by hydrolysis with trypsin itself. In fact, TrPepz was more efficient than trypsin at hydrolyzing Lys-Lys, Lys-Arg, Arg-Lys and Lys-Lys-Lys bonds. Thus, the substitution of four amino acid residues in the ChPepz design caused an unequivocal functional conversion from a chymotryptic to a tryptic activity.

LYSOZYME AND RIBONUCLEASE

General Materials and Methods

Materials. Hen egg lysozyme, *Micrococcus lysodeikticus*, bovine pancreatic ribonuclease A and yeast RNA were obtained from Worthington Biochemical Corp. Imidazole was purchased from Eastman Organic Chemicals. Tryptamine, histamine and dithiothreitol were from Aldrich Chemical Co. Silver nitrate, analytical grade, was from Fisher Scientific and herring testes DNA from Sigma Chemical Co. Reagents for peptide synthesis and $N^\alpha$-Fmoc-amino acids were obtained from Vega Biotechnologies.

Synthesis and Purification. The rationale for the design of the peptides and their structures are given in the examples below. The peptides, LyPepz and RnPepz, were prepared by solid phase synthesis on a benzyloxybenzyl alcohol resin to which 9-fluorenylmethyl-carbonyl (Fmoc)-S-ter-butyl cysteine had been coupled. The methods for synthesis, cyclization and isolation of the monomer have been described above. The oligomeric species was saved for reduction and re-cyclization. The monomeric species was further purified by HPLC on a 5 μm C18 column (10 mm ID×25 cm) using the following gradients: LyPepz, solvent A, 0.1% acetic acid-triethylamine, pH 5.5, and solvent B acetonitrile-0.1% acetic acid (9:1 vol/vol); RnPepz, solvent A, 0.1% trifluoroacetic acid (4:1, vol/vol). The fractions were monitored by absorbance at 256 nm and by their hydrolytic activity toward *M. lysodeikticus* (for LyPepz) or yeast RNA (for RnPepz). The active fraction was freeze-dried and applied on the same column using the same respective solvents but employing gradients that were less steep. The active site fractions (yields: LyPepz, 12.9%; RnPepz 12.2% of the monomer) were homogeneous by high voltage paper electrophoresis and by analytical HPLC, and their amino acid compositions were in excellent agreement with those expected from their covalent structures. Cyclic peptides, which are unrelated to LYZ or RNase and which were used as negative controls in the enzymic assays, were from Applicant's library of synthetic peptides as described above.

Specifically, the following reagents and methods were applied to cyclization, isolation and purification of the LyPepz product:

Cyclization

Peptide (25 mg) was dissolved in 0.5 ml of trifluoroacetic acid (TFA) containing 2-mercaptoethanol (ME) (9:1, vol/vol) and stirred at 4° C. overnight. The peptide was then precipitated with acidified ether [trifluoroacetic acid (TFA) —ether 0.5:95.5, vol/vol], centrifuged and the precipitate washed 3 times with acidified ether. The peptide was dissolved in 0.5 ml of TFA and added drop by drop to 3 liters of 0.6M TEA which was being stirred well by magnetic stirrer. The solution was stirred for 10 days in air (covered with a Kimwipe™ secured around the neck of the bottle by a rubber band), after which it was rotary-evaporated in vacuum (not exceeding 30° C.) down to one ml. (The preparation became oily and showed some precipitation.)

Isolation of the Monomer

The cyclized product was mixed with 2 ml of 0.1M $NH_4HCO_3$, centrifuged and the supernatant was applied onto two columns containing Sephadex G-50 fine (1.6×90 cm each) connected in series and eluted in the ascending direction with 0.1M $NH_4HCO_3$. The second peak (eluting between 320–490 ml) contained the monomeric species while the oligomeric species emerges earlier (eluting between 193–318 ml). The fractions containing the monomer were combined and immediately freeze-dried. The material was dissolved in 2 ml of 0.025M acetic acid and reapplied on two columns (each 1.6×90 cm) of G-50 fine, connected in series and eluted in the ascending direction with 0.025M acetic acid. The fraction eluting between 400–490 ml contained hydrolytic activity towards *Micrococcus lysodeikticus*.

Reverse-Phase HPLC

The monomeric fraction obtained above was further purified by reverse-phase HPLC as follows:
Column: Reverse-phase C-18, semi-preparative 10 mm×25 mm (Rainin)
(1) Chromatography No. 1
  Solvent A: 0.1% acetic acid, adjusted to pH 5.5 with TEA
  Solvent B: Acetonitrile—solvent A (9:1), vol/vol)
  Flow Rate: 1.5 ml/min
  Elution gradient:
  0–20% B, 3 min.
  20–40% B, 40 min.
  40–60% B, 10 min.

The material was resolved into 2–6 peaks. Peak No. 8 was found to possess the most activity. Peak 8 was reapplied on the same column.
(2) Chromatography No. 2
  Solvent A: 0.1% acetic acid, adjusted to pH 5.5 with TEA
  Solvent B: Acetonitrile—Solvent A (9:1, vol/vol)
  Elution gradient:
  0–20% B, 3 min.
  20–40% B, 40 min.
  40–60% B, 5 min.

Catalytic activity was found in peak #2. Peak 2 corresponded to 45% of the total material of peak 8. Peak 2 was pure and no further purification was needed.

Specifically, the following reagents and methods were applied to cyclization, isolation and purification of the RnPepz product:

Reduction of RnPepz crude product was done in mercaptoethanol-8M urea (1:9, vol/vol) as described for ChPepz and TrPepz. The desalting of the reduced product was done on Sephadex G-15, as described for ChPepz.

Isolation of the Monomer

The RnPepz was isolated by size exclusion chromatography.
Column: Protein Pack 60, 7.8 mm×300 mm (Waters)
Solvent: 0.05M $NH_4HCO_3$
Flow Rate: 0.7 ml/min Six peaks were obtained. Peaks 1 and 2 contained oligomers. Peak 3 contained the active fraction (as monitored by hydrolysis of yeast RNA) and corresponded to the monomer.

Reverse-Phase HPLC

The monomeric fraction (peak 3 from Protein Pack 60) obtained above was further purified by reverse-phase HPLC as follows:
Column: Reverse-phase C-18, semi-preparative 10 mm×25 mm (Rainin)
(1) Chromatography No. 1
  Solvent A: 0.05M acetic acid
  Solvent B: solvent A+acetonitrile (1:4), vol/vol)
  Elution gradient:
  0–40% B, 10 min.
  40–85% B, 30 min.

Eleven peaks were obtained. The major one (peak 10) contained the catalytic activity.
(2) Chromatography No. 2

Peak 10 from chromatography no. 1 was reapplied on the same column
  Solvent A: 0.1% TFA in water
  Solvent B: Solvent A+acetonitrile (1:4, vol/vol)
  Elution gradient:
  0–2% B, 1 min.
  20–50% B, 10 min.
  50–60% B, 25 min.
  60–80% B, 5 min.

Nine peaks were obtained. Peaks 7, 8 and 9 were not well resolved. They were combined and reapplied on the same column.
(3) Chromatography No. 3

Peaks 7–9 from chromatography no. 2 were reapplied on the same column
  Solvent A: 0.1% TFA in water
  Solvent B: Solvent A+acetonitrile (1:4, vol/vol)
  Flow Rate: 1.5 ml/min
  Elution gradient:
  0–25% B, 1 min.
  25–36% B, 30 min.
  36–80% B, 10 min.

The material was resolved into 19 peaks. The highest catalytic activity coincided with peak 17.

(4) Chromatography No. 4

Same conditions as in chromatography no. 2 were repeated. Peak No. 10 was most active. No further purification of peak 10 was needed.

Measurement of Catalytic Activity

Measurement of Lysozyme Activity. The kinetics of the catalytic activity of LYZ and LyPepz were determined by hydrolysis of *M. lysodeikticus* as described (Neville, W. M. and Eyring, H. (1972) *Proc. Natl. Acad. Sci. USA* 88, 3613–3617). Assays were done at 25° C. in 0.125M NaCl using 1.5 µg ($1.04 \times 10^{-4}$ µmole) of LYZ and 4.25 µg ($1.13 \times 10^{-3}$ µmole) of LyPepz and different amounts of cell suspension (in the range 330 to 100 µg/ml) in a total reaction volume of 1.10 ml. The decrease in turbidity was measured at 450 nm on a recording spectrophotometer. Reaction mixtures that contained no catalyst or had RnPepz or other cyclic peptides that are unrelated to LYZ (instead of LyPepz) were used as controls. Kinetic constants were determined from the linear plots of 1/initial velocity (in change of absorbance/min) against 1/substrate concentration in mg/ml as described (Lineweaver, H. and Burk, D. (1934) *J. Amer. Chem. Soc.* 56, 658–666). To study the effect of reduction of the disulfide bond on the catalytic activity, LyPepz (5.6 µg=$1.51 \times 10^{-3}$ µmole) or LYZ (1.5 µg=$1.04 \times 10^{-4}$ µmole) were mixed with 10 molar excess of dithiothreitol. After reaction at room temperature for 3 hr, the reduced cyclic synthetic peptide catalyst or LYZ were each added to 140 µg of *M. lysodeikticus* (total reaction volume, 1 ml of 0.125M NaCl) and the activity was measured by the decrease of absorbance at 450 nm as described above. The effects of the lysozyme inhibitors, imidazole, tryptamine and histamine were also determined by pre-mixing the synthetic catalyst or LYZ for 3 hr at room temperature with a 10 molar excess of each inhibitor before addition to the cells, using the same amounts of catalysts and cells, as described for the effect of dithiothreitol.

Specifically, the following reagents and methods were used ot assay lysozyme activity:

Reagents:

a. 0.125M NaCl b. LyPepz solution—prepared in solvent (a), containing 1–40 µg/200 µl c. Negative controls—peptides unrelated to LyPepz in solvent (a) from 1–40 µg/200 µl d. *Micrococcus lysodeikticus* solution in solvent (a)—from 100 µg to 300 µg/800 µl.

e. Positive control—hen lysozyme in solvent (a) at 1, 2, and 3 µg/200 µl.

Applicant always dedicated a separate spectrophotometer cuvette for this positive control. To perform the assay, 200 µl of the LyPepz negative control or positive control solution was added to 800 µl of the substrate solution. The decrease in turbidity was monitored at room temperature at 450 nm. The decrease obtained with the LyPepz sample had to be corrected for the non-specific decrease obtained with the same concentration of the negative control peptide acting on the same amount of substrate. Precautions as to assaying and stability were the same as described for ChPepz and TrPepz. Measurement of Ribonuclease Activity. The catalytic activity of RNase and RnPepz were determined by their hydrolytic effects on yeast RNA (Kunitz, M. (1946) *J. Biol. Chem.* 164, 563–569; Gutte, B. and Merrifield, R. B. (1971) *J. Biol. Chem.* 246, 1922–1941). RNase (1.5 µg=$1.095 \times 10^{-4}$ µmole) and RnPepz (2.9 µg=$1.21 \times 10^{-3}$ µmole) were each mixed with different amounts of yeast RNA (from 500 to 180 µg/ml) in a total reaction volume of 1 ml of 0.1M sodium acetate at pH 5. The decrease in absorbance at 300 nm with time was measured on the recording spectrophotometer. Reaction mixtures that contained no catalyst as well as mixtures containing LyPepz or other cyclic peptides unrelated to RNase were used as controls. The kinetic parameters of the hydrolytic activities were determined by Lineweaver-Burk plots (Lineweaver, H. and Burk, D. (1934) *J. Amer. Chem. Soc.* 56, 658–666) of 1/absorbance change per minute against 1/substrate concentration in mg per ml.

Specifically, the following reagents and methods were used to measure RnPepz activity:

Reagents a. 0.1M sodium acetate buffer, pH 5.0 b. Substrate (yeast RNA)—several dilutions in the range 200 µg–600 µg/ml of buffer (a)

c. RnPepz—several dilutions from 1 µg to 40 µg/100 µl of buffer (a).

d. Ribonuclease A (positive control)—several dilutions from 1 µg to 4 µg per 100 µl of buffer (a)

e. Peptides unrelated to RnPepz (negative controls)—several dilutions from 1 to 40 µg/100 µl of buffer (a).

To perform the assay, 1 ml of a given substrate solution was mixed with 100 µl of RnPepz, or unrelated peptide solution. The activity (hydrolysis of the RNA) was monitored by change (decrease) in absorbance at 300 nm. The change in absorbance with the test samples (RnPepz) was correlated for the small change obtained with the same amount of unrelated peptides (negative controls) acting on the corresponding concentration of substrate. Precautions as to assaying and stability were the same as described for ChPepz and TrPepz.

The effects of disulfide-bond reduction on RNase and RnPepz activities were determined by premixing each catalyst (RNase, $1.095 \times 10^{-4}$ µmole; RnPepz, $2.42 \times 10^{-3}$ µmole) with 10 molar excess of DTT for 3 hr at room temperature, followed by addition to 600 µg of yeast RNA (total reaction volume, 1 ml. of 0.1M sodium acetate pH 5.0). The reactions were monitored by the decrease in absorbance at 300 nm as above. The effects of inhibitors (denatured DNA or $Ag^+$) on activities were also done by pre-mixing RNase or RnPepz with denatured DNA (250 µg) or with 10 molar excess of $AgNO_3$ prior to addition to RNA, using the same amounts of catalyst and substrate described for DTT. Denaturation of DNA was done by boiling a solution in water (1 mg/ml) for 10 min, then chilling immediately in ice.

Lysozyme and Ribonuclease Examples

Example VIII: Hydrolysis of *M. lysodeikticus* by LYZ and LyPepz

Figure 8:
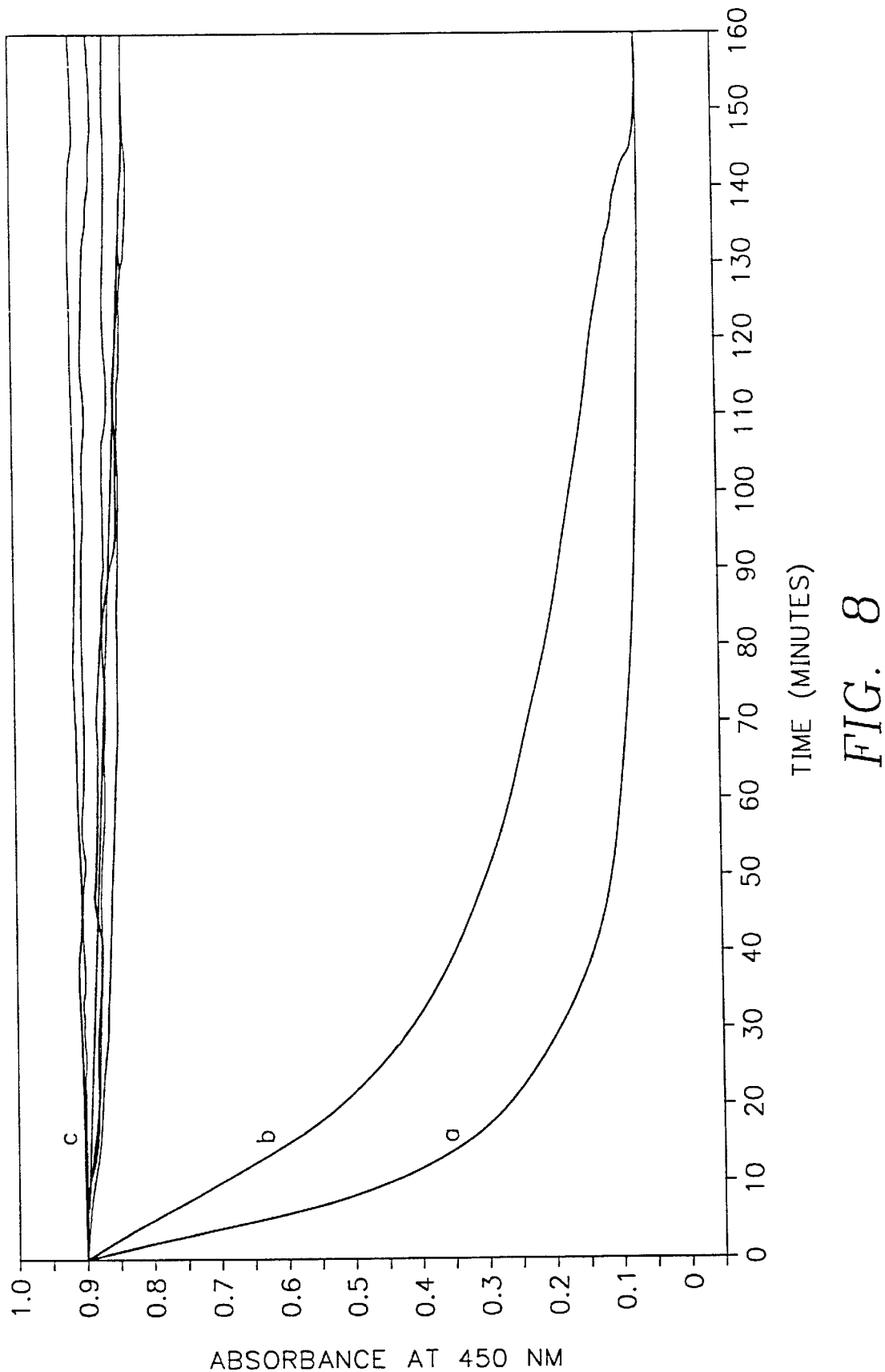
FIG. 8. Time-course hydrolysis of M. lysodeikticus by LYZ and LyPepz. Hydrolyses were carried out, as described in the text, on 140 μg of substrate and monitored on a recording spectrophotometer by decrease in absorbance at 450 nm using (a) 1.5 μg ($1.04 \times 10^{-4}$ μmole) of LYZ and (b) 5.6 μg ($1.51 \times 10^{-3}$ μmole) of LyPepz. Curves (c) represent the following reactions all of which had near zero hydrolytic activity: LyPepz (5.6 μg) inhibited by 10 molar excess of imidazole, histamine or tryptamine; LyPepz after reduction of the intramolecular disulfide bond; and action of unrelated peptide controls (RnPepz and other cyclic peptides).
Figure 9:
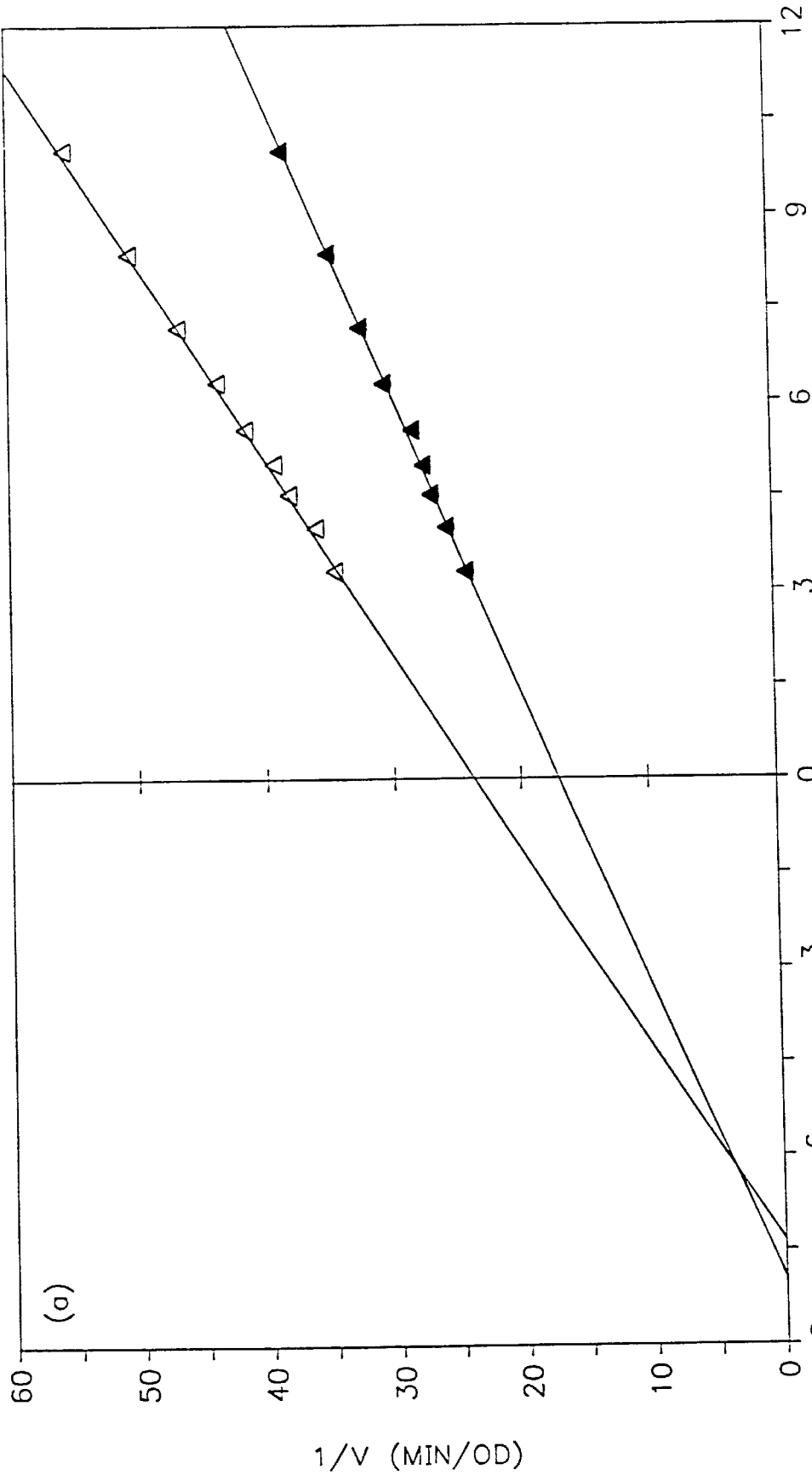
FIG. 9. Lineweaver-Burk plots for M. lysodeikticus hydrolysis by LyPepz (Δ), and LYZ (▲). Assays were carried out at 25° C. in 0.125M NaCl using nine different substrate concentrations in 3–6 replicates as described in the text. The $K_m$ and $k_{cat}$ values obtained from these plots are given in Table 2.
Figure 10:
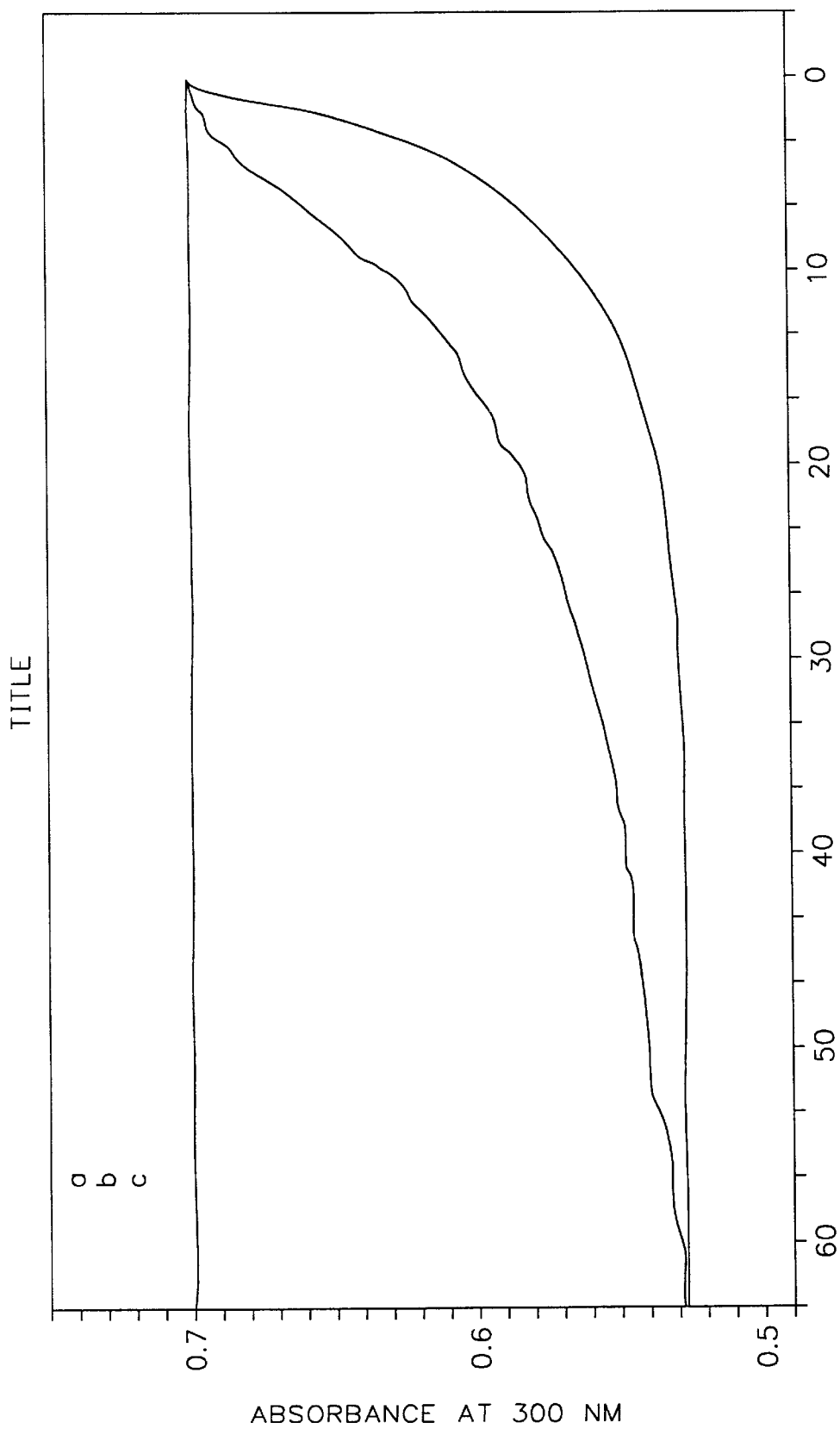
FIG. 10. Time-course hydrolysis of yeast RNA by RNase and RnPepz. Reactions were done at 25° C. on 700 μg of yeast RNA. The decrease in absorbance at 300 nm was monitored continuously on a recording spectrophotometer. The curves show: (a) hydrolysis by 1.5 μg ($1.095 \times 10^{-4}$ μmole) of RNase; (b) hydrolysis by 5.8 μg ($2.42 \times 10^{-3}$ μmole) of RnPepz; (c) RnPepz inhibited by 250 μg of denatured DNA, or 10 molar excess of $AgNO_3$; and RnPepz rendered acyclic by reduction of the disulfide bond. Also superimposed on curve (c) is the action of unrelated peptide controls (LyPepz and other cyclic peptides) on yeast RNA.

In its action on *M. lysodeikticus*, LyPepz exhibited a lysozyme-like activity, causing complete hydrolysis of the cell wall of the organism (FIG. 8). The activity was specific since RnPepz had no hydrolytic activity on the cell wall. The kinetic constants were determined from experiments at different substrate concentrations (FIG. 9). Because it is not possible to express substrate concentrations in molar quantities, the constants were based on mg/ml and initial velocities in OD change/min. These results showed that the $K_m$ values of LyPepz and LYZ were quite comparable. The turn-over rate of LYZ, however, was about 7 times higher than that of LyPepz. The synthetic catalyst, like LYZ, was completely inhibited by imidazole, tryptamine or histamine (FIG. 8). The hydrolytic activity of LyPepz was completely lost by reduction of the disulfide bond with DTT (FIG. 8). It should be noted that RnPepz and other control peptides had no hydrolytic activity on *M. lysodeikticus*. Both LyPepz and LYZ showed an optimum temperature for activity between 30° C.–35° C. and there was no significant change in their activities to one another in the range 10° C.–45° C.

Example IX: Hydrolysis of yeast RNA by RNase and RnPepz

Like Rnase, RnPepz was able to hydrolyze yeast RNA completely (FIG. 9), while LyPepz (used as a control) had no effect on this substrate. Because it is difficult to express substrate concentrations in molar quantities, the kinetic constants were calculated using substrate concentration values in mg/ml. Also, velocities of hydrolysis were measured in decrease in OD/min. Lineweaver-Burk plots of the hydrolytic reactions (FIG. 4) showed that the $K_m$ value for RnPepz was almost identical to that of RNase. RnPepz, however, exhibited a $k_{cat}$ value which was considerably lower than that of the whole enzyme. The activity of RnPepz was completely destroyed by reduction of the disulfide bond. The temperature optimum for the hydrolytic activity of RnPepz was around 25° C., while the optimum for the enzyme was closer to 35° C. In the range 17.5° C.–45° C., RnPepz and RNase showed little change in their relative activities. At 10° C. neither RnPepz nor RNase had any measurable hydrolytic activity on yeast RNA. Like RNase, RnPepz was completely inhibited by $Ag^+$ or denatured DNA. It should be noted that LyPepz, lysozyme and other synthetic cyclic peptides that are unrelated to RNase had no effect on yeast RNA.

Design of the Synthetic Peptide Catalysts Based on Ribonuclease and Lysozyme

Lysozyme (muramidase) catalyzes cleavage of the N-acetylmuramic acid-N-acetylglucosamine β-1,4-linkages that occur in the cell-wall polysaccharide of some organisms (e.g. *M. lysodeikticus*). The LYZ amino acid sequence (Canfield, R. E. (1963) *J. Biol. Chem.* 238, 2869; Jollés, J., Jauregui-Adell, J., Bernier, I. and Jollé, P. (1963) *Biochim. Biophys. Acta* 78, 668–698) and three-dimensional structure (Blake, C. C. F., Mair, G. A., North, A. C. T., Phillips, D. C. & Sharma, V. R. (1967) *Proc. Roy. Soc.* B167, 365; as well as its interactions with substrate analogs and inhibitors (Blake, C. C. F., Mair, G. A., North, A. C. T., Phillips, D. C. and Sarma, V. R. (1967) *Proc. Roy. Soc.* B167, 365–377; Imoto, T., Johnson, L. N., North, A. C. T., Phillips, D. C. and Rupley, J. A. (1972) in *The Enzymes* (Boyer, P. D., ed) Vol. 7, pp. 665–868) have been determined. For the present work, the X-ray coordinates were from Diamond, R. and Phillips, D. (1975) Protein Data Bank, Entry Identification Code 6LYZ; Kelly, J. and James, M. (1979) Protein Data Bank, Entry Identification Code 9LYZ. Ribonuclease A effects hydrolysis of the phosphodiester bond between the 5'-ribose of a nucleotide linked to the 3'ribose of a pyrimidine nucleotide. Its amino acid sequence (Smyth, D. G., Stein, W. H. and Moore, S. (1963) *J. Biol. Chem.* 238, 227–234.) and three-dimensional structure (Kartha, G., Bello, J. and Harker, D. (1967) *Nature* (London) 213, 862) are known. The RNase X-ray coordinates employed in the present studies were from Nachman, J. and Wlodawer, A. (1989) *Protein Data Bank*, Entry codes 8RSA and 9RSA.

Example X: Lysozyme

Figure 11:
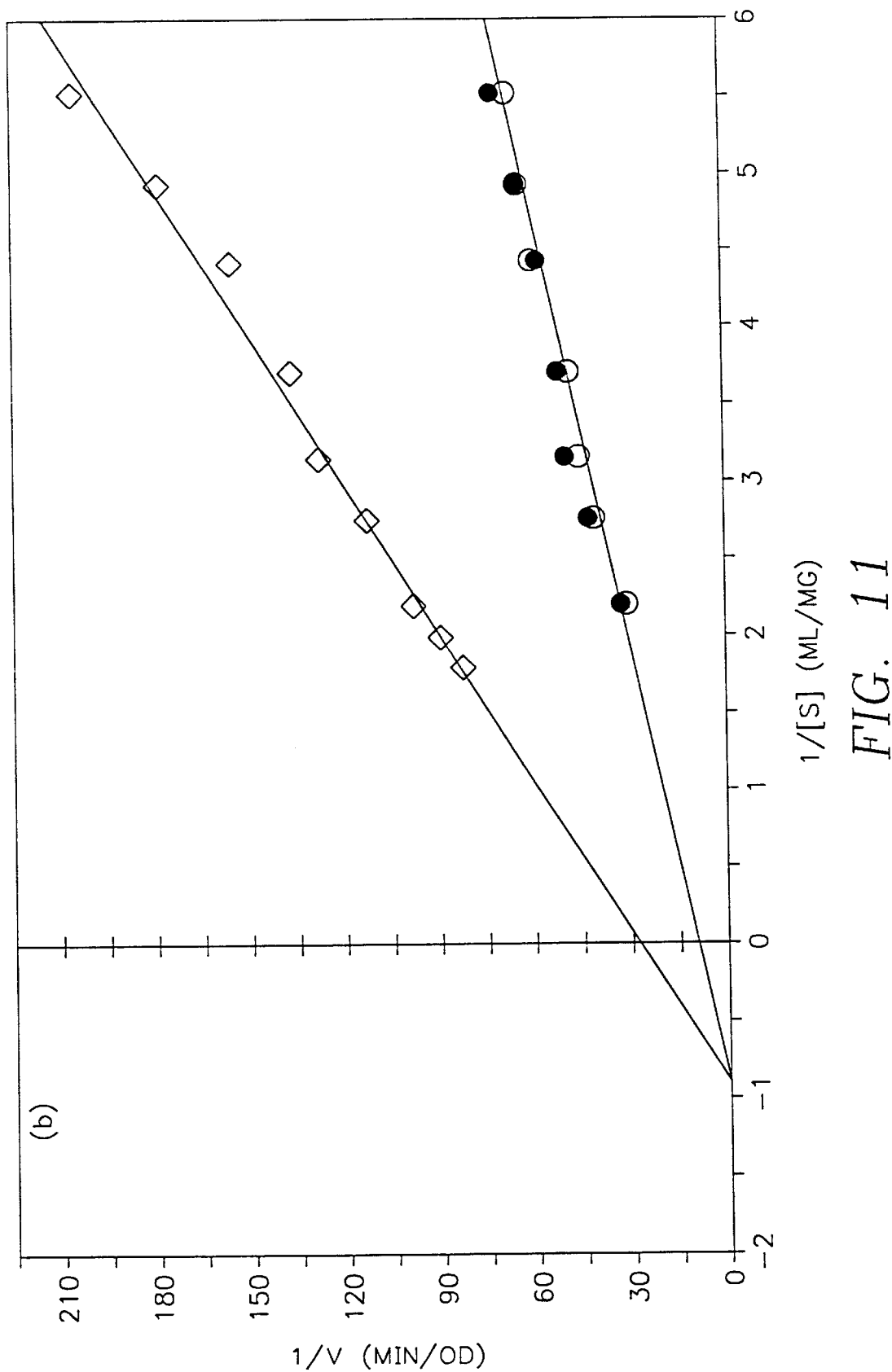
FIG. 11. Lineweaver-Burk plots for yeast RNA hydrolysis by RnPepz (◇), and RNase (●,603 ). Assays were carried out in 0.1M sodium acetate at pH 5.0 and 25° C. in 3–6 replicate analyses of different substrate concentrations, as described in the text. The kinetic constants derived from these plots are given in Table 2.
Figure 12:
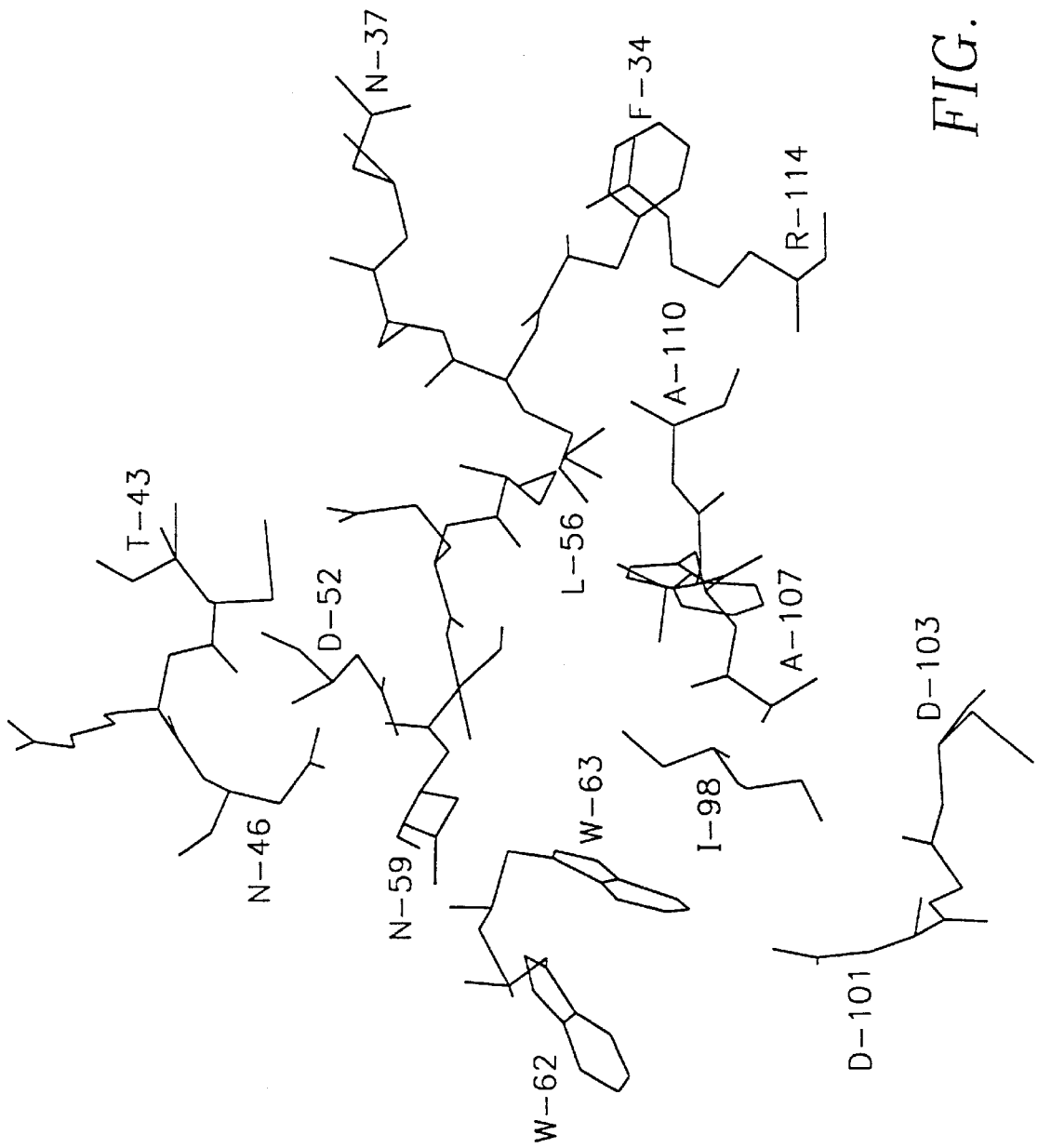
FIG. 12. A diagram of the spatial disposition of the active site residues of LYZ.
Figure 13A:
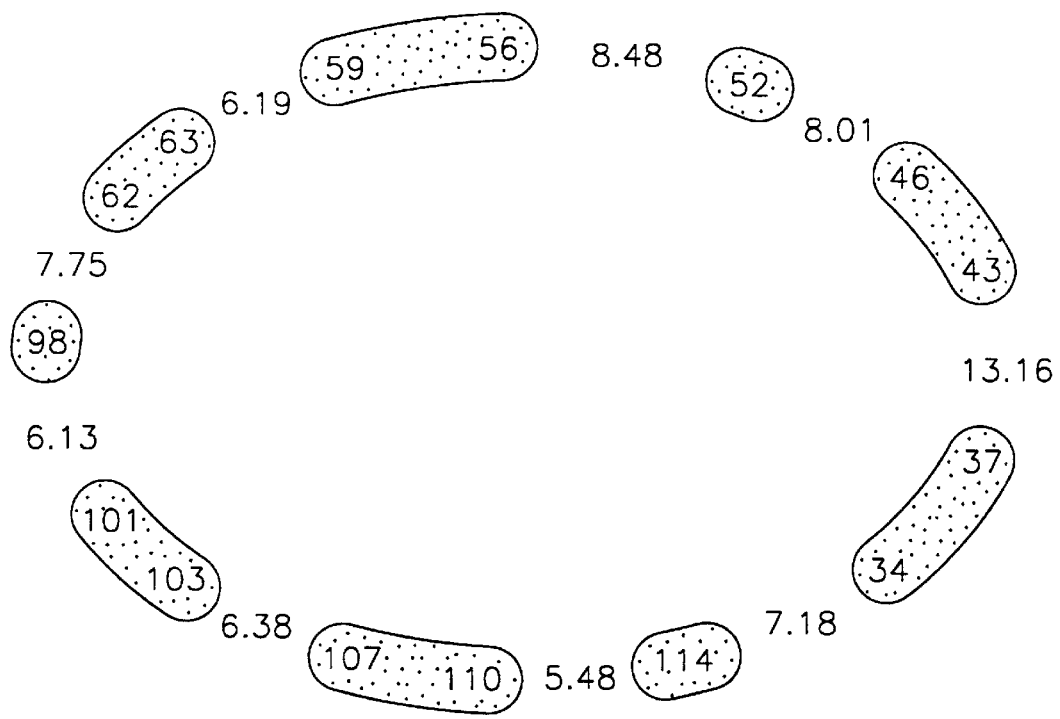
FIG. 13. Design of the surface-simulation peptide mimicking the active site of LYZ. (a) Shows the active site residues in the shaded areas and the $C^\alpha$-to-$C^\alpha$ distances (in Å) separating the appropriate residues. (b) Gives the surface-simulation synthetic peptide designed to mimic the active site of LYZ. The shaded areas, representing the actual active site residues of LYZ, were linked by glycine spacers which were introduced to achieve appropriate spacing between the regions and the residues of the active site. (Cter) denotes the C-terminal Cys and (Nter) is the N-terminal Cys of the peptide. A disulfide bridge between these half cystine residues is used to cyclize the peptide.
Figure 13B:
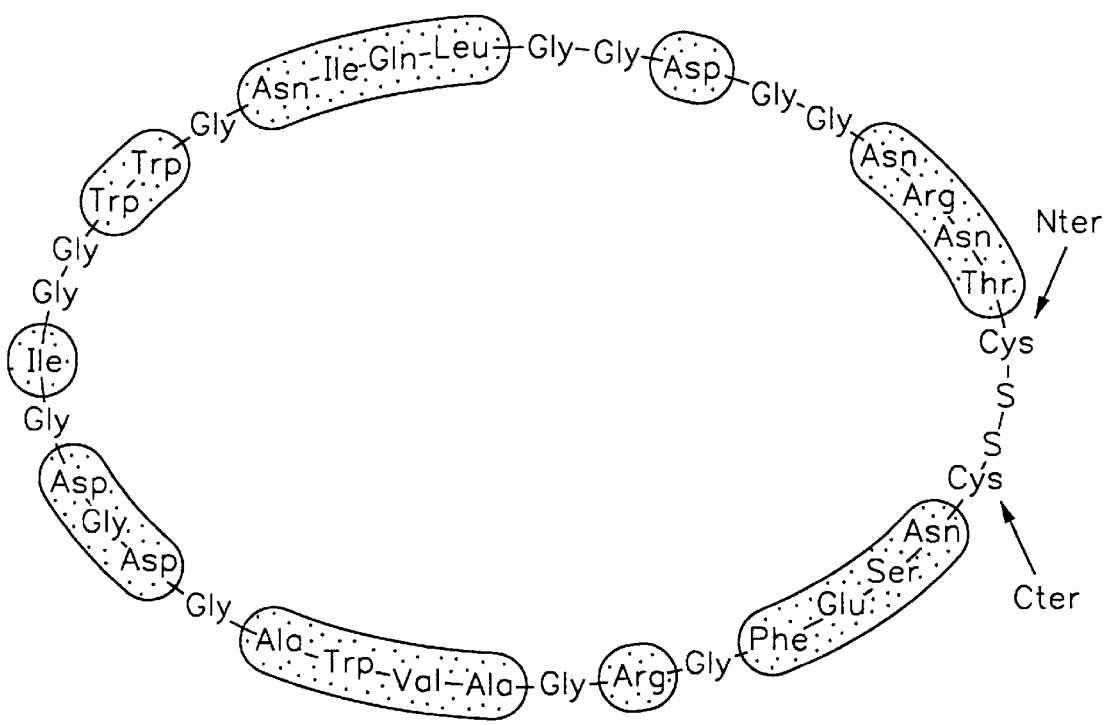
Figure 14:
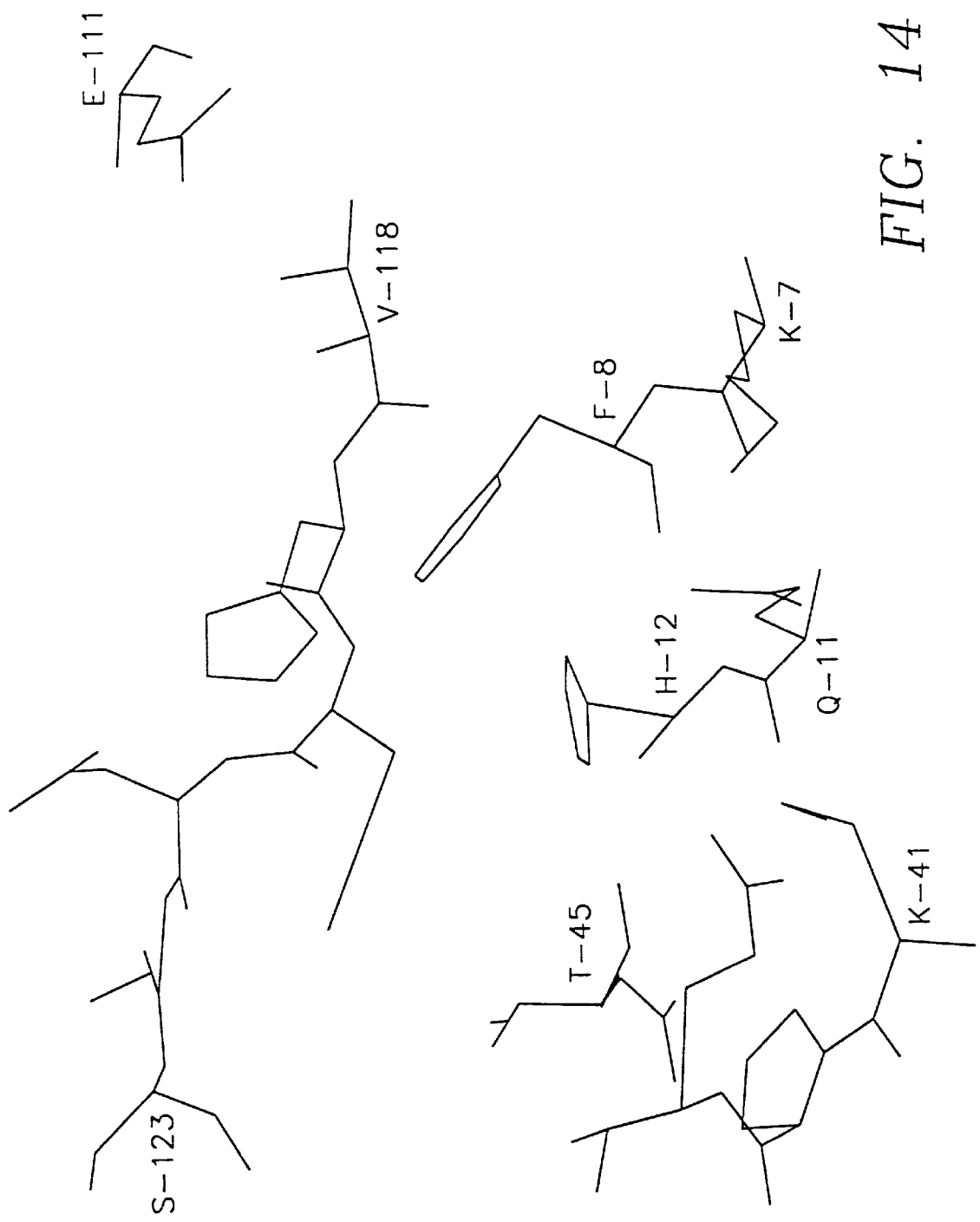
FIG. 14. A diagram of the spatial disposition of the essential residues of the active site of RNase.
Figure 15A:
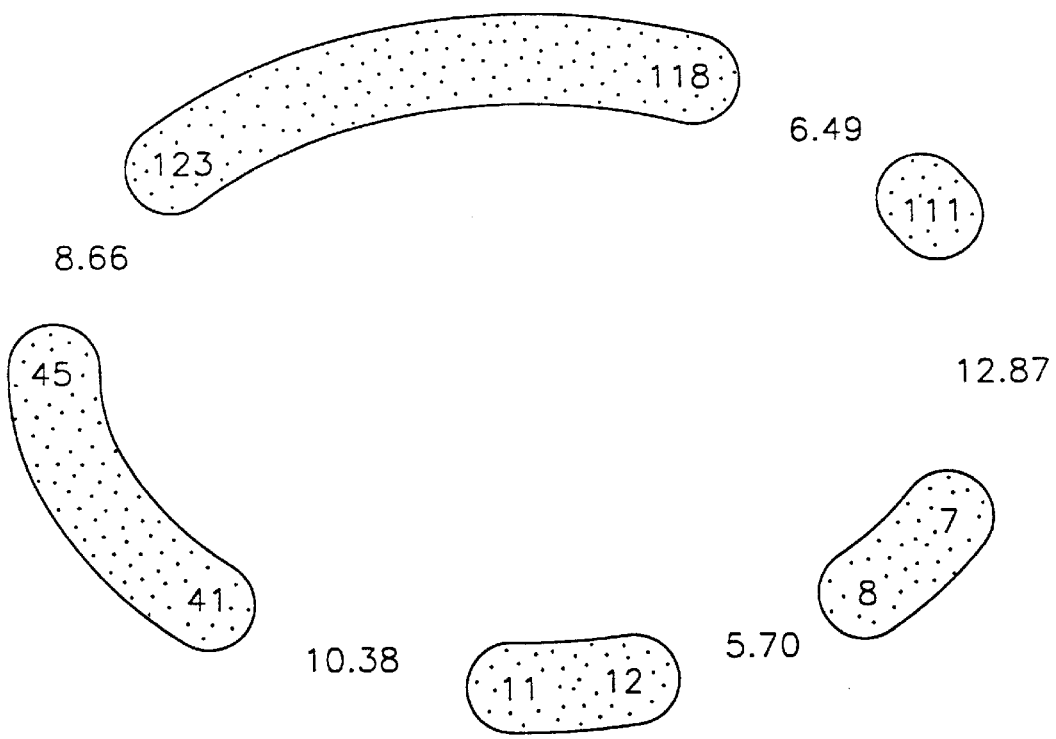
FIG. 15. Design of the surface-simulation peptide mimicking the active site of RNase. (a) The active site residues shown in the shaded areas and the $C^\alpha$-to-$C^\alpha$ distances separating them are given in Å. (b) Structure of the surface-simulation synthetic peptide designed to mimic the active site of RNase. The shaded areas are the actual site residues and the glycine residues in between are spacers. A disulfide bridge between the Cys residues at the C-terminal (Cter) and the N-terminal (Nter) is used to cyclize the peptide.
Figure 15B:
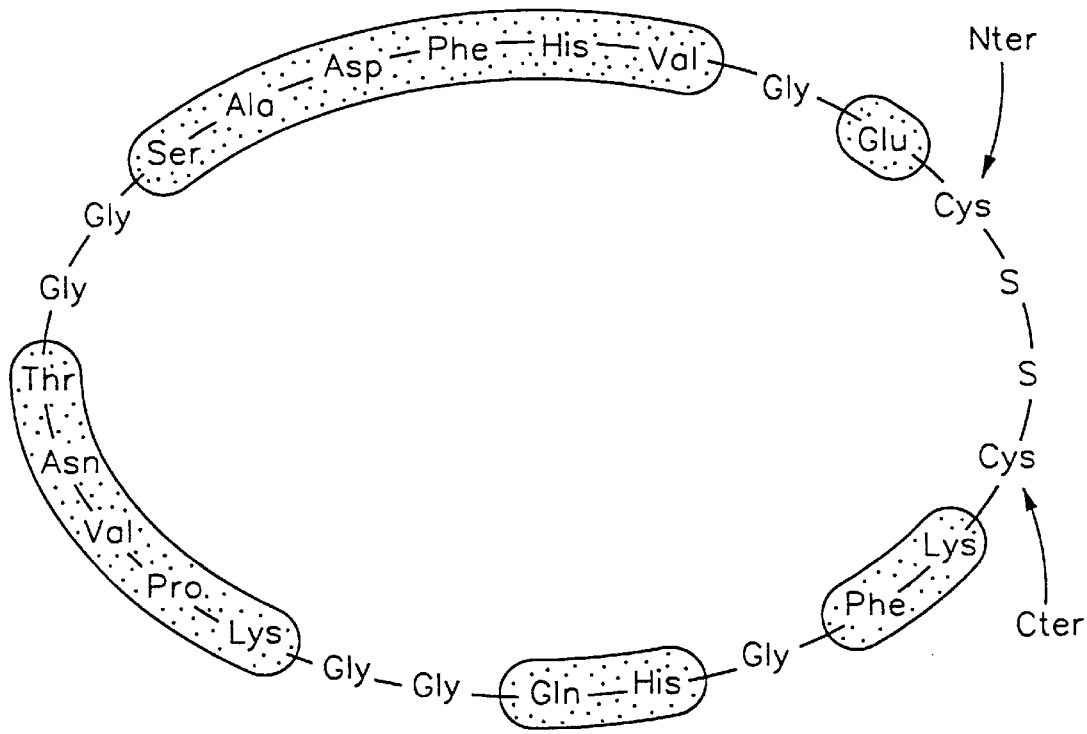
Figure 20A:
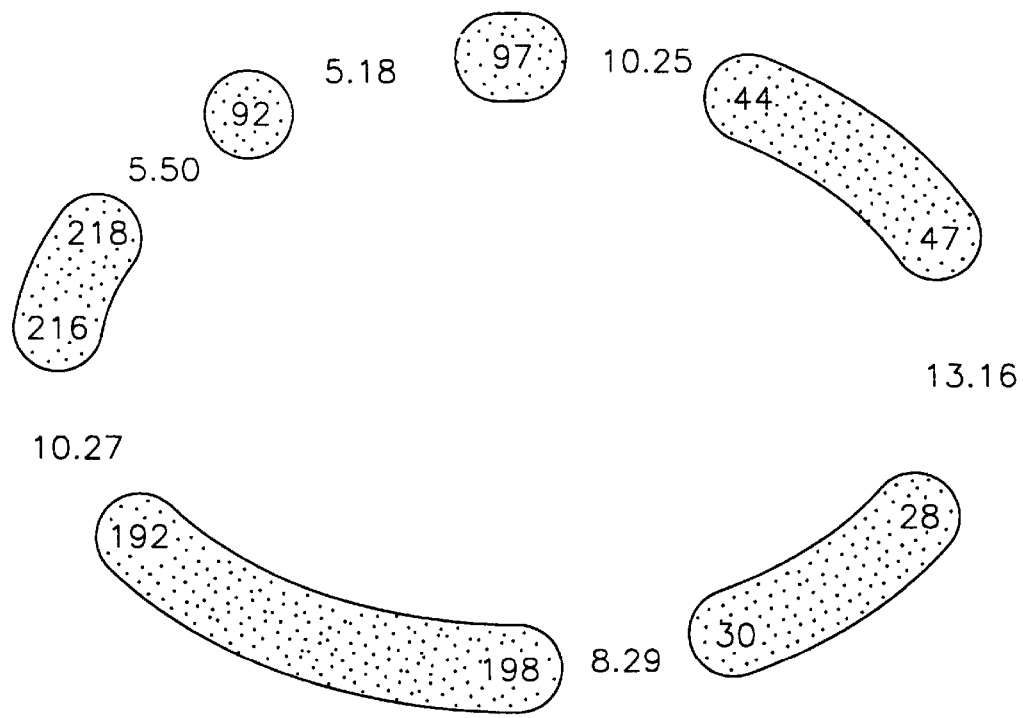
FIG. 20. Design of the surface-simulation peptides mimicking the active sites of urokinase (UkPepz) and tissue plasminogen activator (TpPepz). (a) Shown are the contact residues of the active site in the shaded areas and the distances (C$\alpha$-to-C$\alpha$, in Å) separating the appropriate residues. Residue numbers are based on urokinase sequence. (b) indicates the surface-simulation synthetic peptides designed to mimic the active sites. The residues in the shaded areas are the actual active site residues of urokinase while those linking these shaded areas are glycine spacers introduced to achieve appropriate distances of separation between the respective residues and regions of the site. (Cter) is the C-terminal Cys and (Nter) denotes the N-terminal Cys of the peptides which are cyclized by the disulfide between the two Cys residues. The outer sequence which shows the substitutions made to construct TpPepz differs from UkPepz in 8 positions: Glu-27, Arg-28, Phe-29, Leu-30, Ala-45, Tyr-92, Ala-193, Ile-216.
Figure 20B:
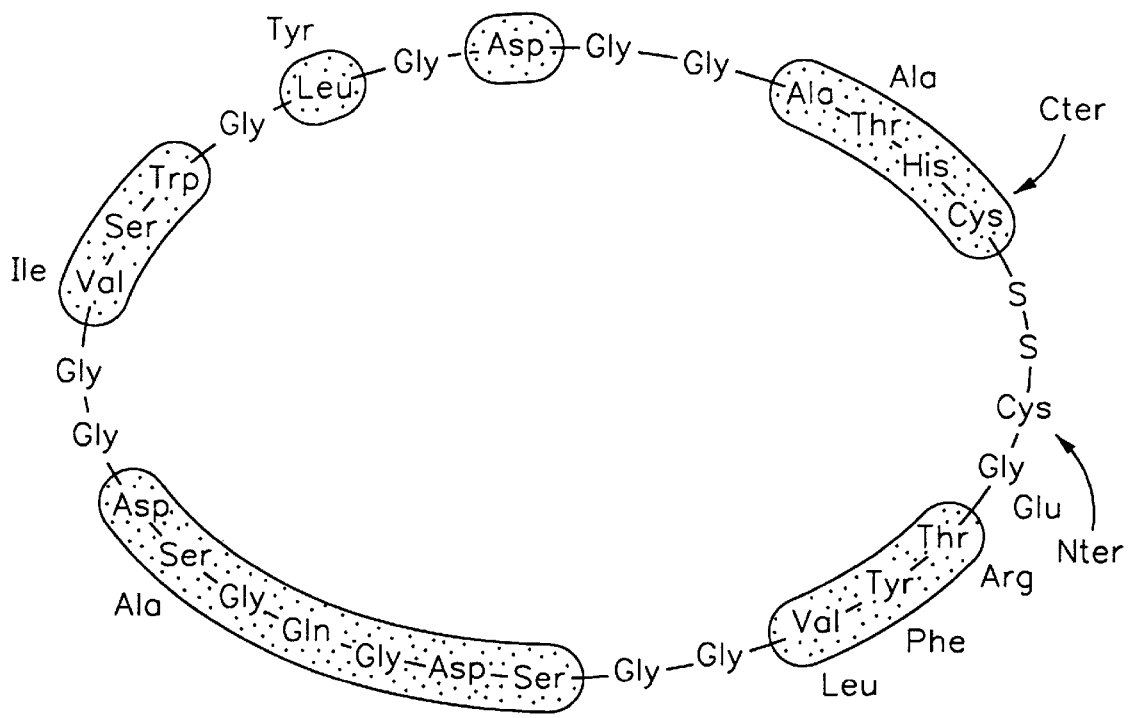

The essential residues of the active site of LYZ are shown in FIG. 12. The elements of the design of LyPepz are outlined in FIG. 13, which shows (in FIG. 13a) the sequence positions of the LYZ active site residues together with the $C^\alpha$-to-$C^\alpha$ distances (in Å separating them and (in FIG. 11b) the structure of the peptide designed to mimic the active site. FIG. 14 shows the essential residues of the active site of RNase. The distances separating these residues and the structure of the peptide designed to mimic the active site of RNase are given in FIG. 15. The appropriate numbers of glycine spacers used in the design of each synthetic catalyst were based on the calculation that the average $C^\alpha$-to-$C^\alpha$ distances were: one peptide bond ($C^\alpha$-to-$C^\alpha$), 3.80±0.20 Å; two peptide bonds (distances between $C^\alpha_1$ and $C^\alpha$ in $C^\alpha_1$-$C^\alpha_2$-$C^\alpha_3$), 6.20±1.00 Å; three peptide bonds (distance between $C^\alpha_1$ and $C^\alpha_4$ in $C^\alpha_1$-$C^\alpha_2$-$C^\alpha_3$-$C^\alpha_4$), 7.94±2.07 Å. Glycine residues were found (Atassi, M. A. (1986) in *Protein Engineering Applications in Science, Medicine and Industry*, eds. Inouye, M. and Sarma, R. (Academic Press, Orlando, Fla.), pp. 125–153) to be most suitable for use as spacers in surface-simulation synthesis, probably because they are flexible and do not have a side chain that might potentially interfere in the activity of the peptide. To prepare the cyclic structure which is essential for activity, the peptides were cyclized by an intramolecular disulfide bond. The latter was placed in each synthetic catalyst in a position that would closely maintain the appropriate spacing and cause no interference or undue distortion in the orientation of the essential site residues. The $C^\alpha$-to-$C^\alpha$ distance in Cys-SS-Cys was found (Atassi, M. Z. et al. (1993), id) to be 5.52±0.41 Å. The best design, which fulfilled these requirements was obtained by a disulfide bridge between Asn-37 and Thr-43 in LyPepz and between Lys-7 and Glu-11 in RnPepz (see FIGS. 12 and 15).

The peptide LyPepz possessed a catalytic activity which was similar to that of the protein itself. The affinity of LyPepz for the substrate was quite similar to that of LYZ as evidenced by their comparable $K_m$ values. The $K_m$ value obtained here for LYZ (121 mg/liter) in 0.125M NaCl is similar to the value of 129 mg/liter reported (Neville, W. M. et al. (1972), id) in the same solvent. The $k_{cat}$ values showed that LyPepz hydrolyzed the cell wall of *M. lysodeikticus* in a time-frame that was very much enzyme-like. The finding that LyPepz was almost completely inhibited by imidazole, histamine or tryptamine, which are known to inhibit LYZ by forming charge-transfer complexes with the tryptophan residues in the enzyme (Shinitzky, M., Katchalski, E., Grisaro, V. and Sharon, N. (1966) *Arch. Biochem. Biophys.* 116, 332–343; Swan, I. D. A. (1972) *J. Mol. Biol.* 65, 59–62), would indicate that LyPepz employs the same mechanism of catalysis as that used by LYZ. The inability of RnPepz and other control peptides to hydrolyze *M. lysodeikticus* cell wall demonstrated that the action of LyPepz on the cell wall is a true muramidase activity.

Example XI: Ribonuclease

In their hydrolysis of yeast RNA, RnPepz and RNase, exhibited near-identical $K_m$ values (Table 2), indicating that the two catalysts possessed comparable affinities for the substrate. The $K_m$ value found here for RNase (1.25 mg/ml) in 0.1M sodium acetate buffer, pH 5.0, is in agreement with the reported values of 1.20 mg/ml (Gutte, B. et al. (1971), id) and 1.25 mg/ml (Edelhock, H. and Coleman, J. (1956) *J. Biol. Chem.* 219, 351–363). The $k_{cat}$ values of RnPepz and RNase showed that the synthetic catalyst effected hydrolysis at a rate which was considerably lower than that of the enzyme. Nevertheless, RnPepz was quite efficient and was in fact able to effect complete hydrolysis of RNA in an enzyme-like time frame. The specificity of the hydrolytic action of RnPepz on RNA was evident from its inability to hydrolyze the cell wall of *M. lysodeikticus* and conversely from the lack of action of LyPepz and other control peptides on RNA. The complete inhibition of RnPepz by heavy metals and by DNA, which are known to inhibit RNase (Sekine, H., Nakano, E. and Sakaguchi, K. (1969) *Biochim. Biophys. Acta* 174, 202–210), would suggest that the synthetic catalyst employs a similar catalytic mechanism to that of the enzyme.

Example XII: Design Problem Areas

The lower rate of catalysis by the synthetic catalysts, relative to their respective enzymes, is most likely caused by the existence of each peptide in an equilibrium of conformational states influenced by substrate-induced fit. The peptide will display activity when a catalytically-productive conformation is achieved. The finding that integrity of the cyclic structure was crucial for the activity of both LyPepz and RnPepz (as evidenced from the total loss of activity on reduction of the disulfide bond) is probably due to the inability of the acyclic form to assume such a conformation. This is similar to the findings with the two proteolytic synthetic catalysts which mimicked the activities of trypsin and α-chymotrypsin (Atassi, et al. (1993), id). The presence in RnPepz of two segments (residues 7–8 and 41–45), possessing the retro-sequence to their counterparts in native RNase may have also contributed to the decrease in the rate of hydrolysis by RNPepz. A synthetic analog in which these two segments were made by D-amino acids did not show any significant changes in the rate of hydrolysis (data not shown).

TABLE 2

Kinetic constants for hydrolysis of *M. lysodeikticus* by LYZ and LyPepz and of yeast RNA by RNase and RnPepz

|  | $K_m$ (mg/liter) | $k_{cat}$ (OD units/μmole/sec) |
| --- | --- | --- |
| Hydrolysis of *M. lysodeikticus* by: |  |  |
| LyPepz | 133.4 ± 2.6 | 1.38 ± 0.01 |
| LYZ | 120.6 ± 4.0 | 9.26 ± 0.12 |
| Hydrolysis of yeast RNA by: |  |  |
| RnPepz | 1238 ± 228 | 0.559 ± 0.01 |
| RNase | 1254 ± 460 | 14.05 ± 6.85 |

Example XIII: Homologous Peptide-Sequences to Active Synthetic Catalysts

Having successfully utilized the methods of the invention to generate synthetic, catalytically active peptides modeled on enzymes with known 3-dimensional structures, Applicant began the process of identifying other such peptides by homology as described in the specification. In the first such instance, as already described, Applicant successfully predicted by homology that an active tryptic peptide could be constructed where sequence homology of chymotrypsin to trypsin allowed substitution of trypsin-derived residues for those in the chymotrypsin modeled synthetic catalyst. Employing the same rationale, Applicant has designed synthetic catalysts mimicking the activity of urokinase and tissue-plasminogen activator (and whose structures were constructed on the basic construct of the chymotryptic synthetic catalyst) based on the homology of the active site residues in the respective enzyme with chymotrypsin.

Expanding this successful approach further, Applicant initiated a computer search for sequences homologous to the active synthetic catalysts disclosed herein. The searches were accomplished using the FAST-DB (Fast Pairwise Comparison of Sequences—Release 5.4) sequence homology searching program as provided by Intelligenetics, Inc., 700 East El Camino Real, Mountain View, Calif. 94040. The searches were conducted in the publicly-available sequence databases—PIR39 and Swiss-Prot 28. Each search was accomplished by choosing a query sequence. The query sequence was chosen to represent the most complete sequence of each enzyme upon which successful synthetic catalysts had been modeled. Thus, the following query sequences were used:

ChPepz/TrPepz—Chymotrypsin (EC 3.4.21.1) B Precursor—bovine

LyPepz—Lysozyme (EC 3.2.1.17) c2—bovine

RnPepz—Ribonuclease A—bovine

In another extension, using the urokinase active site as the template, the structures of designed synthetic catalysts were deduced for urokinase-related enzymes.

The parameters for each search were virtually the same and were as follows:

Similarity matrix PAM-250
Threshold level of Sim. 13%
Mismatch Penalty 1
Gap Penalty 4.00
Gap Size Penalty 0.05
Cutoff score 2–4
Randomization Group 0
K-tuple 1
Joining Penalty 20
Window size 7–10
Initial scores to save 100
Optimized scores to save 100
Alignments to save 100
Display context 5

The scores were sorted by initial score and homologies were displayed comparing linear homology of each query sequence to each found sequence. Each such pairwise comparison was visually scanned for the active site residues previously found to be successfully integrated into the correlate synthetic catalyst.

The results of each such search are displayed in FIGS. 16–18A. Where homology was not significant in the active site regions or in certain cases where virtually identical homologies were located, the tabulated results are not necessarily shown. All of the alignments saved are displayed in FIGS. 16–18B. In each instance the number of the sequence identified in FIGS. 16–18A correspond to the named and similarly numbered sequence in FIGS. 16–18B.

The success of the method was marked. Very high degrees of homology were found in each such search. In many instances, only minor modifications/substitutions were uncovered. Whereas, as described herein, certain substitutions are likely to generate virtually identical activity in each homologous synthetic peptide, it is also possible that such modifications will result in a synthetic catalyst in which the activity will be modulated in certain regards (i.e., catalytic rate, substrate affinity, solubility, temperature sensitivity, etc.)

In any case, as in the case of use of ChPepz to successfully predict structure of the TrPepz catalyst, amino acids substitutions can be readily introduced and the resulting catalysts monitored for activity. For example, using the chymotrypsin search results and referring now to FIG. 16A and B, a trypsin homolog was predicted. Referring first to the active site residues listed in the heading of FIG. 16, it can be seen that the ChPepz contained residues $F_{39}$, $I_{99}$, $S_{189}$ and $M_{192}$. Referring now to Sequence No. 31 in FIG. 16A, it can be seen that the method predicts that an identical sequence, wherein $F_{39}$ is substituted by a tyrosine residue, $I_{99}$ is substituted by a leucine residue, $S_{189}$ is substituted by an aspartic acid residue and $M_{192}$ is substituted by a glutamine residue, will be active. Referring now to FIG. 16B, it can be seen that Sequence 31 is, in fact, a trypsin (EC 3.4.21.4) molecule. This approach, as noted above, resulted in the successful prediction of an entirely tryptic activity synthetic catalyst.

Extending this successful analogy only slightly, it can be seen in FIG. 16A and B that Sequence No. 27 varies from the trypsin homolog by only the substitution of $V_{213}$ (in chymotrypsin) with a threonine. By analogy, it is very likely that the trypsinogen II (EC 3.4.21.7) synthetic catalyst will be similarly active. Most, if not all, of the other homologs uncovered by the searches are predicted to result in similarly active catalysts.

Similarly, using active site homology of the serine proteases chymotrypsin and trypsin with urokinase and tissue plasminogen activator. Referring now to FIG. 19A and B, it can be seen that the active site residues for urokinase listed in the heading of the figure follow a highly similar pattern to those for chymotrypsin as follows:

Chymotrypsin Active Site Residues: Phe-His-Phe Ala-Ala-His-Cys Ile Asp Ser-Ser-Gly-Met-Gly-Asp-Ser Val-Ser-Trp Urokinase Active Site Residues: Thr-Tyr-Val Ala-Thr-His-Cys Leu Asp Asp-Ser-Gly-Gln-Gly-Asp-Ser Val-Ser-Trp Extending the analogy to predict an equivalent structure for a tissue plasminogen activator (TPA) (last listed sequence), the pattern similarity can be seen to be as follows:

Urokinase Active Site Residues: Thr-Tyr-Val Ala-Thr-His-Cys Leu Asp Asp-Ser-Gly-Gln-Gly-Asp-Ser Val-Ser-Trp TPA Active Site Residues: Arg-Phe-Leu- Ala-Ala-His-Cys Tyr Asp Asp-Ala-Gly-Gln-Gly-Asp-Ser Ile-Ser-Trp The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. Thus, it will be understood by those of skill in the art that any enzyme sequence and 3-dimensional information which is available will serve admirably well as a model. In certain instances, where the sequence is known but the 3-dimensional structure of the chosen enzyme is not known, a homologous protein whose 3-dimensional structure and sequence are known can be used as a model. For example, the structure of trypsin can be used to model peptide catalysts designed to possess the activity of urokinase and tissue plasminogen activator. In addition, as demonstrated by the substitution of the trypsin residues for those of chymotrypsin herein, substitutions of active site residues can be used to modulate, alter or to improve catalytic function. Additionally, it is anticipated that certain designs will be useful even where there is not a particularly impressive correlation with the native enzyme kinetics at maximal conditions since the synthetic catalysts may exhibit desirable characteristics under conditions where the native enzyme fails to function. All such modifications are intended to be included within the scope of the appended claims.

What is claimed is:

1. A peptide modeled on an active site of a naturally occurring enzyme and having the structure:

cyclo(-S-cystinyl-glycyl-phenylalanyl-histidyl-phenylalanyl-glycyl-glycyl-seryl-aspartyl-glycyl-methionyl-glycyl-seryl-seryl-glycyl-glycyl-valyl-seryl-tryptophanylglycyl-isoleucyl-glycyl-glycyl-aspartyl-glycyl-alanyl-alanyl-histidyl-cystinyl-S) (SEQ ID NO:1).

2. The peptide of claim 1, wherein said enzyme is chymotrypsin.

3. A peptide modeled on an active site of a naturally occurring enzyme and having the structure:

cyclo(-S-cystinyl-glycyl-tyrosyl-histidyl-phenylalanyl-glycyl-glycyl-seryl-aspartyl-glycyl-glutamyl-glycyl-seryl-aspartyl-glycyl-glycyl-valyl-seryl-tryptophanyl-glycyl-leucyl-glycyl-glycyl-aspartyl-glycyl-alanyl-alanyl-histidyl-cystinyl-S) (SEQ ID NO:2).

4. The peptide of claim 3, wherein said enzyme is trypsin.

5. A peptide modeled on an active site of a naturally occurring enzyme and having the structure:

cyclo(-S-cystinyl-threonyl-asparagyl-arginyl-asparagyl-glycyl-glycyl-aspartyl-glycyl-glycyl-leucyl-glutamyl-isoleucyl-asparagyl-glycyl-tryptophanyl-tryptophanyl-glycylglycyl-isoleucyl-glycyl-aspartyl-glycyl-aspartyl-glycyl-alanyl-tryptophanyl-valyl-alanylglycyl-arginyl-glycyl-phenylalanyl-glutamyl-seryl-asparagyl-cystinyl-S) (SEQ ID NO:3).

6. The peptide of claim 5, wherein said enzyme is lysozyme.

7. A peptide modeled on an active site of a naturally occurring enzyme and having the structure:

cyclo(-S-cystinyl-glutamyl-glycyl-valyl-histidyl-phenylalanyl-aspartyl-alanyl-serylglycyl-glycyl-threonyl-asparagyl-valyl-prolyl-lysyl-glycyl-glycyl-glutamyl-histidylglycyl-phenylalanyl-lysyl-cystinyl-S) (SEQ ID NO:4).

8. The peptide of claim 7, wherein said enzyme is ribonuclease.

9. A peptide modeled on an active site of a naturally occurring enzyme and having the structure:

cyclo(-S-cystinyl-glycyl-threonyl-tyrosyl-valyl-glycyl-glycyl-seryl-aspartyl-glycyl-glutaminyl-glycyl-seryl-aspartyl-glycyl-glycyl-valyl-seryl-tryptophanyl-glycyl-leucyl-glycyl-glycyl-aspartyl-glycyl-alanyl-threonyl-histidyl-cystinyl-S) (SEQ ID NO:5).

10. The peptide of claim 9, wherein said enzyme is urokinase.

11. A peptide modeled on an active site of a naturally occurring enzyme and having the structure:

cyclo(-S-cystinyl-glutamyl-arginyl-phenylalanyl-leucyl-glycyl-glycyl-seryl-aspartyl-glycyl-glutaminyl-glycyl-alanyl-aspartyl-glycyl-glycyl-isoleucyl-seryl-tryptophanyl-glycyl-tyrosyl-glycyl-glycyl-aspartyl-glycyl-alanyl-alanyl-histidyl-cystinyl-S) (SEQ ID NO:6).

12. The peptide of claim 11, wherein said enzyme is tissue plasminogen activator.

* * * * *

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 29 amino acids
        ( B ) TYPE: amino acid
        ( D ) TOPOLOGY: circular ( i i ) MOLECULE TYPE: protein ( i i i ) HYPOTHETICAL: NO ( i i i ) ANTI-SENSE: NO ( v ) FRAGMENT TYPE: not applicable ( x i ) SEQUENCE DESCRIPTION: SEQ ID NO: 1:

Cys Gly Phe His Phe Gly Gly Ser Asp Gly Met Gly Ser Ser Gly Gly
    1                      5                      10                      15

Val Ser Trp Gly Ile Gly Gly Asp Gly Ala Ala His Cys
                  20                      25

( 2 ) INFORMATION FOR SEQ ID NO: 2:

( i ) SEQUENCE CHARACTERISTICS:
        ( A ) LENGTH: 29 amino acids
        ( B ) TYPE: amino acid
        ( D ) TOPOLOGY: circular ( i i ) MOLECULE TYPE: protein ( i i i ) HYPOTHETICAL: NO ( v ) FRAGMENT TYPE: not applicable (x i) SEQUENCE DESCRIPTION: SEQ ID NO: 2:

Cys Gly Tyr His Phe Gly Gly Ser Asp Gly Glu Gly Ser Asp Gly Gly
1               5                   10                  15

Val Ser Trp Gly Leu Gly Gly Asp Gly Ala Ala His Cys
            20                  25

(2) INFORMATION FOR SEQ ID NO: 3:

(i) SEQUENCE CHARACTERISTICS:
        (A) LENGTH: 37 amino acids
        (B) TYPE: amino acid
        (D) TOPOLOGY: circular (i i) MOLECULE TYPE: protein (i i i) HYPOTHETICAL: NO (v) FRAGMENT TYPE: not applicable (x i) SEQUENCE DESCRIPTION: SEQ ID NO: 3:

Cys Thr Asn Arg Asn Gly Gly Asp Gly Gly Leu Glu Ile Asn Gly Trp
1               5                   10                  15

Trp Gly Gly Ile Gly Asp Gly Asp Gly Ala Trp Val Ala Gly Arg Gly
            20                  25                  30

Phe Glu Ser Asn Cys
            35

(2) INFORMATION FOR SEQ ID NO: 4:

(i) SEQUENCE CHARACTERISTICS:
        (A) LENGTH: 24 amino acids
        (B) TYPE: amino acid
        (D) TOPOLOGY: circular (i i) MOLECULE TYPE: protein (i i i) HYPOTHETICAL: NO (v) FRAGMENT TYPE: not applicable (x i) SEQUENCE DESCRIPTION: SEQ ID NO: 4:

Cys Glu Gly Val His Phe Asp Ala Ser Gly Gly Thr Asn Val Pro Lys
1               5                   10                  15

Gly Gly Glu His Gly Phe Lys Cys
            20

(2) INFORMATION FOR SEQ ID NO: 5:

(i) SEQUENCE CHARACTERISTICS:
        (A) LENGTH: 29 amino acids
        (B) TYPE: amino acid
        (D) TOPOLOGY: circular (i i) MOLECULE TYPE: protein (i i i) HYPOTHETICAL: NO (v) FRAGMENT TYPE: not applicable (x i) SEQUENCE DESCRIPTION: SEQ ID NO: 5:

Cys Gly Thr Tyr Val Gly Gly Ser Asp Gly Gln Gly Ser Asp Gly Gly
1               5                   10                  15

Val Ser Trp Gly Leu Gly Gly Asp Gly Ala Thr His Cys
            20                  25

(2) INFORMATION FOR SEQ ID NO: 6:

(i) SEQUENCE CHARACTERISTICS:
  (A) LENGTH: 29 amino acids
  (B) TYPE: amino acid
  (D) TOPOLOGY: circular (ii) MOLECULE TYPE: protein (iii) HYPOTHETICAL: NO (v) FRAGMENT TYPE: not applicable (xi) SEQUENCE DESCRIPTION: SEQ ID NO: 6:

```
Cys Glu Arg Phe Leu Gly Gly Ser Asp Gly Gln Gly Ala Asp Gly Gly
1               5                   10                  15
Ile Ser Trp Gly Tyr Gly Gly Asp Gly Ala Ala His Cys
                20                  25
```

(2) INFORMATION FOR SEQ ID NO:7:

(i) SEQUENCE CHARACTERISTICS:
  (A) LENGTH: 16 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: not applicable (xi) SEQUENCE DESCRIPTION: SEQ ID NO: 7:

```
Gln Leu Glu Pro Ser Thr Ser Ser Ala Val Pro Leu Ile Gly Lys Gly
1               5                   10                  15
```

(2) INFORMATION FOR SEQ ID NO:8:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: not applicable (xi) SEQUENCE DESCRIPTION: SEQ ID NO:8:

```
Ala Ala Met Lys Arg His Gly Leu Asp Asn
1               5                   10
```

(2) INFORMATION FOR SEQ ID NO:9:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: not applicable ( x i ) SEQUENCE DESCRIPTION: SEQ ID NO:9:

Asp Asn Tyr Arg Gly Tyr Ser Leu Gly
1               5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: not applicable ( x i ) SEQUENCE DESCRIPTION: SEQ ID NO:10:

Ala Lys Lys Ile Val Ser Asp Gly
1               5

( 2 ) INFORMATION FOR SEQ ID NO:11:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: not applicable ( x i ) SEQUENCE DESCRIPTION: SEQ ID NO:11:

Cys Asp Ser Gly Gly Val Ser Trp Gly Gly Leu Gly Asp Gly Ala Ala
1               5                   10                  15
His Gly Gly Phe His Tyr Cys
                20

( 2 ) INFORMATION FOR SEQ ID NO:12:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: not applicable ( x i ) SEQUENCE DESCRIPTION: SEQ ID NO:12:

Asp Ser Gly Glu Cys Asp Ser Gly Gly Val Ser Trp Gly Gly Leu Gly
1               5                   10                  15
Asp Gly Ala Ala His Gly Gly Phe His Tyr Cys
                20                  25

( 2 ) INFORMATION FOR SEQ ID NO:13:

( i ) SEQUENCE CHARACTERISTICS:
 ( A ) LENGTH: 26 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: not applicable ( x i ) SEQUENCE DESCRIPTION: SEQ ID NO:13:

```
Cys Phe Gly Gly Ser Asp Gly Glu Gly Ser Asp Gly Gly Val Ser Trp
1               5                   10                  15
Gly Leu Gly Gly Asp Gly Ala Ala His Cys
            20                  25
```